US010316081B2

(12) United States Patent
Rosenthal et al.

(10) Patent No.: US 10,316,081 B2
(45) Date of Patent: Jun. 11, 2019

(54) HUMANIZED ANTI-COMPLEMENT FACTOR C1Q ANTIBODIES

(71) Applicant: Annexon, Inc., South San Francisco, CA (US)

(72) Inventors: Arnon Rosenthal, Woodside, CA (US); Michael Leviten, Emerald Hills, CA (US)

(73) Assignee: Annexon, Inc., South San Francisco, CA (US)

( * ) Notice: Subject to any disclaimer, the term of this patent is extended or adjusted under 35 U.S.C. 154(b) by 457 days.

(21) Appl. No.: 14/933,517

(22) Filed: Nov. 5, 2015

(65) Prior Publication Data

US 2016/0355574 A1  Dec. 8, 2016

Related U.S. Application Data

(60) Provisional application No. 62/075,793, filed on Nov. 5, 2014.

(51) Int. Cl.
*C07K 16/18* (2006.01)
*A61K 39/395* (2006.01)
*G01N 33/564* (2006.01)
*G01N 33/68* (2006.01)
*A61K 49/00* (2006.01)
*A61K 39/00* (2006.01)

(52) U.S. Cl.
CPC .......... *C07K 16/18* (2013.01); *A61K 49/0002* (2013.01); *G01N 33/564* (2013.01); *G01N 33/6893* (2013.01); *G01N 33/6896* (2013.01); *A61K 2039/505* (2013.01); *C07K 2317/24* (2013.01); *C07K 2317/34* (2013.01); *C07K 2317/52* (2013.01); *C07K 2317/55* (2013.01); *C07K 2317/56* (2013.01); *C07K 2317/76* (2013.01); *C07K 2317/92* (2013.01); *C07K 2317/94* (2013.01); *G01N 2333/4716* (2013.01)

(58) Field of Classification Search
None
See application file for complete search history.

(56) References Cited

U.S. PATENT DOCUMENTS

| | | | |
|---|---|---|---|
| 6,197,930 B1 | 3/2001 | Sheppard et al. | |
| 8,025,878 B2 | 9/2011 | Gellerfors et al. | |
| 9,708,394 B2 | 7/2017 | Rosenthal et al. | |
| 2002/0058311 A1* | 5/2002 | Browne | C07K 14/5759 435/69.7 |
| 2002/0066117 A1 | 5/2002 | Nilsson et al. | |
| 2002/0104104 A1 | 8/2002 | Games et al. | |
| 2002/0160433 A1 | 10/2002 | Welch et al. | |
| 2003/0170781 A1 | 9/2003 | Holloway et al. | |
| 2004/0248156 A1 | 12/2004 | Hu et al. | |
| 2005/0197285 A1 | 9/2005 | Rosen et al. | |
| 2005/0214786 A1 | 9/2005 | Birse et al. | |
| 2005/0241008 A1 | 10/2005 | Bredesen et al. | |
| 2007/0135753 A1 | 6/2007 | Barres et al. | |
| 2007/0269435 A1* | 11/2007 | Gillies | C07K 16/28 424/138.1 |
| 2008/0241145 A1 | 10/2008 | Goldenberg et al. | |
| 2010/0143343 A1 | 6/2010 | Halstead et al. | |
| 2011/0104156 A1 | 5/2011 | Christadoss et al. | |
| 2012/0328601 A1 | 12/2012 | Barres et al. | |
| 2013/0344073 A1 | 12/2013 | Schwaeble et al. | |
| 2014/0140933 A1 | 5/2014 | Van Vlasselaer et al. | |
| 2015/0259437 A1 | 9/2015 | Van Vlasselaer et al. | |
| 2016/0159890 A1* | 6/2016 | Rosenthal | C07K 16/18 424/136.1 |
| 2016/0326237 A1* | 11/2016 | Rosenthal | C07K 16/40 |
| 2016/0368973 A1 | 12/2016 | Rosenthal et al. | |
| 2017/0152309 A1 | 6/2017 | Yednock et al. | |

FOREIGN PATENT DOCUMENTS

| | | |
|---|---|---|
| EP | 1774972 A1 | 4/2007 |
| EP | 2266606 A1 | 12/2010 |
| WO | WO-1985/02261 A1 | 5/1985 |
| WO | WO-1998/23761 A1 | 6/1998 |
| WO | WO-2003/052377 A2 | 6/2003 |
| WO | WO-2005/002513 A2 | 1/2005 |
| WO | WO-2007/070375 A2 | 6/2007 |
| WO | WO-2012/176765 A1 | 12/2012 |
| WO | WO-2014/066744 A2 | 5/2014 |
| WO | WO-2014/161570 A1 | 10/2014 |
| WO | WO-2014/169076 A1 | 10/2014 |
| WO | WO-2014/186599 A2 | 11/2014 |
| WO | WO-2014/186622 A2 | 11/2014 |
| WO | WO-2015/006504 A1 | 1/2015 |
| WO | WO-2015/006507 A1 | 1/2015 |

OTHER PUBLICATIONS

Rudikoff et al. Proc Natl Acad Sci USA 79: 1979-1983 (1982)*
Colman, Research in Immunology 145: 33-36 (1994).*
Kussie et al., J. Immunol. 152: 146-152 (1994).*
Chen et al., EMBO J., 14: 2784-2794 (1995).*
"Complement C1s antibody (49)," Product Data Sheet. ThermScientific. Pierce Antibody Products. 1995. pp. 1-2. Retrieved from the Internet: <http://www.pierce-antibodies.com/ <http://www.pierce-antibodies.com/>Complement-C1s-antibody-clone-49-monoclonal-ABS0024902.html#> on Sep. 23, 2014 (Sep. 23, 2014).
Carroll et al., "Antibody-mediates inhibition of human C1s and the classical complement pathway," Immunobiology, 218:1041-8 (2013).
Hampel et al., "The future of Alzheimer's disease: the next 10 years," Prog Neurobiol, 95(4): 718-28 (Dec. 2011).
International Search Report and Written Opinion dated Apr. 2, 2015 from related PCT Application PCT/US14/038239.
International Search Report and Written Opinion dated Mar. 18, 2008 from related PCT Application PCT/US06/046857.
International Search Report and Written Opinion dated Nov. 7, 2014 from related PCT Application PCT/US14/038267.
International Search Report and Written Opinion dated Sep. 3, 2014 from related PCT Application PCT/US14/33560.
International Search Report and Written Opinion from related PCT Application PCT/US14/046045, dated Nov. 4, 2014.

(Continued)

*Primary Examiner* — Phillip Gambel
(74) *Attorney, Agent, or Firm* — Foley Hoag LLP

(57) ABSTRACT

The present disclosure is directed to humanized anti-C1q antibodies and methods of using them.

30 Claims, 14 Drawing Sheets
Specification includes a Sequence Listing.

(56) References Cited

OTHER PUBLICATIONS

McGonigal, et al., "C1q-targeted inhibition of the classical complement pathway prevents injury in a novel mouse model of acute motor axonal neuropathy," Acta Neuropathologica Comm, 9(3): 729 (2016).
McGreer et al., "The future use of complement inhibitors for the treatment of neurological diseases," Drugs, 55(6):739-46 (1998).
Morgan et al., "The role of complement disorders of the nervous system," Immunopharmacology, 38:43-50 (1997).
Pardridge et al., "Reengineering Biopharmaceuticals for Targeted Delivery Across the Blood-Brain Barrier," Methods in Enzymology, Academic Press, US, 503: 269-292 (Jan. 1, 2012).
Perrin et al., "Multimodal Techniques for Diagnosis and Prognosis of Alzheimer's disease," Nature, 461(7266): 916-922 (Oct. 15, 2009).
Phuan et al., "C1q-targeted monoclonal antibody prevents complement dependent cytotoxicity and neuropathology in in vitro and mouse models of neuromyelitis optica," Acta Neuropathol, 125(6):829-40 (2013).
Roos et al., "Specific inhibition of the classical complement pathway by C1q-binding peptides," J Immunol, 167(12):7052-9 (2001).
Sahu et al., "Complement inhibitors: a resurgent concept in anti-inflammatory therapeutics," Immunopharmacology, 49(1-2):133-48 (2000).
Supplementary European Search Report for European Application No. EP 14 82 2330 dated Nov. 15, 2016.
Tradtrantip et al., "Enzymatic deglycosylation converts pathogenic neuromyelitis optica anti-aquaporin-4 IgG into therapeutic antibody," Ann Neutol, 73(1):77-85 (2013).
Vickers, "A vaccine against Alzheimer's disease: developments to date," Drugs Aging, 19(7): 487-494 (2002).
Angal et al., "A single amino acid substitution abolishes the heterogeneity of chimeric mouse/human (IgG4) antibody," Molecular Immunol, 30(1):105-8 (1993).
Hu et al., "Characterization of C1q in teleosts: insight into the molecular and functional evolution of C1q family and classical pathway," J Biol Chem, 285:28777-86 (2010).
International Search Report and Written Opinion dated Jan. 27, 2016 for related PCT Application PCT/US2015/059185.
International Search Report and Written Opinion dated Dec. 5, 2014 from corresponding PCT Application PCT/US14/046042.
Lopez-Requena et al., "Immunogenicity of autologous immunoglobulins: Principles and practices," Molecular Immunol, 44:3076-82 (2007).
Reddy et al., "Elimination of Fc receptor-dependent effector functions of a modified IgG4 monoclonal antibody to human CD4," J Immunol, 164(4):1925-33 (2000).
Tuzun et al., "Targeting classical complement pathway to treat complement mediated autoimmune diseases," Current Topics in Complement II.Springer US, Jul. 26, 2008. p. 254-61. [online], [retrieved on Jan. 25, 2016]. Retrieved from the Internet: <http://link.springer.com/chapter/10.1007/978-0-387-78952-1_19>.
Brown et al., "Tolerance of single, but not multiple, amino acid replacements in antibody VH CDR 2: a means of minimizing B cell wastage from somatic hypermutation?" J Immunol, 156(9):3285-3291 (1996).
Extended European Search Report issued by the European Patent Office in corresponding Application No. EP 15857258.6, dated Mar. 20, 2018.
Gershoni et al., "Epitope mapping: the first step in developing epitope-based vaccines," BioDrugs, 21(3):145-156 (2007).

\* cited by examiner

FIGURE 2A

Alignment of amino acid sequence of the heavy chain variable region (VH) of M1 anti-C1q and the amino acid sequences of the humanized VH variants 1-2

VH variant 1:

```
M1_VH    1 QVQLQQPGAELVKPGASVKLSCKSSGYHFTSYWMHWVKQRPGQGLEWIGV    50
           |||||.|||.||||||||||.|||||||||||||||.|||||.|||||||
VH1      1 QVQLVQSGAELKKPGASVKVSCKSSGYHFTSYWMHWVKQAPGQGLEWIGV    50

M1_VH   51 IHPNSGSINYNEKFESKATLTVDKSSSTAYMQLSSLTSEDSAVYYCAGER  100
           ||||||||||||||||:||||.||||||||||||||||||||||||||||
VH1     51 IHPNSGSINYNEKFESRATITVDRSTSTAYMQLSSLTSEDSAVYYCAGER  100

M1_VH  101 DSTEVLPMDYWGQGTSVTVSS  121
           |||||||||||||||||||||
VH1    101 DSTEVLPMDYWGQGTTVTVSS  121
```

M1_VH refers to the VH of the M1 antibody, and VH1 refers to VH variant 1. The three CDR sequences are depicted in bold.

VH variant 2:

```
M1_VH    1 QVQLQQPGAELVKPGASVKLSCKSSGYHFTSYWMHWVKQRPGQGLEWIGV    50
           |||||.|||.||||||||||.|||||||||||||||.|||||.|||||||
VH2      1 QVQLVQSGAELKKPGASVKVSCKSSGYHFTSYWMHWVKQAPGQGLEWIGV    50

M1_VH   51 IHPNSGSINYNEKFESKATLTVDKSSSTAYMQLSSLTSEDSAVYYCAGER  100
           ||||||||||||||||:||||.||||||||:|||||:|||||||||||||
VH2     51 IHPNSGSINYNEKFESRATITVDRSTSTAYMELSSLRSEDSAVYYCAGER  100

M1_VH  101 DSTEVLPMDYWGQGTSVTVSS  121
           |||||||||||||||||||||
VH2    101 DSTEVLPMDYWGQGTTVTVSS  121
```

M1_VH refers to the VH of the M1 antibody, and VH2 refers to VH variant 2. The three CDR sequences are depicted in bold.

FIGURE 2B

Alignment of amino acid sequence of the heavy chain variable region (VH) of M1 anti-C1q and the amino acid sequences of the humanized VH variants 3-4

VH variant 3:

```
M1_VH    1  QVQLQQPGAELVKPGASVKLSCKSSGYHFTSYWMHWVKQRPGQGLEWIGV     50
            |||| ||| ||||||||| ||||||||||||||||||||  |||||||||
VH3      1  QVQLVQSGAELKKPGASVKVSCKSSGYHFTSYWMHWVRQAPGQGLEWIGV     50

M1_VH   51  IHPNSGSINYNEKFESKATLTVDKSSSTAYMQLSSLTSEDSAVYYCAGER    100
            ||||||||||||||||||| ||||||||| ||| |||| |||||||||||
VH3     51  IHPNSGSINYNEKFESRVTITVDKSTSTAYMELSSLRSEDTAVYYCAGER    100

M1_VH  101  DSTEVLPMDYWGQGTSVTVSS    121
            ||||||||||||||||| |||
VH3    101  DSTEVLPMDYWGQGTTVTVSS    121
```

M1_VH refers to the VH of the M1 antibody, and VH3 refers to VH variant 3. The three CDR sequences are depicted in bold.

VH variant 4:

```
M1_VH    1  QVQLQQPGAELVKPGASVKLSCKSSGYHFTSYWMHWVKQRPGQGLEWIGV     50
            |||| ||| ||||||||| ||||||||||||||||||||  |||||||||
VH4      1  QVQLVQSGAELKKPGASVKVSCKSSGYHFTSYWMHWVRQAPGQGLEWIGV     50

M1_VH   51  IHPNSGSINYNEKFESKATLTVDKSSSTAYMQLSSLTSEDSAVYYCAGER    100
            ||||||||||||||||| | ||||||| ||||||| |||| |||||||||
VH4     51  IHPNSGSINYNEKFESRVTITVDKSTSTAYMELSSLRSEDTAVYYCAGER    100

M1_VH  101  DSTEVLPMDYWGQGTSVTVSS    121
            ||||||||||||||||| |||
VH4    101  DSTEVLPMDYWGQGTTVTVSS    121
```

M1_VH refers to the VH of the M1 antibody, and VH4 refers to VH variant 4. The three CDR sequences are depicted in bold.

FIGURE 2C

Alignment of amino acid sequence of the kappa light chain variable region (Vκ) of M1 anti-C1q and the amino acid sequences of the humanized Vκ variants 1-2.

Vκ variant 1

```
M1_VK    1  DVQITQSPSYLAASPGETITINCRASKSINKYLAWYQEKPGKTNKLLIYS   50
            ||||||||||:|||:||.||||||||||||||||||||:||||||||||
VK1      1  DVQITQSPSYLAASIGERATINCRASKSINKYLAWYQQKPGKTNKLLIYS   50

M1_VK   51  GSTLQSGIPSRFSGSGSGTDFTLTISSLEPEDFAMYYCQQHNEYPLTFGA  100
            ||||||||||||||||||||||||||||||||||||||||||||||||.
VK1     51  GSTLQSGIPSRFSGSGSGTDFTLTISSLEPEDFAMYYCQQHNEYPLTFGQ  100

M1_VK  101  GTKLELK  107
            |||||:|
VK1    101  GTKLEIK  107
```

M1_VK refers to the Vκ of the M1 antibody, and VK1 refers to Vκ variant 1. The three CDR sequences are depicted in bold.

Vκ variant 2

```
M1_VK    1  DVQITQSPSYLAASPGETITINCRASKSINKYLAWYQEKPGKTNKLLIYS   50
            ||||||||||:|||:||.||||||||||||||||||||:||||:|||||
VK2      1  DVQITQSPSSLSASIGERATINCRASKSINKYLAWYQQKPGKAKKLLIYS   50

M1_VK   51  GSTLQSGIPSRFSGSGSGTDFTLTISSLEPEDFAMYYCQQHNEYPLTFGA  100
            ||||||||||||||||||||||||||||||||||||||||||||||||.
VK2     51  GSTLQSGIPSRFSGSGSGTDFTLTISSLEPEDFAMYYCQQHNEYPLTFGQ  100

M1_VK  101  GTKLELK  107
            |||||:|
VK2    101  GTKLEIK  107
```

M1_VK refers to the Vκ of the M1 antibody, and VK2 refers to Vκ variant 2. The three CDR sequences are depicted in bold.

FIGURE 2D

Alignment of amino acid sequence of the kappa light chain variable region (Vκ) of M1 anti-C1q and the amino acid sequences of the humanized Vκ variants 3-4.

Vκ variant 3:

```
M1_VK    1  DVQITQSPSYLAASPGETITINCRASKSINKYLAWYQEKPGKTNKLLIYS   50
            ||||||||| ||||||| |||||||||||||||||||||  ||||||||
VK3      1  DVQMTQSPSSLSASLGERATINCRASKSINKYLAWYQQKPGKAPKLLIYS   50

M1_VK   51  GSTLQSGIPSRFSGSGSGTDFTLTISSLEPEDFAMYYCQQHNEYPLTFGA  100
            |||||||||||||||||||||||||||||||||||||||||||||||
VK3     51  GSTLQSGIPARFSGSGSGTDFTLTISSLEPEDFATYYCQQHNEYPLTFGQ  100

M1_VK  101  GTKLELK                                             107
            ||||| |
VK3    101  GTKLEIK                                             107
```

M1_VK refers to the Vκ of the M1 antibody, and VK3 refers to Vκ variant 3. The three CDR sequences are depicted in bold.

Vκ variant 4:

```
M1_VK    1  DVQITQSPSYLAASPGETITINCRASKSINKYLAWYQEKPGKTNKLLIYS   50
            ||||||||| ||||||| |||||||||||||||||||||  ||||||||
VK4      1  DIQMTQSPSSLSASLGERATINCRASKSINKYLAWYQQKPGKAPKLLIYS   50

M1_VK   51  GSTLQSGIPSRFSGSGSGTDFTLTISSLEPEDFAMYYCQQHNEYPLTFGA  100
            |||||||||||||||||||||||||||||||||||||||||||||||
VK4     51  GSTLQSGIPARFSGSGSGTDFTLTISSLEPEDFAMYYCQQHNEYPLTFGQ  100

M1_VK  101  GTKLELK                                             107
            ||||| |
VK4    101  GTKLEIK                                             107
```

M1_VK refers to the Vκ of the M1 antibody, and VK4 refers to Vκ variant 4. The three CDR sequences are depicted in bold.

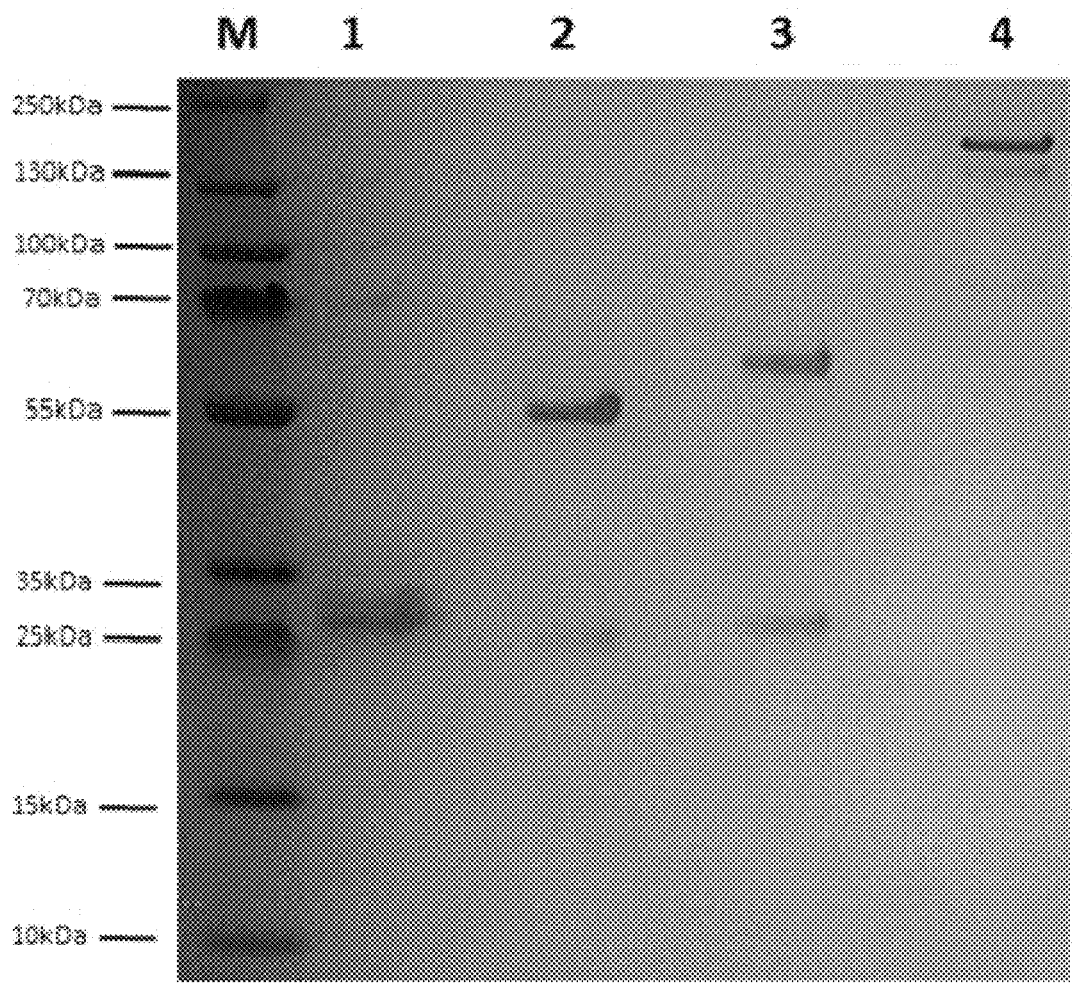

SEQUENCE LISTING

<160> NUMBER OF SEQ ID NOS: 46

<210> SEQ ID NO 1
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Val Gln Ser Gly Ala Glu Leu Lys Lys Pro Gly Ala
1               5                   10                  15

```
Ser Val Lys Val Ser Cys Lys Ser Gly Tyr His Phe Thr Ser Tyr
            20                  25                  30

Trp Met His Trp Val Lys Gln Ala Pro Gly Gln Gly Leu Glu Trp Ile
        35                  40                  45

Gly Val Ile His Pro Asn Ser Gly Ser Ile Asn Tyr Asn Glu Lys Phe
50                  55                  60

Glu Ser Lys Ala Thr Ile Thr Val Asp Lys Ser Thr Ser Thr Ala Tyr
65                  70                  75                  80

Met Gln Leu Ser Ser Leu Thr Ser Glu Asp Ser Ala Val Tyr Tyr Cys
                85                  90                  95

Ala Gly Glu Arg Asp Ser Thr Glu Val Leu Pro Met Asp Tyr Trp Gly
            100                 105                 110

Gln Gly Thr Ser Val Thr Val Ser Ser
        115                 120

<210> SEQ ID NO 2
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Gln Leu Val Gln Ser Gly Ala Glu Leu Lys Lys Pro Gly Ala
1               5                   10                  15

Ser Val Lys Val Ser Cys Lys Ser Gly Tyr His Phe Thr Ser Tyr
            20                  25                  30

Trp Met His Trp Val Lys Gln Ala Pro Gly Gln Gly Leu Glu Trp Ile
        35                  40                  45

Gly Val Ile His Pro Asn Ser Gly Ser Ile Asn Tyr Asn Glu Lys Phe
50                  55                  60

Glu Ser Arg Ala Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Glu Arg Asp Ser Thr Glu Val Leu Pro Met Asp Tyr Trp Gly
            100                 105                 110

Gln Gly Thr Thr Val Thr Val Ser Ser
        115                 120

<210> SEQ ID NO 3
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Val Gln Ser Gly Ala Glu Leu Lys Lys Pro Gly Ala
1               5                   10                  15

Ser Val Lys Val Ser Cys Lys Ser Gly Tyr His Phe Thr Ser Tyr
            20                  25                  30

Trp Met His Trp Val Lys Gln Ala Pro Gly Gln Gly Leu Glu Trp Ile
        35                  40                  45

Gly Val Ile His Pro Asn Ser Gly Ser Ile Asn Tyr Asn Glu Lys Phe
50                  55                  60
```

Glu Ser Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Glu Arg Asp Ser Thr Glu Val Leu Pro Met Asp Tyr Trp Gly
            100                 105                 110

Gln Gly Thr Thr Val Thr Val Ser Ser
        115                 120

<210> SEQ ID NO 4
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Val Gln Leu Val Gln Ser Gly Ala Glu Leu Lys Lys Pro Gly Ala
1               5                   10                  15

Ser Val Lys Val Ser Cys Lys Ser Ser Gly Tyr His Phe Thr Ser Tyr
            20                  25                  30

Trp Met His Trp Val Arg Gln Ala Pro Gly Gln Gly Leu Glu Trp Ile
        35                  40                  45

Gly Val Ile His Pro Asn Ser Gly Ser Ile Asn Tyr Asn Glu Lys Phe
    50                  55                  60

Glu Ser Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Glu Arg Asp Ser Thr Glu Val Leu Pro Met Asp Tyr Trp Gly
            100                 105                 110

Gln Gly Thr Thr Val Thr Val Ser Ser
        115                 120

<210> SEQ ID NO 5
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Val Gln Ile Thr Gln Ser Pro Ser Tyr Leu Ala Ala Ser Leu Gly
1               5                   10                  15

Glu Arg Ala Thr Ile Asn Cys Arg Ala Ser Lys Ser Ile Asn Lys Tyr
            20                  25                  30

Leu Ala Trp Tyr Gln Gln Lys Pro Gly Lys Thr Asn Lys Leu Leu Ile
        35                  40                  45

Tyr Ser Gly Ser Thr Leu Gln Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Leu
                85                  90                  95

Thr Phe Gly Gln Gly Thr Lys Leu Glu Ile Lys
            100                 105

<210> SEQ ID NO 6
<211> LENGTH: 107
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 6

Asp Val Gln Ile Thr Gln Ser Pro Ser Ser Leu Ser Ala Ser Leu Gly
1               5                   10                  15

Glu Arg Ala Thr Ile Asn Cys Arg Ala Ser Lys Ser Ile Asn Lys Tyr
            20                  25                  30

Leu Ala Trp Tyr Gln Gln Lys Pro Gly Lys Ala Asn Lys Leu Leu Ile
        35                  40                  45

Tyr Ser Gly Ser Thr Leu Gln Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Leu
                85                  90                  95

Thr Phe Gly Gln Gly Thr Lys Leu Glu Ile Lys
            100                 105

<210> SEQ ID NO 7
<211> LENGTH: 107
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 7

Asp Val Gln Ile Thr Gln Ser Pro Ser Ser Leu Ser Ala Ser Leu Gly
1               5                   10                  15

Glu Arg Ala Thr Ile Asn Cys Arg Ala Ser Lys Ser Ile Asn Lys Tyr
            20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Leu
                85                  90                  95

Thr Phe Gly Gln Gly Thr Lys Leu Glu Ile Lys
            100                 105

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 8

Asp Ile Gln Leu Thr Gln Ser Pro Ser Ser Leu Ser Ala Ser Leu Gly
1               5                   10                  15

Glu Arg Ala Thr Ile Asn Cys Arg Ala Ser Lys Ser Ile Asn Lys Tyr
            20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Ile Pro Ala Arg Phe Ser Gly
 50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Leu
                85                  90                  95

Thr Phe Gly Gln Gly Thr Lys Leu Glu Ile Lys
            100                 105

<210> SEQ ID NO 9
<211> LENGTH: 245
<212> TYPE: PRT
<213> ORGANISM: Homo sapiens

<400> SEQUENCE: 9

Met Glu Gly Pro Arg Gly Trp Leu Val Leu Cys Val Leu Ala Ile Ser
1               5                   10                  15

Leu Ala Ser Met Val Thr Glu Asp Leu Cys Arg Ala Pro Asp Gly Lys
            20                  25                  30

Lys Gly Glu Ala Gly Arg Pro Gly Arg Arg Gly Arg Pro Gly Leu Lys
        35                  40                  45

Gly Glu Gln Gly Glu Pro Gly Ala Pro Gly Ile Arg Thr Gly Ile Gln
 50                  55                  60

Gly Leu Lys Gly Asp Gln Gly Glu Pro Gly Pro Ser Gly Asn Pro Gly
65                  70                  75                  80

Lys Val Gly Tyr Pro Gly Pro Ser Gly Pro Leu Gly Ala Arg Gly Ile
                85                  90                  95

Pro Gly Ile Lys Gly Thr Lys Gly Ser Pro Gly Asn Ile Lys Asp Gln
            100                 105                 110

Pro Arg Pro Ala Phe Ser Ala Ile Arg Arg Asn Pro Pro Met Gly Gly
        115                 120                 125

Asn Val Val Ile Phe Asp Thr Val Ile Thr Asn Gln Glu Glu Pro Tyr
130                 135                 140

Gln Asn His Ser Gly Arg Phe Val Cys Thr Val Pro Gly Tyr Tyr Tyr
145                 150                 155                 160

Phe Thr Phe Gln Val Leu Ser Gln Trp Glu Ile Cys Leu Ser Ile Val
                165                 170                 175

Ser Ser Ser Arg Gly Gln Val Arg Arg Ser Leu Gly Phe Cys Asp Thr
            180                 185                 190

Thr Asn Lys Gly Leu Phe Gln Val Ser Gly Gly Met Val Leu Gln
        195                 200                 205

Leu Gln Gln Gly Asp Gln Val Trp Val Glu Lys Asp Pro Lys Lys Gly
210                 215                 220

His Ile Tyr Gln Gly Ser Glu Ala Asp Ser Val Phe Ser Gly Phe Leu
225                 230                 235                 240

Ile Phe Pro Ser Ala
            245

<210> SEQ ID NO 10
<211> LENGTH: 253
<212> TYPE: PRT
<213> ORGANISM: Homo sapiens

<400> SEQUENCE: 10

| Met | Met | Met | Lys | Ile | Pro | Trp | Gly | Ser | Ile | Pro | Val | Leu | Met | Leu | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Leu Leu Leu Gly Leu Ile Asp Ile Ser Gln Ala Gln Leu Ser Cys Thr
          20                25              30

Gly Pro Pro Ala Ile Pro Gly Ile Pro Gly Ile Pro Gly Thr Pro Gly
                35                  40                  45

Pro Asp Gly Gln Pro Gly Thr Pro Gly Ile Lys Gly Glu Lys Gly Leu
 50                  55                  60

Pro Gly Leu Ala Gly Asp His Gly Glu Phe Gly Glu Lys Gly Asp Pro
 65                  70                  75                  80

Gly Ile Pro Gly Asn Pro Gly Lys Val Gly Pro Lys Gly Pro Met Gly
                 85                  90                  95

Pro Lys Gly Gly Pro Gly Ala Pro Gly Ala Pro Gly Pro Lys Gly Glu
                100                 105                 110

Ser Gly Asp Tyr Lys Ala Thr Gln Lys Ile Ala Phe Ser Ala Thr Arg
                115                 120                 125

Thr Ile Asn Val Pro Leu Arg Arg Asp Gln Thr Ile Arg Phe Asp His
130                 135                 140

Val Ile Thr Asn Met Asn Asn Tyr Glu Pro Arg Ser Gly Lys Phe
145                 150                 155                 160

Thr Cys Lys Val Pro Gly Leu Tyr Tyr Phe Thr Tyr His Ala Ser Ser
                165                 170                 175

Arg Gly Asn Leu Cys Val Asn Leu Met Arg Gly Arg Glu Arg Ala Gln
                180                 185                 190

Lys Val Val Thr Phe Cys Asp Tyr Ala Tyr Asn Thr Phe Gln Val Thr
                195                 200                 205

Thr Gly Gly Met Val Leu Lys Leu Glu Gln Gly Glu Asn Val Phe Leu
 210                 215                 220

Gln Ala Thr Asp Lys Asn Ser Leu Leu Gly Met Glu Gly Ala Asn Ser
225                 230                 235                 240

Ile Phe Ser Gly Phe Leu Leu Phe Pro Asp Met Glu Ala
                245                 250

<210> SEQ ID NO 11
<211> LENGTH: 245
<212> TYPE: PRT
<213> ORGANISM: Homo sapiens

<400> SEQUENCE: 11

Met Asp Val Gly Pro Ser Ser Leu Pro His Leu Gly Leu Lys Leu Leu
1               5                   10                  15

Leu Leu Leu Leu Leu Pro Leu Arg Gly Gln Ala Asn Thr Gly Cys
                20                  25                  30

Tyr Gly Ile Pro Gly Met Pro Gly Leu Pro Gly Ala Pro Gly Lys Asp
                35                  40                  45

Gly Tyr Asp Gly Leu Pro Gly Pro Lys Gly Glu Pro Gly Ile Pro Ala
 50                  55                  60

Ile Pro Gly Ile Arg Gly Pro Lys Gly Gln Lys Gly Glu Pro Gly Leu
 65                  70                  75                  80

Pro Gly His Pro Gly Lys Asn Gly Pro Met Gly Pro Pro Gly Met Pro
                 85                  90                  95

Gly Val Pro Gly Pro Met Gly Ile Pro Gly Glu Pro Gly Glu Glu Gly
                100                 105                 110

Arg Tyr Lys Gln Lys Phe Gln Ser Val Phe Thr Val Thr Arg Gln Thr
            115                 120                 125

His Gln Pro Pro Ala Pro Asn Ser Leu Ile Arg Phe Asn Ala Val Leu
        130                 135                 140

Thr Asn Pro Gln Gly Asp Tyr Asp Thr Ser Thr Gly Lys Phe Thr Cys
145                 150                 155                 160

Lys Val Pro Gly Leu Tyr Tyr Phe Val Tyr His Ala Ser His Thr Ala
                165                 170                 175

Asn Leu Cys Val Leu Leu Tyr Arg Ser Gly Val Lys Val Val Thr Phe
            180                 185                 190

Cys Gly His Thr Ser Lys Thr Asn Gln Val Asn Ser Gly Val Leu
                195                 200                 205

Leu Arg Leu Gln Val Gly Glu Glu Val Trp Leu Ala Val Asn Asp Tyr
        210                 215                 220

Tyr Asp Met Val Gly Ile Gln Gly Ser Asp Ser Val Phe Ser Gly Phe
225                 230                 235                 240

Leu Leu Phe Pro Asp
            245

<210> SEQ ID NO 12
<211> LENGTH: 31
<212> TYPE: PRT
<213> ORGANISM: Homo sapiens

<400> SEQUENCE: 12

Gly Leu Phe Gln Val Val Ser Gly Gly Met Val Leu Gln Leu Gln Gln
1               5                   10                  15

Gly Asp Gln Val Trp Val Glu Lys Asp Pro Lys Lys Gly His Ile
            20                  25                  30

<210> SEQ ID NO 13
<211> LENGTH: 26
<212> TYPE: PRT
<213> ORGANISM: Homo sapiens

<400> SEQUENCE: 13

Gly Leu Phe Gln Val Val Ser Gly Gly Met Val Leu Gln Leu Gln Gln
1               5                   10                  15

Gly Asp Gln Val Trp Val Glu Lys Asp Pro
            20                  25

<210> SEQ ID NO 14
<211> LENGTH: 20
<212> TYPE: PRT
<213> ORGANISM: Homo sapiens

<400> SEQUENCE: 14

Ser Gly Gly Met Val Leu Gln Leu Gln Gln Gly Asp Gln Val Trp Val
1               5                   10                  15

Glu Lys Asp Pro
            20

<210> SEQ ID NO 15
<211> LENGTH: 18
<212> TYPE: PRT
<213> ORGANISM: Homo sapiens

<400> SEQUENCE: 15

Ser Gly Gly Met Val Leu Gln Leu Gln Gln Gly Asp Gln Val Trp Val

```
                1               5                   10                  15

Glu Lys

<210> SEQ ID NO 16
<211> LENGTH: 23
<212> TYPE: PRT
<213> ORGANISM: Homo sapiens

<400> SEQUENCE: 16

Trp Leu Ala Val Asn Asp Tyr Tyr Asp Met Val Gly Ile Gln Gly Ser
1               5                   10                  15

Asp Ser Val Phe Ser Gly Phe
            20

<210> SEQ ID NO 17
<211> LENGTH: 16
<212> TYPE: PRT
<213> ORGANISM: Homo sapiens

<400> SEQUENCE: 17

Tyr Asp Met Val Gly Ile Gln Gly Ser Asp Ser Val Phe Ser Gly Phe
1               5                   10                  15

<210> SEQ ID NO 18
<211> LENGTH: 8
<212> TYPE: PRT
<213> ORGANISM: Homo sapiens

<400> SEQUENCE: 18

Tyr Asp Met Val Gly Ile Gln Gly
1               5

<210> SEQ ID NO 19
<211> LENGTH: 23
<212> TYPE: PRT
<213> ORGANISM: Homo sapiens

<400> SEQUENCE: 19

His Thr Ala Asn Leu Cys Val Leu Leu Tyr Arg Ser Gly Val Lys Val
1               5                   10                  15

Val Thr Phe Cys Gly His Thr
            20

<210> SEQ ID NO 20
<211> LENGTH: 9
<212> TYPE: PRT
<213> ORGANISM: Homo sapiens

<400> SEQUENCE: 20

Arg Ser Gly Val Lys Val Val Thr Phe
1               5

<210> SEQ ID NO 21
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Gln Gln Pro Gly Ala Glu Leu Val Lys Pro Gly Ala
1               5                   10                  15
```

```
Ser Val Lys Leu Ser Cys Lys Ser Gly Tyr His Phe Thr Ser Tyr
            20                  25                  30

Trp Met His Trp Val Lys Gln Arg Pro Gly Gln Gly Leu Glu Trp Ile
        35                  40                  45

Gly Val Ile His Pro Asn Ser Gly Ser Ile Asn Tyr Asn Glu Lys Phe
    50                  55                  60

Glu Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Gly Glu Arg Asp Ser Thr Glu Val Leu Pro Met Asp Tyr Trp Gly
            100                 105                 110

Gln Gly Thr Ser Val Thr Val Ser Ser
            115                 120

<210> SEQ ID NO 22
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Asn Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Leu
                85                  90                  95

Thr Phe Gly Ala Gly Thr Lys Leu Glu Leu Lys
            100                 105

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Tyr His Phe Thr Ser Tyr Trp Met His
1               5                   10

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Val Ile His Pro Asn Ser Gly Ser Ile Asn Tyr Asn Glu Lys Phe Glu
```

Ser

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Glu Arg Asp Ser Thr Glu Val Leu Pro Met Asp Tyr
1               5                   10

<210> SEQ ID NO 26
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
caggtgcagc tggtgcagtc aggggctgag ctgaagaagc ctggggcttc agtgaaggtt      60
tcctgcaagt cttctggcta ccatttcacc agctactgga tgcactgggt gaagcaggcc     120
cctggacaag gccttgagtg gattggagtg attcatccta atagtggtag tattaactac     180
aatgagaagt tcgagagcaa ggccacaatt actgtagaca atccaccag cacagcctac      240 atgcaactca gcagcctgac atctgaggac tcggcggtct attattgtgc aggagagaga     300
gattctacgg aggttctccc tatggactac tggggtcaag aacctcagt caccgtctcc      360 tca                                                                   363

<210> SEQ ID NO 27
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
caggtgcagc tggtgcagtc aggggctgag ctgaagaagc ctggggcttc agtgaaggtt      60
tcctgcaagt cttctggcta ccatttcacc agctactgga tgcactgggt gaagcaggcc     120
cctggacaag gccttgagtg gattggagtg attcatccta atagtggtag tattaactac     180
aatgagaagt tcgagagcag agccacaatt actgtagaca atccaccag cacagcctac      240 atggagctca gcagcctgag atctgaggac acggcggtct attattgtgc aggagagaga     300
gattctacgg aggttctccc tatggactac tggggtcaag aaccacggt caccgtctcc      360 tca                                                                   363

<210> SEQ ID NO 28
<211> LENGTH: 364
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

```
caggtgcagc tggtgcagtc aggggctgag ctgaagaagc ctggggcttc agtgaaggtt      60
tcctgcaagt cttctggcta ccatttcacc agctactgga tgcactgggt gaagcaggcc    120
cctggacaag gccttgagtg gattggagtg attcatccta atagtggtag tattaactac    180
aatgagaagt tcgagagcag agtcacaatt actgtagaca atccaccag cacagcctac     240 atggagctca gcagcctgag atctgaggac acggcggtct attattgtgc aggagagaga    300
gattctacgg aggttctccc tatggactac tggggtcaag gaaccacggt caccgtctcc    360
tcag                                                                 364

<210> SEQ ID NO 29
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
caggtgcagc tggtgcagtc aggggctgag ctgaagaagc ctggggcttc agtgaaggtt      60
tcctgcaagt cttctggcta ccatttcacc agctactgga tgcactgggt gcgacaggcc    120
cctggacaag gccttgagtg gattggagtg attcatccta atagtggtag tattaactac    180
aatgagaagt tcgagagcag agtcacaatt actgtagaca atccaccag cacagcctac     240 atggagctca gcagcctgag atctgaggac acggcggtct attattgtgc aggagagaga    300
gattctacgg aggttctccc tatggactac tggggtcaag gaaccacggt caccgtctcc    360
tca                                                                  363

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Ala Ser Lys Ser Ile Asn Lys Tyr Leu Ala
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Gly Ser Thr Leu Gln Ser
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Gln His Asn Glu Tyr Pro Leu Thr
```

<210> SEQ ID NO 33
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
gatgtccaga tcacacagtc tccatcttat cttgctgcat ctctcggaga aagagctact    60
attaattgca gggcaagtaa gagcattaac aaatacttag cctggtatca acagaaacct   120
gggaaaacta ataagctcct tatctactct ggctccactt tgcaatctgg aattccagca   180
aggttcagtg gcagtggatc tggtacagat ttcactctca ccatcagtag cctggagcct   240
gaagattttg caatgtatta ctgtcaacaa cataatgaat acccgctcac gttcggtcag   300
gggaccaagc tggagatcaa a                                             321

<210> SEQ ID NO 34
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
gatgtccaga tcacacagtc tccatcttcc ctttctgcat ctctcggaga aagagctact    60
attaattgca gggcaagtaa gagcattaac aaatacttag cctggtatca acagaaacct   120
gggaaagcta ataagctcct tatctactct ggctccactt tgcaatctgg aattccagca   180
aggttcagtg gcagtggatc tggtacagat ttcactctca ccatcagtag cctggagcct   240
gaagattttg caatgtatta ctgtcaacaa cataatgaat acccgctcac gttcggtcag   300
gggaccaagc tggagatcaa a                                             321

<210> SEQ ID NO 35
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
gatgtccaga tcacacagtc tccatcttcc ctttctgcat ctctcggaga aagagctact    60
attaattgca gggcaagtaa gagcattaac aaatacttag cctggtatca acagaaacct   120
gggaaagctc ctaagctcct tatctactct ggctccactt tgcaatctgg aattccagca   180
aggttcagtg gcagtggatc tggtacagat ttcactctca ccatcagtag cctggagcct   240
gaagattttg caatgtatta ctgtcaacaa cataatgaat acccgctcac gttcggtcag   300
gggaccaagc tggagatcaa a                                             321

<210> SEQ ID NO 36
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

```
gatattcagc tcacacagtc tccatcttcc ctttctgcat ctctcggaga aagagctact    60
attaattgca gggcaagtaa gagcattaac aaatacttag cctggtatca acagaaacct   120
gggaaagctc ctaagctcct tatctactct ggctccactt tgcaatctgg aattccagca   180
aggttcagtg gcagtggatc tggtacagat ttcactctca ccatcagtag cctggagcct   240
gaagattttg caatgtatta ctgtcaacaa cataatgaat acccgctcac gttcggtcag   300
gggaccaagc tggagatcaa a                                             321
```

<210> SEQ ID NO 37
<211> LENGTH: 327
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285
```

```
Arg Leu Thr Val Asp Lys Ser Arg Trp Gln Glu Gly Asn Val Phe Ser
        290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 38
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Glu Ser Lys Tyr Gly Pro Pro Cys Pro Pro Cys Pro
1               5                   10

<210> SEQ ID NO 40
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Ala Pro Glu Phe Glu Gly Gly Pro Ser Val Phe Leu Phe Pro Pro Lys
1               5                   10                  15
Pro Lys Asp Thr Leu Met Ile Ser Arg Thr Pro Glu Val Thr Cys Val
            20                  25                  30
Val Val Asp Val Ser Gln Glu Asp Pro Glu Val Gln Phe Asn Trp Tyr
        35                  40                  45
Val Asp Gly Val Glu Val His Asn Ala Lys Thr Lys Pro Arg Glu Glu
    50                  55                  60
Gln Phe Asn Ser Thr Tyr Arg Val Val Ser Val Leu Thr Val Leu His
```

```
                65                  70                  75                  80
Gln Asp Trp Leu Asn Gly Lys Glu Tyr Lys Cys Lys Val Ser Asn Lys
                    85                  90                  95

Gly Leu Pro Ser Ser Ile Glu Lys Thr Ile Ser Lys Ala Lys
                100                 105                 110

<210> SEQ ID NO 41
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
                100                 105

<210> SEQ ID NO 42
<211> LENGTH: 1805
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
gtaagctttc tgggcaggc cgggcctgac tttggctggg ggcagggagg gggctaaggt    60
gacgcaggtg gcgccagcca ggtgcacacc caatgcccat gagcccagac actgaccct   120 gcatggacca tcgcggatag acaagaaccg aggggcctct gcgccctggg cccagctctg   180
tcccacaccg cggtcacatg gcaccactc tcttgcagct tccaccaagg gcccatccgt   240 cttcccctg gcgccctgct ccaggagcac ctccgagagc acagccgccc tgggctgcct   300
ggtcaaggac tacttccccg aaccggtgac ggtgtcgtgg aactcaggcg ccctgaccag   360
cggcgtgcac accttcccgg ctgtcctaca gtcctcagga ctctactccc tcagcagcgt   420
ggtgaccgtg ccctccagca gcttgggcac gaagacctac acctgcaatg tagatcacaa   480
gcccagcaac accaaggtgg acaagagagt tggtgagagg ccagcacagg gagggagggt   540
gtctgctgga agccaggctc agccctcctg cctggacgca cccggctgt gcagccccag   600 cccagggcag caaggcaggc cccatctgtc tcctcacctg gaggcctctg accacccca   660 tcatgctcag ggagagggtc ttctggattt ttccaccagg ctccgggcag ccacaggctg   720
gatgccccta cccaggccc tgcgcataca ggggcaggtg ctgcgctcag acctgccaag   780
agccatatcc gggaggaccc tgcccctgac ctaagcccac ccaaaggcc aaactctcca   840
```

```
ctccctcagc tcagacacct tctctcctcc cagatctgag taactcccaa tcttctctct    900
gcagagtcca aatatggtcc cccatgccca ccatgcccag gtaagccaac ccaggcctcg    960
ccctccagct caaggcggga caggtgccct agagtagcct gcatccaggg acaggcccca   1020
gccgggtgct gacgcatcca cctccatctc ttcctcagca cctgagttcg aggggggacc   1080
atcagtcttc ctgttccccc caaaacccaa ggacactctc atgatctccc ggacccctga   1140
ggtcacgtgc gtggtggtgg acgtgagcca ggaagacccc gaggtccagt tcaactggta   1200
cgtggatggc gtggaggtgc ataatgccaa gacaaagccg cgggaggagc agttcaacag   1260
cacgtaccgt gtggtcagcg tcctcaccgt cctgcaccag gactggctga acggcaagga   1320
gtacaagtgc aaggtctcca acaaaggcct cccgtcctcc atcgagaaaa ccatctccaa   1380
agccaaaggt gggacccacg gggtgcgagg gccacatgga cagaggtcag ctcggcccac   1440
cctctgccct gggagtgacc gctgtgccaa cctctgtccc tacagggcag ccccgagagc   1500
cacaggtgta caccctgccc ccatcccagg aggagatgac caagaaccag gtcagcctga   1560
cctgcctggt caaaggcttc taccccagcg acatcgccgt ggagtgggag agcaatgggc   1620
agccggagaa caactacaag accacgcctc ccgtgctgga ctccgacggc tccttcttcc   1680
tctacagcag gctaaccgtg gacaagagca ggtggcagga ggggaatgtc ttctcatgct   1740
ccgtgatgca tgaggctctg cacaaccact acacacagaa gagcctctcc ctgtctctgg   1800
gtaaa                                                               1805
```

<210> SEQ ID NO 43
<211> LENGTH: 294
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 43

```
cttccaccaa gggcccatcc gtcttccccc tggcgccctg ctccaggagc acctccgaga     60
gcacagccgc cctgggctgc ctggtcaagg actacttccc cgaaccggtg acggtgtcgt    120
ggaactcagg cgccctgacc agcggcgtgc acaccttccc ggctgtccta cagtcctcag    180
gactctactc cctcagcagc gtggtgaccg tgccctccag cagcttgggc acgaagacct    240
acacctgcaa tgtagatcac aagcccagca acaccaaggt ggacaagaga gttg          294
```

<210> SEQ ID NO 44
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 44

```
agtccaaata tggtccccca tgcccaccat gcccag                               36
```

<210> SEQ ID NO 45
<211> LENGTH: 330
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 45

-continued

```
cacctgagtt cgagggggga ccatcagtct tcctgttccc cccaaaaccc aaggacactc      60
tcatgatctc ccggacccct gaggtcacgt gcgtggtggt ggacgtgagc caggaagacc     120
ccgaggtcca gttcaactgg tacgtggatg gcgtggaggt gcataatgcc aagacaaagc    180
cgcgggagga gcagttcaac agcacgtacc gtgtggtcag cgtcctcacc gtcctgcacc    240
aggactggct gaacggcaag gagtacaagt gcaaggtctc caacaaaggc ctcccgtcct    300
ccatcgagaa aaccatctcc aaagccaaag                                      330
```

<210> SEQ ID NO 46
<211> LENGTH: 320
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 46

```
ggcagcccccg agagccacag gtgtacaccc tgcccccatc ccaggaggag atgaccaaga     60
accaggtcag cctgacctgc ctggtcaaag gcttctaccc cagcgacatc gccgtggagt    120
gggagagcaa tgggcagccg gagaacaact acaagaccac gcctcccgtg ctggactccg    180
acggctcctt cttcctctac agcaggctaa ccgtggacaa gagcaggtgg caggagggga    240
atgtcttctc atgctccgtg atgcatgagg ctctgcacaa ccactacaca cagaagagcc    300
tctccctgtc tctgggtaaa                                                 320
```

HUMANIZED ANTI-COMPLEMENT FACTOR C1Q ANTIBODIES

RELATED APPLICATIONS

This application claims the benefit of U.S. Provisional Application 62/075,793, filed Nov. 5, 2014, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Jan. 22, 2016, is named ANH-008.01_SL.txt and is 37,851 bytes in size.

BACKGROUND

1. Field

The present disclosure relates to anti-C1q antibodies and methods of using them.

2. Description of Related Art

Excessive complement activation has been associated with a range of disease conditions, including numerous inflammatory and autoimmune diseases. More recently, the complement system has also been shown to contribute to neurodegenerative disease pathology. Specifically, complement factors, such as C1q, were shown to be expressed in neuronal synapses and to mark these synapses for elimination. See, e.g., U.S. Patent Publication Nos. 2012/0195880 and 2012/328601. While selective synapse loss is an essential aspect of normal brain development ("synaptic pruning"), excessive synapse loss, especially in a mature or aging brain, results in neurodegeneration and cognitive decline. Elevated synaptic complement expression was found to contribute to synaptic loss in normal aging and in neurodegenerative disease progression. Conversely, lowering neuronal complement expression was found to be neuroprotective. Based on these findings, neutralizing the activity of complement factors such as C1q is regarded as a promising therapeutic strategy to prevent synapse loss and to slow neurodegenerative disease progression as well as cognitive decline in normal aging.

Neurodegenerative diseases involving synapse loss and considered to be amenable to treatments aiming at the neutralization of complement factors such as C1q include Alzheimer's disease, amyotrophic lateral sclerosis, multiple sclerosis, glaucoma, myotonic dystrophy, Down syndrome, Parkinson's disease, Huntington's disease, and the like.

Only a limited number of complement neutralizing antibodies are known to date (see, e.g., Klos A. et al., *Mol Immunol.* 2009, 46(14), 2753-2766; Carroll S. & Georgiou G., *Immunobiology* 2013, 218(8), 1041-1048; Tuzun et al., *J. Neuroimmunol.* 2007, 182, 167-176; Nelson et al., *J. Clin. Invest.* 2006, 116:2892-2900; Heinz et al., *J. Immunol.* 1984, 133, 400-404; Jiang et al., *J. Immunol.* 1991, 146, 2324-2330; Trinder et al., *Scand. J. Immunol.* 1999, 50, 635-641; Hwang et al., *Mol. Immunol.* 2008, 45, 2570-2580). Only the C5 neutralizing antibody Eculizumab, an inhibitor of the terminal complement activation pathway, has obtained regulatory approval to date; Eculizumab is marketed for the treatment of paroxysmal nocturnal hemoglobinuria (PNH; Hillmen et al., *N Engl J Med.* 2006, 355(12):1233-43).

Thus, there is a need to develop further antibodies that specifically bind to and neutralize biological activities of complement factors such as C1q.

All references cited herein, including patent applications and publications, are hereby incorporated by reference in their entirety.

BRIEF SUMMARY

Provided herein are humanized anti-C1q antibodies and methods of using humanized anti-C1q antibodies.

In certain aspects, the present disclosure provides a humanized antibody that specifically binds to a C1q protein, wherein the antibody comprises a heavy chain variable region and a human heavy chain constant region, wherein the heavy chain variable region comprises an Fab region and the heavy chain constant region comprises an Fc region, wherein the Fab region specifically binds to the C1q protein, and wherein the Fc region is incapable of binding the C1q protein.

In some embodiments that may be combined with any of the preceding embodiments, the Fc region is incapable of inducing complement activity. In some embodiments that may be combined with any of the preceding embodiments, the Fc region is incapable of inducing antibody-dependent cellular cytotoxicity (ADCC). In some embodiments that may be combined with any of the preceding embodiments, the human heavy chain constant region is a human IgG4 heavy chain constant region. In some embodiments that may be combined with any of the preceding embodiments, the human IgG4 heavy chain constant region comprises the amino acid sequence of SEQ ID NO: 37, or an amino acid sequence with at least about 90% homology to the amino acid sequence of SEQ ID NO: 37. In some embodiments that may be combined with any of the preceding embodiments, the human IgG4 heavy chain constant region comprises an Fc region, and wherein the Fc region comprises one or more modifications. In some embodiments that may be combined with any of the preceding embodiments, the Fc region comprises one or more amino acid substitutions. In some embodiments that may be combined with any of the preceding embodiments, the Fc region comprises an amino acid substitution at position 248 according to Kabat numbering convention. In some embodiments that may be combined with any of the preceding embodiments, the Fc region comprises a leucine to glutamate amino acid substitution at position 248 according to Kabat numbering convention. In some embodiments that may be combined with any of the preceding embodiments, the amino acid substitution at position 248 according to Kabat numbering convention inhibits the Fc region from interacting with an Fc receptor. In some embodiments that may be combined with any of the preceding embodiments, the Fc region comprises an amino acid substitution at position 241 according to Kabat numbering convention. In some embodiments that may be combined with any of the preceding embodiments, the Fc region comprises a serine to proline amino acid substitution at position 241 according to Kabat numbering convention. In some embodiments that may be combined with any of the preceding embodiments, the amino acid substitution at position 241 according to Kabat numbering convention prevents arm switching in the antibody. In some embodiments that may be combined with any of the preceding embodiments, the antibody comprises, the Fc region comprises the amino acid sequence of SEQ ID NO: 37, or an amino acid sequence with at least about 70%, at least about 75%, at least about 80% at least about 85% at least about 90%, or at least about 90% homology to the amino acid sequence of SEQ ID NO: 37. In some embodiments that may be combined with any of the preceding embodiments, the antibody comprises a heavy chain variable domain and a light chain variable domain, wherein the heavy chain variable domain comprises an amino acid sequence selected from SEQ ID NOs: 1-4, or an amino acid sequence with at least about 90% homology to the amino acid sequence selected from SEQ ID NOs: 1-4. In some embodiments that may be combined with any of the preceding embodiments, the light chain variable domain comprises an amino acid sequence selected from SEQ ID NOs: 5-8, or an amino acid sequence with at least about 90% homology to the amino acid sequence selected from SEQ ID NOs: 5-8.

In certain aspects, the present disclosure provides a humanized anti-C1q antibody, or an antigen-binding fragment thereof, the antibody comprising a heavy chain variable domain and a light chain variable domain, wherein the heavy chain variable domain comprises an amino acid sequence selected from SEQ ID NOs: 1-4, or an amino acid sequence with at least about 90% homology to the amino acid sequence selected from SEQ ID NOs: 1-4.

In certain aspects, the present disclosure provides a humanized anti-C1q antibody, or an antigen-binding fragment thereof, the antibody comprising a heavy chain variable domain and a light chain variable domain, wherein the light chain variable domain comprises an amino acid sequence selected from SEQ ID NOs: 5-8, or an amino acid sequence with at least about 90% homology to the amino acid sequence selected from SEQ ID NOs: 5-8.

In certain aspects, the present disclosure provides a humanized anti-C1q antibody, or an antigen-binding fragment thereof, the antibody comprising: a) a heavy chain variable domain comprising an amino acid sequence selected from SEQ ID NOs: 1-4, or an amino acid sequence with at least about 90% homology to the amino acid sequence selected from SEQ ID NOs: 1-4; and/or b) a light chain variable domain comprising an amino acid sequence selected from SEQ ID NOs: 5-8, or an amino acid sequence with at least about 90% homology to the amino acid sequence selected from SEQ ID NOs: 5-8.

In certain aspects, the present disclosure provides a humanized anti-C1q antibody, or an antigen-binding fragment thereof, the antibody comprising: a) a heavy chain variable domain comprising the amino acid sequence of SEQ ID NO: 1, or an amino acid sequence with at least about 90% homology to the amino acid sequence of SEQ ID NO: 1; and b) a light chain variable domain comprising an amino acid sequence selected from SEQ ID NOs: 5-8, or an amino acid sequence with at least about 90% homology to the amino acid sequence selected from SEQ ID NOs: 5-8. In certain aspects, the present disclosure provides a humanized anti-C1q antibody, or an antigen-binding fragment thereof, the antibody comprising: a) a heavy chain variable domain comprising the amino acid sequence of SEQ ID NO: 2, or an amino acid sequence with at least about 90% homology to the amino acid sequence of SEQ ID NO: 2; and b) a light chain variable domain comprising an amino acid sequence selected from SEQ ID NOs: 5-8, or an amino acid sequence with at least about 90% homology to the amino acid sequence selected from SEQ ID NOs: 5-8. In certain aspects, the present disclosure provides a humanized anti-C1q antibody, or an antigen-binding fragment thereof, the antibody comprising: a) a heavy chain variable domain comprising the amino acid sequence of SEQ ID NO: 3, or an amino acid sequence with at least about 90% homology to the amino acid sequence of SEQ ID NO: 3; and b) a light chain variable domain comprising an amino acid sequence selected from SEQ ID NOs: 5-8, or an amino acid sequence with at least about 90% homology to the amino acid sequence selected from SEQ ID NOs: 5-8. In certain aspects, the present disclosure provides a humanized anti-C1q antibody, or an antigen-binding fragment thereof, the antibody comprising: a) a heavy chain variable domain comprising the amino acid sequence of SEQ ID NO: 4, or an amino acid sequence with at least about 90% homology to the amino acid sequence of SEQ ID NO: 4; and b) a light chain variable domain comprising an amino acid sequence selected from SEQ ID NOs: 5-8, or an amino acid sequence with at least about 90% homology to the amino acid sequence selected from SEQ ID NOs: 5-8.

In certain aspects, the present disclosure provides a humanized anti-C1q antibody, or an antigen-binding fragment thereof, the antibody comprising: a) a heavy chain variable domain comprising an amino acid sequence selected from SEQ ID NOs: 1-4, or an amino acid sequence with at least about 90% homology to the amino acid sequence selected from SEQ ID NOs: 1-4; and b) a light chain variable domain comprising the amino acid sequence of SEQ ID NO: 5, or an amino acid sequence with at least about 90% homology to the amino acid sequence of SEQ ID NO: 5. In certain aspects, the present disclosure provides a humanized anti-C1q antibody, or an antigen-binding fragment thereof, the antibody comprising: a) a heavy chain variable domain comprising an amino acid sequence selected from SEQ ID NOs: 1-4, or an amino acid sequence with at least about 90% homology to the amino acid sequence selected from SEQ ID NOs: 1-4; and b) a light chain variable domain comprising the amino acid sequence of SEQ ID NO: 6, or an amino acid sequence with at least about 90% homology to the amino acid sequence of SEQ ID NO: 6. In certain aspects, the present disclosure provides a humanized anti-C1q antibody, or an antigen-binding fragment thereof, the antibody comprising: a) a heavy chain variable domain comprising an amino acid sequence selected from SEQ ID NOs: 1-4, or an amino acid sequence with at least about 90% homology to the amino acid sequence selected from SEQ ID NOs: 1-4; and b) a light chain variable domain comprising the amino acid sequence of SEQ ID NO: 7, or an amino acid sequence with at least about 90% homology to the amino acid sequence of SEQ ID NO: 7. In certain aspects, the present disclosure provides a humanized anti-C1q antibody, or an antigen-binding fragment thereof, the antibody comprising: a) a heavy chain variable domain comprising an amino acid sequence selected from SEQ ID NOs: 1-4, or an amino acid sequence with at least about 90% homology to the amino acid sequence selected from SEQ ID NOs: 1-4; and b) a light chain variable domain comprising the amino acid sequence of SEQ ID NO: 8, or an amino acid sequence with at least about 90% homology to the amino acid sequence of SEQ ID NO: 8.

In certain aspects, the present disclosure provides a humanized anti-C1q antibody, or an antigen-binding fragment thereof, the antibody comprising: a) a heavy chain variable domain comprising the amino acid sequence of SEQ ID NO: 1, or an amino acid sequence with at least about 90% homology to the amino acid sequence of SEQ ID NO: 1; and b) a light chain variable domain comprising the amino acid sequence of SEQ ID NO: 5, or an amino acid sequence with at least about 90% homology to the amino acid sequence of SEQ ID NO: 5. In certain aspects, the present disclosure provides a humanized anti-C1q antibody, or an antigen-binding fragment thereof, the antibody comprising: a) a heavy chain variable domain comprising the amino acid sequence of SEQ ID NO: 1, or an amino acid sequence with at least about 90% homology to the amino acid sequence of SEQ ID NO: 1; and b) a light chain variable domain comprising the amino acid sequence of SEQ ID NO: 6, or an amino acid sequence with at least about 90% homology to the amino acid sequence of SEQ ID NO: 6. In certain aspects, the present disclosure provides a humanized anti-C1q antibody, or an antigen-binding fragment thereof, the antibody comprising: a) a heavy chain variable domain comprising the amino acid sequence of SEQ ID NO: 1, or an amino acid sequence with at least about 90% homology to the amino acid sequence of SEQ ID NO: 1; and b) a light chain variable domain comprising the amino acid sequence of SEQ ID NO: 7, or an amino acid sequence with at least about 90% homology to the amino acid sequence of SEQ ID NO: 7. In certain aspects, the present disclosure provides a humanized anti-C1q antibody, or an antigen-binding fragment thereof, the antibody comprising: a) a heavy chain variable domain comprising the amino acid sequence of SEQ ID NO: 1, or an amino acid sequence with at least about 90% homology to the amino acid sequence of SEQ ID NO: 1; and b) a light chain variable domain comprising the amino acid sequence of SEQ ID NO: 8, or an amino acid sequence with at least about 90% homology to the amino acid sequence of SEQ ID NO: 8.

In certain aspects, the present disclosure provides a humanized anti-C1q antibody, or an antigen-binding fragment thereof, the antibody comprising: a) a heavy chain variable domain comprising the amino acid sequence of SEQ ID NO: 2, or an amino acid sequence with at least about 90% homology to the amino acid sequence of SEQ ID NO: 2; and b) a light chain variable domain comprising the amino acid sequence of SEQ ID NO: 5, or an amino acid sequence with at least about 90% homology to the amino acid sequence of SEQ ID NO: 5. In certain aspects, the present disclosure provides a humanized anti-C1q antibody, or an antigen-binding fragment thereof, the antibody comprising: a) a heavy chain variable domain comprising the amino acid sequence of SEQ ID NO: 2, or an amino acid sequence with at least about 90% homology to the amino acid sequence of SEQ ID NO: 2; and b) a light chain variable domain comprising the amino acid sequence of SEQ ID NO: 6, or an amino acid sequence with at least about 90% homology to the amino acid sequence of SEQ ID NO: 6. In certain aspects, the present disclosure provides a humanized anti-C1q antibody, or an antigen-binding fragment thereof, the antibody comprising: a) a heavy chain variable domain comprising the amino acid sequence of SEQ ID NO: 2, or an amino acid sequence with at least about 90% homology to the amino acid sequence of SEQ ID NO: 2; and b) a light chain variable domain comprising the amino acid sequence of SEQ ID NO: 7, or an amino acid sequence with at least about 90% homology to the amino acid sequence of SEQ ID NO: 7. In certain aspects, the present disclosure provides a humanized anti-C1q antibody, or an antigen-binding fragment thereof, the antibody comprising: a) a heavy chain variable domain comprising the amino acid sequence of SEQ ID NO: 2, or an amino acid sequence with at least about 90% homology to the amino acid sequence of SEQ ID NO: 2; and b) a light chain variable domain comprising the amino acid sequence of SEQ ID NO: 8, or an amino acid sequence with at least about 90% homology to the amino acid sequence of SEQ ID NO: 8.

In certain aspects, the present disclosure provides a humanized anti-C1q antibody, or an antigen-binding fragment thereof, the antibody comprising: a) a heavy chain variable domain comprising the amino acid sequence of SEQ ID NO: 3, or an amino acid sequence with at least about 90% homology to the amino acid sequence of SEQ ID NO: 3; and b) a light chain variable domain comprising the amino acid sequence of SEQ ID NO: 5, or an amino acid sequence with at least about 90% homology to the amino acid sequence of SEQ ID NO: 5. In certain aspects, the present disclosure provides a humanized anti-C1q antibody, or an antigen-binding fragment thereof, the antibody comprising: a) a heavy chain variable domain comprising the amino acid sequence of SEQ ID NO: 3, or an amino acid sequence with at least about 90% homology to the amino acid sequence of SEQ ID NO: 3; and b) a light chain variable domain comprising the amino acid sequence of SEQ ID NO: 6, or an amino acid sequence with at least about 90% homology to the amino acid sequence of SEQ ID NO: 6. In certain aspects, the present disclosure provides a humanized anti-C1q antibody, or an antigen-binding fragment thereof, the antibody comprising: a) a heavy chain variable domain comprising the amino acid sequence of SEQ ID NO: 3, or an amino acid sequence with at least about 90% homology to the amino acid sequence of SEQ ID NO: 3; and b) a light chain variable domain comprising the amino acid sequence of SEQ ID NO: 7, or an amino acid sequence with at least about 90% homology to the amino acid sequence of SEQ ID NO: 7. In certain aspects, the present disclosure provides a humanized anti-C1q antibody, or an antigen-binding fragment thereof, the antibody comprising: a) a heavy chain variable domain comprising the amino acid sequence of SEQ ID NO: 3, or an amino acid sequence with at least about 90% homology to the amino acid sequence of SEQ ID NO: 3; and b) a light chain variable domain comprising the amino acid sequence of SEQ ID NO: 8, or an amino acid sequence with at least about 90% homology to the amino acid sequence of SEQ ID NO: 8.

In certain aspects, the present disclosure provides a humanized anti-C1q antibody, or an antigen-binding fragment thereof, the antibody comprising: a) a heavy chain variable domain comprising the amino acid sequence of SEQ ID NO: 4, or an amino acid sequence with at least about 90% homology to the amino acid sequence of SEQ ID NO: 4; and b) a light chain variable domain comprising the amino acid sequence of SEQ ID NO: 5, or an amino acid sequence with at least about 90% homology to the amino acid sequence of SEQ ID NO: 5. In certain aspects, the present disclosure provides a humanized anti-C1q antibody, or an antigen-binding fragment thereof, the antibody comprising: a) a heavy chain variable domain comprising the amino acid sequence of SEQ ID NO: 4, or an amino acid sequence with at least about 90% homology to the amino acid sequence of SEQ ID NO: 4; and b) a light chain variable domain comprising the amino acid sequence of SEQ ID NO: 6, or an amino acid sequence with at least about 90% homology to the amino acid sequence of SEQ ID NO: 6. In certain aspects, the present disclosure provides a humanized anti-C1q antibody, or an antigen-binding fragment thereof, the antibody comprising: a) a heavy chain variable domain comprising the amino acid sequence of SEQ ID NO: 4, or an amino acid sequence with at least about 90% homology to the amino acid sequence of SEQ ID NO: 4; and b) a light chain variable domain comprising the amino acid sequence of SEQ ID NO: 7, or an amino acid sequence with at least about 90% homology to the amino acid sequence of SEQ ID NO: 7. In certain aspects, the present disclosure provides a humanized anti-C1q antibody, or an antigen-binding fragment thereof, the antibody comprising: a) a heavy chain variable domain comprising the amino acid sequence of SEQ ID NO: 4, or an amino acid sequence with at least about 90% homology to the amino acid sequence of SEQ ID NO: 4; and b) a light chain variable domain comprising the amino acid sequence of SEQ ID NO: 8, or an amino acid sequence with at least about 90% homology to the amino acid sequence of SEQ ID NO: 8.

In some embodiments that may be combined with any of the preceding embodiments, the antibody binds specifically to both human C1q and mouse C1q. In some embodiments that may be combined with any of the preceding embodiments, the antibody binds specifically to rat C1q. In some embodiments that may be combined with any of the preceding embodiments, the antibody binds specifically to human C1q, mouse C1q, and rat C1q. In some embodiments that may be combined with any of the preceding embodiments, the antibody or antigen-binding fragment thereof binds essentially the same C1q epitope as the antibody M1 produced by the hybridoma cell line with ATCC Accession Number PTA-120399 or anti-C1q binding fragments thereof. In some embodiments that may be combined with any of the preceding embodiments, the antibody or antigen-binding fragment thereof inhibits the binding of the monoclonal antibody M1 produced by a hybridoma cell line with ATCC Accession Number PTA-120399 to human C1q or to mouse C1q. In some embodiments that may be combined with any of the preceding embodiments, the antibody is of the IgG class. In some embodiments that may be combined with any of the preceding embodiments, the antibody has an IgG1, IgG2, IgG3, or IgG4 isotype. In some embodiments that may be combined with any of the preceding embodiments, the antibody has an IgG4 isotype. In some embodiments that may be combined with any of the preceding embodiments, the antibody comprises a human IgG4 constant region. In some embodiments that may be combined with any of the preceding embodiments, the human IgG4 heavy chain constant region comprises the amino acid sequence of SEQ ID NO: 37, or an amino acid sequence with at least about 90% homology to the amino acid sequence of SEQ ID NO: 37. In some embodiments that may be combined with any of the preceding embodiments, the human IgG4 constant region comprises an Fc region. In some embodiments that may be combined with any of the preceding embodiments, the Fc region is incapable of binding the C1q protein. In some embodiments that may be combined with any of the preceding embodiments, the Fc region is incapable of inducing complement activity. In some embodiments that may be combined with any of the preceding embodiments, the Fc region is incapable of inducing antibody-dependent cellular cytotoxicity (ADCC). In some embodiments that may be combined with any of the preceding embodiments, the Fc region comprises one or more modifications. In some embodiments that may be combined with any of the preceding embodiments, the Fc region comprises one or more amino acid substitutions. In some embodiments that may be combined with any of the preceding embodiments, the Fc region comprises an amino acid substitution at position 248 according to Kabat numbering convention. In some embodiments that may be combined with any of the preceding embodiments, the Fc region comprises a leucine to glutamate amino acid substitution at position 248 according to Kabat numbering convention. In some embodiments that may be combined with any of the preceding embodiments, the amino acid substitution at position 248 according to Kabat numbering convention inhibits the Fc region from interacting with an Fc receptor. In some embodiments that may be combined with any of the preceding embodiments, the Fc region comprises an amino acid substitution at position 241 according to Kabat numbering convention. In some embodiments that may be combined with any of the preceding embodiments, the Fc region comprises a serine to proline amino acid substitution at position 241 according to Kabat numbering convention. In some embodiments that may be combined with any of the preceding embodiments, the amino acid substitution at position 241 according to Kabat numbering convention prevents arm switching in the antibody. In some embodiments that may be combined with any of the preceding embodiments, the antibody is a bispecific antibody. In some embodiments that may be combined with any of the preceding embodiments, the antibody has been engineered to increase brain penetration. In some embodiments that may be combined with any of the preceding embodiments, the antibody is a bispecific antibody recognizing a first antigen and a second antigen. In some embodiments that may be combined with any of the preceding embodiments, the first antigen is a C1q protein and the second antigen is an antigen facilitating transport across the blood-brain-barrier. In some embodiments that may be combined with any of the preceding embodiments, the second antigen is selected from transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopep peptide, and ANG1005. In some embodiments that may be combined with any of the preceding embodiments, the antigen-binding fragment is a Fab, F(ab')$_2$ or Fab' fragment. In some embodiments that may be combined with any of the preceding embodiments, the antibody fragment has better brain penetration as compared to its corresponding full-length antibody. In some embodiments that may be combined with any of the preceding embodiments, the antibody fragment has a shorter half-life as compared to its corresponding full-length antibody. In some embodiments that may be combined with any of the preceding embodiments, the antibody has a dissociation constant ($K_D$) for human C1q that ranges from less than about 10 pM to less than about 5 pM. In some embodiments that may be combined with any of the preceding embodiments, the antibody has dissociation constant ($K_D$) for mouse C1q that ranges from less than about 125 nM to less than about 5 pM. In some embodiments that may be combined with any of the preceding embodiments, the antibody specifically binds to and neutralizes a biological activity of C1q. In some embodiments that may be combined with any of the preceding embodiments, the biological activity is (1) C1q binding to an autoantibody, (2) C1q binding to C1r, (3) C1q binding to C1s, (4) C1q binding to phosphatidylserine, (5) C1q binding to pentraxin-3, (6) C1q binding to C-reactive protein (CRP), (7) C1q binding to globular C1q receptor (gC1qR), (8) C1q binding to complement receptor 1 (CR1), (9) C1q binding to beta-amyloid, or (10) C1q binding to calreticulin. In some embodiments that may be combined with any of the preceding embodiments, the biological activity is (1) activation of the classical complement activation pathway, (2) activation of antibody and complement dependent cytotoxicity, (3) CH50 hemolysis, (4) synapse loss, (5) B-cell antibody production, (6) dendritic cell maturation, (7) T-cell proliferation, (8) cytokine production (9) microglia activation, (10) Arthus reaction, (11) phagocytosis of synapses or nerve endings, or (12) activation of complement receptor 3 (CR3/C3) expressing cells. In some embodiments that may be combined with any of the preceding embodiments, CH50 hemolysis comprises human, mouse, and/or rat CH50 hemolysis. In some embodiments that may be combined with any of the preceding embodiments, the antibody is capable of neutralizing from at least about 50%, to at least about 95% of CH50 hemolysis. In some embodiments that may be combined with any of the preceding embodiments, the antibody is capable of neutralizing at least 50% of CH50 hemolysis at a dose of less than 150 ng, less than 100 ng, less than 50 ng, or less than 20 ng. In some embodiments that may be combined with any of the preceding embodiments, the antibody binds C1q with a binding stoichiometry that ranges from 20:1 to 1.0:1 or less than 1.0:1.

In certain aspects, the present disclosure provides an isolated polynucleotide comprising a nucleic acid sequence encoding a humanized anti-C1q antibody of any of the preceding embodiments. In certain aspects, the present disclosure provides an isolated host cell comprising a nucleic acid sequence of any of the preceding embodiments. In certain aspects, the present disclosure provides a pharmaceutical composition comprising a humanized anti-C1q antibody of any of the preceding embodiments and a pharmaceutically acceptable carrier.

In certain aspects, the present disclosure provides a method of treating or preventing a disease associated with complement activation in an individual in need of such treatment, the method comprising the step of administering a therapeutically effective dose of a humanized anti-C1q antibody of any of the preceding embodiments. In other aspects, the present disclosure provides a humanized anti-C1q antibody of any of the preceding embodiments for use in treating or preventing a disease associated with complement activation in an individual in need of such treatment. In other aspects, the present disclosure provides use of a humanized anti-C1q antibody of any of the preceding embodiments in the manufacture of a medicament for treating or preventing a disease associated with complement activation in an individual in need of such treatment.

In some embodiments that may be combined with any of the preceding embodiments, the disease associated with complement activation is a neurodegenerative disorder. In some embodiments that may be combined with any of the preceding embodiments, the neurodegenerative disorder is associated with the loss of synapses or nerve connections. In some embodiments that may be combined with any of the preceding embodiments, the neurodegenerative disorder is associated with synapse loss that is dependent on the complement receptor 3(CR3)/C3 or complement receptor CR1. In some embodiments that may be combined with any of the preceding embodiments, the neurodegenerative disorder is associated with pathological activity-dependent synaptic pruning. In some embodiments that may be combined with any of the preceding embodiments, the neurodegenerative disorder is associated with synapse phagocytosis by microglia. In some embodiments that may be combined with any of the preceding embodiments, the neurodegenerative disorder is selected from Alzheimer's disease, amyotrophic lateral sclerosis, multiple sclerosis, glaucoma, myotonic dystrophy, Guillain-Barre' syndrome (GBS), Myastenia Gravis, Bullous Pemphigoid, spinal muscular atrophy, Down syndrome, Parkinson's disease, and Huntington's disease. In some embodiments that may be combined with any of the preceding embodiments, the disease associated with complement activation is an inflammatory disease, an autoimmune disease, or metabolic disorder. In some embodiments that may be combined with any of the preceding embodiments, the inflammatory disease, autoimmune disease, or metabolic disorder is selected from diabetes, obesity, rheumatoid arthritis (RA), acute respiratory distress syndrome (ARDS), remote tissue injury after ischemia and reperfusion, complement activation during cardiopulmonary bypass surgery, dermatomyositis, pemphigus, lupus nephritis and resultant glomerulonephritis and vasculitis, cardiopulmonary bypass, cardioplegia-induced coronary endothelial dysfunction, type II membranoproliferative glomerulonephritis, IgA nephropathy, acute renal failure, cryoglobulemia, antiphospholipid syndrome, Chronic open-angle glaucoma, acute closed angle glaucoma, macular degenerative diseases, age-related macular degeneration (AMD), (AMD-wet), Geographic atrophy choroidal neovascularization (CNV), uveitis, diabetic retinopathy, ischemia-related retinopathy, endophthalmitis, intraocular neovascular disease, diabetic macular edema, pathological myopia, von Hippel-Lindau disease, histoplasmosis of the eye, Neuromyelitis Optica (NMO), Central Retinal Vein Occlusion (CRVO), corneal neovascularization, retinal neovascularization, Leber's hereditary optic neuropathy, optic neuritis, Behcet's retinopathy, ischemic optic neuropathy, retinal vasculitis, ANCA vasculitis, Purtscher retinopathy, Sjogren's dry eye disease, dry AMD, sarcoidosis, temporal arteritis, polyarteritis nodosa, multiple sclerosis, allo-transplantation, hyperacute rejection, hemodialysis, chronic occlusive pulmonary distress syndrome (COPD), asthma, and aspiration pneumonia. In some embodiments that may be combined with any of the preceding embodiments, the disease associated with complement activation is an autoimmune disease selected from myasthenia gravis, Diabetes mellitus type 1, Hashimoto's thyroiditis, Addison's disease, Coeliac disease, Crohn's disease, pernicious anaemia, Pemphigus vulgaris, vitiligo, autoimmune hemolytic anemias, paraneoplastic syndromes, a vasculitis disease, hypocomplementemic urticarial vasculitis (HUV), polymyalgia rheumatica, temporal arteritis, and Wegener's granulomatosis.

In certain aspects, the present disclosure provides a kit comprising a humanized anti-C1q antibody of any of the preceding embodiments, and a package insert comprising instructions for using the antibody to treat or prevent a disease associated with complement activation in an individual in need of such treatment. In some embodiments, the disease associated with complement activation is a neurodegenerative disorder. In some embodiments, the neurodegenerative disorder is associated with loss of synapses or loss nerve connections. In some embodiments, the neurodegenerative disorder is associated with synapse loss that is dependent on the complement receptor 3(CR3)/C3 or complement receptor CR1. In some embodiments, the neurodegenerative disorder is associated with pathological activity-dependent synaptic pruning. In some embodiments, the neurodegenerative disorder is associated with synapse phagocytosis by microglia. In some embodiments, the neurodegenerative disorder is selected from Alzheimer's disease, amyotrophic lateral sclerosis, multiple sclerosis, glaucoma, myotonic dystrophy, Down syndrome, Parkinson's disease, and Huntington's disease. In some embodiments, the disease associated with complement activation is an inflammatory disease, autoimmune disease, or metabolic disorder. In some embodiments, the inflammatory disease, autoimmune disease, or metabolic disorder is selected from diabetes, obesity, rheumatoid arthritis (RA), acute respiratory distress syndrome (ARDS), remote tissue injury after ischemia and reperfusion, complement activation during cardiopulmonary bypass surgery, dermatomyositis, pemphigus, lupus nephritis and resultant glomerulonephritis and vasculitis, cardiopulmonary bypass, cardioplegia-induced coronary endothelial dysfunction, type II membranoproliferative glomerulonephritis, IgA nephropathy, acute renal failure, cryoglobulemia, antiphospholipid syndrome, Chronic open-angle glaucoma, acute closed angle glaucoma, macular degenerative diseases, age-related macular degeneration (AMD), Geographic atrophy, choroidal neovascularization (CNV), uveitis, diabetic retinopathy, ischemia-related retinopathy, endophthalmitis, intraocular neovascular disease, diabetic macular edema, pathological myopia, von Hippel-Lindau disease, histoplasmosis of the eye, Neuromyelitis Optica (NMO), Central Retinal Vein Occlusion (CRVO), corneal neovascularization, retinal neovascularization, Leber's hereditary optic neuropathy, optic neuritis, Behcet's retinopathy, ischemic optic neuropathy, retinal vasculitis, ANCA vasculitis, Purtscher retinopathy, Sjogren's dry eye disease, dry AMD, sarcoidosis, temporal arteritis, polyarteritis nodosa, multiple sclerosis, allo-transplantation, hyperacute rejection, hemodialysis, chronic occlusive pulmonary distress syndrome (COPD), asthma, and aspiration pneumonia. In some embodiments, the disease associated with complement activation is an autoimmune disease selected from myasthenia gravis, Diabetes mellitus type 1, Hashimoto's thyroiditis, Addison's disease, Coeliac disease, Crohn's disease, pernicious anaemia, Pemphigus vulgaris, vitiligo, autoimmune hemolytic anemias, paraneoplastic syndromes, a vasculitis disease, hypocomplementemic urticarial vasculitis (HUV), polymyalgia rheumatica, temporal arteritis, and Wegener's granulomatosis.

In certain aspects, the present disclosure provides a kit comprising a humanized anti-C1q antibody of any of the preceding embodiments. In some embodiments, the kit is for diagnostic or therapeutic uses as disclosed herein.

In certain aspects, the present disclosure provides a method of detecting synapses in an individual, by a) administering a humanized anti-C1q antibody of any of the preceding embodiments to the individual, and b) detecting antibody bound to synapses, thereby detecting synapses in the individual. In other aspects, the present disclosure provides a humanized anti-C1q antibody of any of the preceding embodiments for use in detecting synapses in an individual. In other aspects, the present disclosure provides use of a humanized anti-C1q antibody of any of the preceding embodiments in the manufacture of a medicament for detecting synapses in an individual. In some embodiments that may be combined with any of the preceding embodiments, the antibody bound to synapses is detected using imaging techniques selected from positron emission tomography (PET), X-ray computed tomography, single-photon emission computed tomography (SPECT), computed tomography (CT), and computed axial tomography (CAT). In some embodiments that may be combined with any of the preceding embodiments, the detection of antibody bound to synapses provides a quantitative measure of the number of synapses in the individual. In some embodiments that may be combined with any of the preceding embodiments, the individual has a neurodegenerative disease or autoimmune disease. In some embodiments that may be combined with any of the preceding embodiments, the number of synapses in the individual is measured repeatedly over a period of time and a loss of synapses in the individual is detected over time. In some embodiments that may be combined with any of the preceding embodiments, the loss of synapses over time is a measure for the efficacy of a treatment for the neurodegenerative disease or autoimmune disease.

In certain aspects, the present disclosure provides a method of detecting synapses in a biological sample, by a) contacting the biological sample with a humanized anti-C1q antibody of any of the preceding embodiments, and b) detecting antibody bound to synapses, thereby detecting synapses in the individual.

In some embodiments that may be combined with any of the preceding embodiments, the method further comprises a step before step a) of obtaining the biological sample from an individual. In some embodiments that may be combined with any of the preceding embodiments, the biological sample comprises a biopsy specimen, a tissue, or a cell. In some embodiments that may be combined with any of the preceding embodiments, the antibody is detected by immunofluorescence microscopy, immunocytochemistry, immunohistochemistry, ELISA, FACS analysis, immunoprecipitation, or micro-positron emission tomography.

It is to be understood that one, some, or all of the properties of the various embodiments described herein may be combined to form other embodiments of the compositions and methods provided herein. These and other aspects of the compositions and methods provided herein will become apparent to one of skill in the art.

DESCRIPTION OF THE FIGURES

FIG. 1A depicts a plasmid map for light chain expression vector pANTVk. FIG. 1B depicts a plasmid map for and heavy chain expression vector pANTVhG4 (S241P L248E). Both VH and Vκ vectors contain genomic DNA fragments incorporating introns and polyA sequences. Expression of both chains is driven by a CMV promoter and selection (on the heavy chain vector) is via a DHFR mini gene.

FIG. 2A depicts an alignment of amino acid sequence of the heavy chain variable region (VH) of the M1 antibody and the amino acid sequences of the humanized VH variants VH1-VH2 (SEQ ID NOs 21, 1, 21 and 2, respectively, in order of appearance). FIG. 2B depicts an alignment of amino acid sequence of the heavy chain variable region (VH) of the M1 antibody and the amino acid sequences of the humanized VH variants VH3-VH4 (SEQ ID NOs 21, 3, 21 and 4, respectively, in order of appearance). FIG. 2C depicts an alignment of amino acid sequence of the kappa light chain variable region (Vκ) of the M1 antibody and the amino acid sequences of the humanized Vκ variants Vκ1-Vκ2 (SEQ ID NOs 22, 5, 22 and 6, respectively, in order of appearance). FIG. 2D depicts an alignment of amino acid sequence of the kappa light chain variable region (Vκ) of the M1 antibody and the amino acid sequences of the humanized Vκ variants Vκ3-Vκ4 (SEQ ID NOs 22, 7, 22 and 8, respectively, in order of appearance).

FIG. 4A depicts the results with the humanized antibodies VH1/Vκ1, VH1/Vκ2, and VH1/Vκ3. FIG. 4B depicts the results with the humanized antibodies VH1/Vκ4, VH2/Vκ1, VH2/Vκ2, VH2/Vκ3, and VH2/Vκ4. FIG. 4C depicts the results with the humanized antibodies VH3/Vκ1, VH3/Vκ2, VH3/Vκ3, and VH3/Vκ4. FIG. 4D depicts the results with the humanized antibodies VH4/Vκ1, VH4/Vκ2, VH4/Vκ3, and VH4/Vκ4.

FIG. 6 depicts a Coomassie Blue-stained SDS-PAGE gel of gel filtration-purified antibodies. 1 µg of each sample was loaded on a NuPage 4-12% Bis-Tris gel and run at 200V for 35 min. Size marker (M) is pre-stained protein standard Fermentas PageRuler Plus. Lane 1 depicts Fab VH3/Vκ3 reduced; lane 2 depicts Fab VH3/Vκ3 non-reduced; lane 3 depicts IgG V VH3/Vκ3 reduced; and lane 4 depicts IgG VH3/Vκ3 non-reduced.

FIG. 7A illustrates results from a human CH50 hemolytic assay. FIG. 7B illustrates results from a rat CH50 hemolytic assay. "ANN-005" corresponds to the monoclonal antibody M1, "3E2" corresponds to a chimeric M1 antibody, "2B12" corresponds to antibody VH1/Vκ1, "5H7" corresponds to antibody VH3/Vκ3, "3F1" corresponds to antibody VH3/Vκ4, and "1D3" corresponds to antibody VH4/Vκ3.

FIG. 9A depicts the time course of serum C1q levels in monkeys using the JL1-M1 assay. FIG. 9B depicts the time course of serum C1q levels in monkeys using the JL1-JL1 assay.

DETAILED DESCRIPTION

General Techniques

Figure 1B:
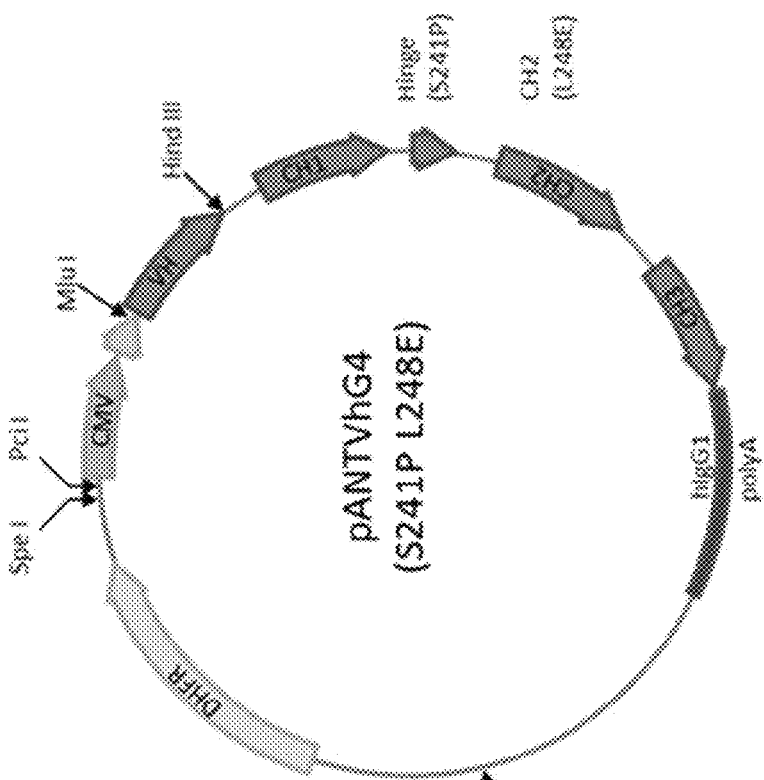
FIG. 1A and FIG. 1B depict plasmid maps for light chain and heavy chain expression vectors.

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual*, and *Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

Definitions

As used herein, the term "preventing" includes providing prophylaxis with respect to occurrence or recurrence of a particular disease, disorder, or condition in an individual. An individual may be predisposed to, susceptible to a particular disease, disorder, or condition, or at risk of developing such a disease, disorder, or condition, but has not yet been diagnosed with the disease, disorder, or condition.

As used herein, an individual "at risk" of developing a particular disease, disorder, or condition may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of a particular disease, disorder, or condition, as known in the art. An individual having one or more of these risk factors has a higher probability of developing a particular disease, disorder, or condition than an individual without one or more of these risk factors.

As used herein, the term "treatment" refers to clinical intervention designed to alter the natural course of the individual being treated during the course of clinical pathology. Desirable effects of treatment include decreasing the rate of progression, ameliorating or palliating the pathological state, and remission or improved prognosis of a particular disease, disorder, or condition. An individual is successfully "treated", for example, if one or more symptoms associated with a particular disease, disorder, or condition are mitigated or eliminated.

An "effective amount" refers to at least an amount effective, at dosages and for periods of time necessary, to achieve the desired therapeutic or prophylactic result. An effective amount can be provided in one or more administrations.

A "therapeutically effective amount" is at least the minimum concentration required to effect a measurable improvement of a particular disease, disorder, or condition. A therapeutically effective amount herein may vary according to factors such as the disease state, age, sex, and weight of the patient, and the ability of the anti-C1q antibody to elicit a desired response in the individual. A therapeutically effective amount is also one in which any toxic or detrimental effects of the anti-C1q antibody are outweighed by the therapeutically beneficial effects.

"Chronic" administration refers to administration of the medicament(s) in a continuous as opposed to acute mode, so as to maintain the initial therapeutic effect (activity) for an extended period of time. "Intermittent" administration refers to treatment that is not consecutively done without interruption, but rather is cyclic in nature.

As used herein, administration "in conjunction" with another compound or composition includes simultaneous administration and/or administration at different times. Administration in conjunction also encompasses administration as a co-formulation or administration as separate compositions, including at different dosing frequencies or intervals, and using the same route of administration or different routes of administration.

An "individual" for purposes of treatment, prevention, or reduction of risk refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. In some embodiments, the individual is human.

As used herein, "autoantibody" means any antibody that recognizes a host antigen.

The term "immunoglobulin" (Ig) is used interchangeably with "antibody" herein. The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity.

The basic 4-chain antibody unit is a heterotetrameric glycoprotein composed of two identical light (L) chains and two identical heavy (H) chains. The pairing of a $V_H$ and $V_L$ together forms a single antigen-binding site. For the structure and properties of the different classes of antibodies, see, e.g., Basic and Clinical Immunology, 8th Ed., Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa ("κ") and lambda ("λ"), based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha ("α"), delta ("δ"), epsilon ("ε"), gamma ("γ") and mu ("μ"), respectively. The γ and α classes are further divided into subclasses (isotypes) on the basis of relatively minor differences in the CH sequence and function, e.g., humans express the following subclasses: IgG1, IgG2, IgG3, IgG4, IgA1, and IgA2. The subunit structures and three dimensional configurations of different classes of immunoglobulins are well known and described generally in, for example, Abbas et al., Cellular and Molecular Immunology, $4^{th}$ ed. (W.B. Saunders Co., 2000).

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

An "isolated" antibody, such as an anti-C1q antibody of the present disclosure, is one that has been identified, separated and/or recovered from a component of its production environment (e.g., naturally or recombinantly). In some embodiments, the isolated polypeptide is free of association with all other contaminant components from its production environment. Contaminant components from its production environment, such as those resulting from recombinant transfected cells, are materials that would typically interfere with research, diagnostic or therapeutic uses for the antibody, and may include enzymes, hormones, and other proteinaceous or non-proteinaceous solutes. In some embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or silver stain. Isolated antibody includes the antibody in situ within recombinant T-cells since at least one component of the antibody's natural environment will not be present. Ordinarily, however, an isolated polypeptide or antibody will be prepared by at least one purification step.

The "variable region" or "variable domain" of an antibody, such as an anti-C1q antibody of the present disclosure, refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites.

The term "variable" refers to the fact that certain segments of the variable domains differ extensively in sequence among antibodies, such as anti-C1q antibodies of the present disclosure. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen binding site of antibodies (see Kabat et al., Sequences of Immunological Interest, Fifth Edition, National Institute of Health, Bethesda, Md. (1991)). The constant domains are not involved directly in the binding of antibody to an antigen, but exhibit various effector functions, such as participation of the antibody in antibody-dependent-cellular toxicity.

The term "monoclonal antibody" as used herein refers to an antibody, such as an anti-C1q antibody of the present disclosure, obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by a variety of techniques, including, for example, the hybridoma method (e.g., Kohler and Milstein., *Nature,* 256:495-97 (1975); Hongo et al., *Hybridoma,* 14 (3):253-260 (1995), Harlow et al., *Antibodies: A Laboratory Manual,* (Cold Spring Harbor Laboratory Press, 2d ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature,* 352:624-628 (1991); Marks et al., *J. Mol. Biol.* 222:581-597 (1992); Sidhu et al., *J. Mol. Biol.* 338(2): 299-310 (2004); Lee et al., *J. Mol. Biol.* 340(5):1073-1093 (2004); Fellouse, *Proc. Nat'l Acad. Sci. USA* 101(34):12467-472 (2004); and Lee et al., *J. Immunol. Methods* 284(1-2):119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Nat'l Acad. Sci. USA* 90:2551 (1993); Jakobovits et al., *Nature* 362:255-258 (1993); Bruggemann et al., *Year in Immunol.* 7:33 (1993); U.S. Pat. Nos. 5,545,807; 5,545,806; 5,569,825; 5,625,126; 5,633, 425; and 5,661,016; Marks et al., *Bio/Technology* 10:779-783 (1992); Lonberg et al., *Nature* 368:856-859 (1994); Morrison, *Nature* 368:812-813 (1994); Fishwild et al., *Nature Biotechnol.* 14:845-851 (1996); Neuberger, *Nature Biotechnol.* 14:826 (1996); and Lonberg and Huszar, *Intern. Rev. Immunol.* 13:65-93 (1995).

The terms "full-length antibody," "intact antibody" or "whole antibody" are used interchangeably to refer to an antibody, such as and anti-C1q antibody of the present disclosure, in its substantially intact form, as opposed to an antibody fragment. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., *Protein Eng.* 8(10):1057-1062 (1995)); single-chain antibody molecules and multispecific antibodies formed from antibody fragments.

Papain digestion of antibodies, such as anti-C1q antibodies of the present disclosure, produces two identical antigen-binding fragments or regions, called "Fab" fragments or regions, and a residual "Fc" fragment or region, a designation reflecting the ability to crystallize readily. The Fab fragment or region consists of an entire L chain along with the variable region domain of the H chain ($V_H$), and the first constant domain of one heavy chain ($C_H1$). Each Fab fragment or region is monovalent with respect to antigen binding, i.e., it has a single antigen-binding site. Pepsin treatment of an antibody yields a single large F(ab')$_2$ fragment or region which roughly corresponds to two disulfide linked Fab fragments having different antigen-binding activity and is still capable of cross-linking antigen. Fab' fragments or regions differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment or region comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. In some embodiments, the sFv polypeptide further comprises a polypeptide linker between the $V_H$ and $V_L$ domains which enables the sFv to form the desired structure for antigen binding. For a review of the sFv, see Plückthun in *The Pharmacology of Monoclonal Antibodies,* vol. 113, Rosenburg and Moore eds., Springer-Verlag, New York, pp. 269-315 (1994).

"Functional fragments" of antibodies, such as anti-C1q antibodies of the present disclosure, comprise a portion of an intact antibody, generally including the antigen binding or variable region of the intact antibody or the F region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., *Proc. Nat'l Acad. Sci. USA* 90:6444-48 (1993).

As used herein, a "chimeric antibody" refers to an antibody (immunoglobulin), such as an anti-C1q antibody of the present disclosure, in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Nat'l Acad.*

Sci. USA, 81:6851-55 (1984)). Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies, such as anti-C1q antibodies of the present disclosure, are chimeric antibodies that contain minimal sequence derived from non-human immunoglobulin. In one embodiment, a humanized antibody is a human immunoglobulin (recipient antibody) in which residues from an HVR of the recipient are replaced by residues from an HVR of a non-human species (donor antibody) such as mouse, rat, rabbit or non-human primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, and the like. The number of these amino acid substitutions in the FR is typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, for example, Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is one that possesses an amino-acid sequence corresponding to that of an antibody, such as an anti-C1q antibody of the present disclosure, produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227:381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147(1):86-95 (1991). See also van Dijk and van de Winkel, *Curr. Opin. Pharmacol.* 5:368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Nat'l Acad. Sci. USA,* 103:3557-3562 (2006) regarding human antibodies generated via a human B-cell hybridoma technology.

The term "hypervariable region," "HVR," or "HV," when used herein refers to the regions of an antibody-variable domain, such as that of an anti-C1q antibody of the present disclosure, that are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu in *Methods in Molecular Biology* 248:1-25 (Lo, ed., Human Press, Totowa, N.J., 2003)). Indeed, naturally occurring camelid antibodies consisting of a heavy chain only are functional and stable in the absence of light chain. See, e.g., Hamers-Casterman et al., *Nature* 363:446-448 (1993) and Sheriff et al., *Nature Struct. Biol.* 3:733-736 (1996).

A number of HVR delineations are in use and are encompassed herein. The HVRs that are Kabat complementarity-determining regions (CDRs) are based on sequence variability and are the most commonly used (Kabat et al., supra). Chothia refers instead to the location of the structural loops (Chothia and Lesk *J. Mol. Biol.* 196:901-917 (1987)). The AbM HVRs represent a compromise between the Kabat CDRs and Chothia structural loops, and are used by Oxford Molecular's AbM antibody-modeling software. The "contact" HVRs are based on an analysis of the available complex crystal structures. The residues from each of these HVRs are noted below.

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat numbering) |
| H1 | H31-H35 | H26-H35 | H26-H32 | H30-H35 (Chothia numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2), and 89-97 or 89-96 (L3) in the VL, and 26-35 (H1), 50-65 or 49-65 (H2), and 93-102, 94-102, or 95-102 (H3) in the VH. The variable-domain residues are numbered according to Kabat et al., supra, for each of these extended-HVR definitions.

"Framework" or "FR" residues are those variable-domain residues other than the HVR residues as herein defined.

The phrase "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g., residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see United States Patent Publication No. 2010-280227).

An "acceptor human framework" as used herein is a framework comprising the amino acid sequence of a VL or VH framework derived from a human immunoglobulin framework or a human consensus framework. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less. In some embodiments, where pre-existing amino acid changes are present in a VH, those changes occur at only three, two, or one of positions 71H, 73H and 78H; for instance, the amino acid residues at those positions may by 71A, 73T and/or 78A. In one embodiment, the VL acceptor human framework is identical in sequence to the VL human immunoglobulin framework sequence or human consensus framework sequence.

A "human consensus framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, 5th Ed. Public Health Service, National Institutes of Health, Bethesda, Md. (1991). Examples include for the VL, the subgroup may be subgroup kappa I, kappa II, kappa III or kappa IV as in Kabat et al., supra. Additionally, for the VH, the subgroup may be subgroup I, subgroup II, or subgroup III as in Kabat et al., supra.

An "amino-acid modification" at a specified position, e.g., of an anti-C1q antibody of the present disclosure, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. In some embodiments, the amino acid modification herein is a substitution.

An "affinity-matured" antibody, such as an anti-C1q antibody of the present disclosure, is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al., *Bio/Technology* 10:779-783 (1992) describes affinity maturation by VH- and VL-domain shuffling. Random mutagenesis of HVR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

As use herein, the term "specifically recognizes" or "specifically binds" refers to measurable and reproducible interactions such as attraction or binding between a target and an antibody, such as an anti-C1q antibody of the present disclosure, that is determinative of the presence of the target in the presence of a heterogeneous population of molecules including biological molecules. For example, an antibody, such as an anti-C1q antibody of the present disclosure, that specifically or preferentially binds to a target or an epitope is an antibody that binds this target or epitope with greater affinity, avidity, more readily, and/or with greater duration than it binds to other targets or other epitopes of the target. It is also understood by reading this definition that, for example, an antibody (or a moiety) that specifically or preferentially binds to a first target may or may not specifically or preferentially bind to a second target. As such, "specific binding" or "preferential binding" does not necessarily require (although it can include) exclusive binding. An antibody that specifically binds to a target may have an association constant of at least about $10^3$ $M^{-1}$ or $10^4$ $M^{-1}$, sometimes about $10^5$ $M^{-1}$ or $10^6$ $M^{-1}$, in other instances about $10^6$ $M^{-1}$ or $10^7$ $M^{-1}$, about $10^8$ $M^{-1}$ to $10^9$ $M^{-1}$, or about $10^{10}$ $M^{-1}$ to $10^{11}$ $M^{-1}$ or higher. A variety of immunoassay formats can be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

As used herein, an "interaction" between a complement protein, such as complement factor C1q, and a second protein encompasses, without limitation, protein-protein interaction, a physical interaction, a chemical interaction, binding, covalent binding, and ionic binding. As used herein, an antibody "inhibits interaction" between two proteins when the antibody disrupts, reduces, or completely eliminates an interaction between the two proteins. An antibody of the present disclosure, or fragment thereof, "inhibits interaction" between two proteins when the antibody or fragment thereof binds to one of the two proteins.

A "blocking" antibody, an "antagonist" antibody, an "inhibitory" antibody, or a "neutralizing" antibody is an antibody, such as an anti-C1q antibody of the present disclosure that inhibits or reduces one or more biological activities of the antigen it binds, such as interactions with one or more proteins. In some embodiments, blocking antibodies, antagonist antibodies, inhibitory antibodies, or "neutralizing" antibodies substantially or completely inhibit one or more biological activities or interactions of the antigen.

Antibody "effector functions" refer to those biological activities attributable to the Fc region (a native sequence Fc region or amino acid sequence variant Fc region) of an antibody, and vary with the antibody isotype.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the present disclosure include human IgG1, IgG2, IgG3 and IgG4.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification. In some embodiments, the variant Fc region differs in one or more amino acid substitution(s). In some embodiments, the variant Fc region has at least one amino acid substitution compared to a native sequence Fc region or to the Fc region of a parent polypeptide, e.g. from about one to about ten amino acid substitutions, and, in some embodiments, from about one to about five amino acid substitutions in a native sequence Fc region or in the Fc region of the parent polypeptide. The variant Fc region herein will, in some embodiments, possess at least about 80% homology with a native sequence Fc region and/or with an Fc region of a parent polypeptide, and, in some embodiments, at least about 90% homology therewith, and, in some embodiments, at least about 95% homology therewith.

"Fc receptor" or "FcR" describes a receptor that binds to the Fc region of an antibody. In some embodiments, the FcR is a native sequence human FcR. Moreover, in some embodiments, a FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif ("ITAM") in its cytoplasmic domain. Inhibiting receptor FcγRIIB contains an immunoreceptor tyrosine-based inhibition motif ("ITIM") in its cytoplasmic domain (see, e.g., M. Daëron, *Annu. Rev. Immunol.* 15:203-234 (1997)). FcRs are reviewed in Ravetch and Kinet, *Annu. Rev. Immunol.* 9:457-92 (1991); Capel et al., *Immunomethods* 4:25-34 (1994); and de Haas et al., *J. Lab. Clin. Med.* 126: 330-41 (1995). Other FcRs, including those to be identified in the future, are encompassed by the term "FcR" herein. FcRs can also increase the serum half-life of antibodies.

Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody variants with improved or diminished binding to FcRs. See also, e.g., Shields et al., *J. Biol. Chem.* 9(2):6591-6604 (2001).

The term "$k_{on}$", as used herein, is intended to refer to the rate constant for association of an antibody to an antigen.

The term "$k_{off}$", as used herein, is intended to refer to the rate constant for dissociation of an antibody from the antibody/antigen complex.

The term "$K_D$", as used herein, is intended to refer to the equilibrium dissociation constant of an antibody-antigen interaction.

As used herein, "percent (%) amino acid sequence identity" and "homology" with respect to a peptide, polypeptide or antibody sequence refers to the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms known in the art needed to achieve maximal alignment over the full length of the sequences being compared.

An "isolated" molecule or cell is a molecule or a cell that is identified and separated from at least one contaminant molecule or cell with which it is ordinarily associated in the environment in which it was produced. In some embodiments, the isolated molecule or cell is free of association with all components associated with the production environment. The isolated molecule or cell is in a form other than in the form or setting in which it is found in nature. Isolated molecules therefore are distinguished from molecules existing naturally in cells; isolated cells are distinguished from cells existing naturally in tissues, organs, or individuals. In some embodiments, the isolated molecule is an anti-C1q antibody of the present disclosure. In other embodiments, the isolated cell is a host cell or hybridoma cell producing an anti-C1q antibody of the present disclosure.

An "isolated" nucleic acid molecule encoding an antibody, such as an anti-C1q antibody of the present disclosure, is a nucleic acid molecule that is identified and separated from at least one contaminant nucleic acid molecule with which it is ordinarily associated in the environment in which it was produced. In some embodiments, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO, or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this disclosure.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "about" as used herein refers to the usual error range for the respective value readily known to the skilled person in this technical field. Reference to "about" a value or parameter herein includes (and describes) embodiments that are directed to that value or parameter per se.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

It is understood that aspects and embodiments of the present disclosure described herein include "comprising," "consisting," and "consisting essentially of" aspects and embodiments.

Overview

The present disclosure provides humanized anti-C1q antibodies and uses thereof. The humanized anti-C1q antibodies of the present disclosure specifically bind a C1q protein of this disclosure. In some embodiments, the humanized anti-C1q antibodies are C1q neutralizing antibodies. In some embodiments, the humanized anti-C1q antibodies of this disclosure may bind to C1 complex.

In certain aspects, the present disclosure provides a humanized antibody that specifically binds to a C1q protein, wherein the antibody comprises a heavy chain variable region and a human heavy chain constant region, wherein the heavy chain variable region comprises an Fab region and the heavy chain constant region comprises an Fc region, wherein the Fab region specifically binds to the C1q protein, and wherein the Fc region is incapable of binding the C1q protein.

In certain aspects, the present disclosure provides a humanized anti-C1q antibody, or an antigen-binding fragment thereof, the antibody comprising a heavy chain variable domain and a light chain variable domain, wherein the heavy chain variable domain comprises an amino acid sequence selected from SEQ ID NOs: 1-4, or an amino acid sequence with at least about 90% homology to the amino acid sequence selected from SEQ ID NOs: 1-4.

In certain aspects, the present disclosure provides a humanized anti-C1q antibody, or an antigen-binding fragment thereof, the antibody comprising a heavy chain variable domain and a light chain variable domain, wherein the light chain variable domain comprises an amino acid sequence selected from SEQ ID NOs: 5-8, or an amino acid sequence with at least about 90% homology to the amino acid sequence selected from SEQ ID NOs: 5-8.

In certain aspects, the present disclosure provides a humanized anti-C1q antibody, or an antigen-binding fragment thereof, the antibody comprising: a heavy chain variable domain comprising an amino acid sequence selected from SEQ ID NOs: 1-4, or an amino acid sequence with at least about 90% homology to the amino acid sequence selected from SEQ ID NOs: 1-4; and/or a light chain variable domain comprising an amino acid sequence selected from SEQ ID NOs: 5-8, or an amino acid sequence with at least about 90% homology to the amino acid sequence selected from SEQ ID NOs: 5-8.

In some embodiments, the humanized anti-C1q antibodies of the present disclosure neutralize a biological activity of C1q. Uses for humanized anti-C1q antibodies include, without limitation, the detection of complement factor C1q, e.g., in individuals having a neurodegenerative disorder associated with complement factor 1 (CF 1)-dependent pathological synapse loss. Additional non-limiting uses include the inhibition of the classical pathway of complement activation, e.g., in cases where the classical complement pathway is activated by autoantibodies. Further non-limiting uses for humanized anti-C1q antibodies include the diagnosis and treatment of disorders that are associated with elevated expression of complement factors, such as C1q, or associated with the activation of the complement pathway. Such disorders may include, without limitation, autoimmune disorders, inflammatory disorders, and neurodegenerative disorders, including neurodegenerative disorders associated with synapse loss.

In another aspect, the present disclosure provides an isolated nucleic acid molecule encoding an antibody of the present disclosure.

The present disclosure also provides isolated host cells containing a nucleic acid molecule that encodes an antibody of this disclosure. Additionally, pharmaceutical compositions are provided containing anti-C1q antibodies, such as humanized C1q neutralizing antibodies of this disclosure, in combination with pharmaceutically acceptable carriers. The present disclosure also provides a kit containing a humanized anti-C1q antibody for use in any of the methods described herein.

The present disclosure further provides methods of using the humanized anti-C1q antibodies of the present disclosure (e.g., humanized C1q neutralizing antibodies of this disclosure) to treat or prevent a neurodegenerative disease or autoimmune disease in an individual in need of such treatment, to detect synapses in an individual having a neurodegenerative disease or autoimmune disease, and to detect synapses in a biological sample. The present disclosure also provides kits containing humanized anti-C1q antibodies of the present disclosure (e.g., humanized C1q neutralizing antibodies of this disclosure).

Complement Proteins

The antibodies of this disclosure specifically recognize complement factor C1q and/or C1q in the C1 complex of the classical complement activation pathway. The recognized complement factor may be derived, without limitation, from any organism having a complement system, including any mammalian organism such as human, mouse, rat, rabbit, monkey, dog, cat, cow, horse, camel, sheep, goat, or pig.

As used herein "C1 complex" refers to a protein complex that may include, without limitation, one C1q protein, two C1r proteins, and two C1s proteins (e.g., $C1qr_2s_2$).

As used herein "complement factor C1q" refers to both wild type sequences and naturally occurring variant sequences.

A non-limiting example of a complement factor C1q recognized by antibodies of this disclosure is human C1q, including the three polypeptide chains A, B, and C:

```
C1q, chain A (homo sapiens), Accession No. Protein
Data Base: NP_057075.1; GenBank No.: NM_015991:
>gi|7705753|ref|NP_057075.1|complement C1q
subcomponent subunit A precursor [Homo sapiens]
                                        (SEQ ID NO: 9)
MEGPRGWLVLCVLAISLASMVTEDLCRAPDGKKGEAGRPGRRGRPGLKGE

QGEPGAPGIRTGIQGLKGDQGEPGPSGNPGKVGYPGPSGPLGARGIPGIK

GTKGSPGNIKDQPRPAFSAIRRNPPMGGNVVIFDTVITNQEEPYQNHSGR

FVCTVPGYYYFTFQVLSQWEICLSIVSSSRGQVRRSLGFCDTTNKGLFQV

VSGGMVLQLQQGDQVWVEKDPKKGHIYQGSEADSVFSGFLIFPSA.

C1q, chain B (homo sapiens), Accession No. Protein
Data Base: NP_000482.3; GenBank No.: NM_000491.3:
>gi|87298828|ref|NP_000482.3|complement C1q
subcomponent subunit B precursor [Homo sapiens]
                                        (SEQ ID NO: 10)
MMMKIPWGSIPVLMLLLLLGLIDISQAQLSCTGPPAIPGIPGIPGTPGPD

GQPGTPGIKGEKGLPGLAGDHGEFGEKGDPGIPGNPGKVGPKGPMGPKGG

PGAPGAPGPKGESGDYKATQKIAFSATRTINVPLRRDQTIRFDHVITNMN

NNYEPRSGKFTCKVPGLYYFTYHASSRGNLCVNLMRGRERAQKVVTFCDY

AYNTFQVTTGGMVLKLEQGENVFLQATDKNSLLGMEGANSIFSGFLLFPD

MEA.

C1q, chain C (homo sapiens), Accession No. Protein
Data Base: NP_001107573.1; GenBank No.:
NM_001114101.1:
>gi|166235903|ref|NP_001107573.1|complement C1q
subcomponent subunit C precursor [Homo sapiens]
                                        (SEQ ID NO: 11)
MDVGPSSLPHLGLKLLLLLLLPLRGQANTGCYGIPGMPGLPGAPGKDGY

DGLPGPKGEPGIPAIPGIRGPKGQKGEPGLPGHPGKNGPMGPPGMPGVPG

PMGIPGEPGEEGRYKQKFQSVFTVTRQTHQPPAPNSLIRFNAVLTNPQGD
```

-continued

YDTSTGKFTCKVPGLYYFVYHASHTANLCVLLYRSGVKVVTFCGHTSKTN

QVNSGGVLLRLQVGEEVWLAVNDYYDMVGIQGSDSVFSGFLLFPD.

Accordingly, a humanized anti-C1q antibody of the present disclosure may bind to polypeptide chain A, polypeptide chain B, and/or polypeptide chain C of a C1q protein. In some embodiments, a humanized anti-C1q antibody of the present disclosure binds to polypeptide chain A, polypeptide chain B, and/or polypeptide chain C of human C1q or a homolog thereof, such as mouse, rat, rabbit, monkey, dog, cat, cow, horse, camel, sheep, goat, or pig C1q.

Humanized Anti-C1q Antibodies

Humanized antibodies of the present disclosure specifically bind to a complement factor C1q and/or C1q protein in the C1 complex of the classical complement pathway. In some embodiments, the humanized anti-C1q antibodies specifically bind to human C1q. In some embodiments, the humanized anti-C1q antibodies specifically bind to human and mouse C1q. In some embodiments, the humanized anti-C1q antibodies specifically bind to rat C1q. In some embodiments, the humanized anti-C1q antibodies specifically bind to human C1q, mouse C1q, and rat C1q.

In some embodiments, humanized anti-C1q antibodies of the present disclosure include a heavy chain variable region that contains an Fab region and a heavy chain constant regions that contains an Fc region, where the Fab region specifically binds to a C1q protein of the present disclosure, but the Fc region is incapable of binding the C1q protein. In some embodiments, the Fc region is from a human IgG1, IgG2, IgG3, or IgG4 isotype. In some embodiments, the Fc region is incapable of inducing complement activity and/or incapable of inducing antibody-dependent cellular cytotoxicity (ADCC). In some embodiments, the Fc region comprises one or more modifications, including, without limitation, amino acid substitutions. In certain embodiments, the Fc region of humanized anti-C1q antibodies of the present disclosure comprise an amino acid substitution at position 248 according to Kabat numbering convention or a position corresponding to position 248 according to Kabat numbering convention, and/or at position 241 according to Kabat numbering convention or a position corresponding to position 241 according to Kabat numbering convention. In some embodiments, the amino acid substitution at position 248 or a positions corresponding to position 248 inhibits the Fc region from interacting with an Fc receptor. In some embodiments, the amino acid substitution at position 248 or a positions corresponding to position 248 is a leucine to glutamate amino acid substitution. In some embodiments, the amino acid substitution at position 241 or a positions corresponding to position 241 prevents arm switching in the antibody. In some embodiments, the amino acid substitution at position 241 or a positions corresponding to position 241 is a serine to proline amino acid substitution. In certain embodiments, the Fc region of humanized anti-C1q antibodies of the present disclosure comprises the amino acid sequence of SEQ ID NO: 37, or an amino acid sequence with at least about 70%, at least about 75%, at least about 80% at least about 85% at least about 90%, or at least about 95% homology to the amino acid sequence of SEQ ID NO: 37.

In some embodiments, the humanized anti-C1q antibodies of the present disclosure neutralize a biological activity of complement factor C1q. In some embodiments, the antibodies inhibit the interaction between complement factor C1q and other complement factors, such as C1r or C1s or between C1q and an antibody, such as an autoantibody. As disclosed herein, an autoantibody of the present disclosure includes, without limitation, an antibody that recognizes a host antigen and activates the classical pathway of complement activation. In the first step of this activation process complement factor C1q binds to the autoantibody-autoantigen-immune complex. In some embodiments, the antibodies inhibit the interaction between complement factor C1q and a non-complement factor. A non-complement factor may include phosphatidylserine, pentraxin-3, C-reactive protein (CRP), globular C1q receptor (gC1qR), complement receptor 1 (CR1), β-amyloid, and calreticulin. In some embodiments, the antibodies inhibit the classical complement activation pathway. In certain embodiments, the antibodies further inhibit the alternative pathway. In some embodiments, the antibodies inhibit autoantibody- and complement-dependent cytotoxicity (CDC). In some embodiments, the antibodies inhibit complement-dependent cell-mediated cytotoxicity (CDCC). In some embodiments, the antibodies inhibit B-cell antibody production, dendritic cell maturation, T-cell proliferation, cytokine production, or microglia activation. In some embodiments, the antibodies inhibit the Arthus reaction. In some embodiments, the antibodies inhibit phagocytosis of synapses or nerve endings. In some embodiments, the antibodies inhibit the activation of complement receptor 3 (CR3/C3) expressing cells.

The functional properties of the antibodies of the present disclosure, such as dissociation constants for antigens, inhibition of protein-protein interactions (e.g., C1q-autoantibody interactions), inhibition of autoantibody-dependent and complement-dependent cytotoxicity (CDC), inhibition of complement-dependent cell-mediated cytotoxicity (CDCC), or lesion formation, may, without limitation, be measured in in vitro, ex vivo, or in vivo experiments.

The dissociation constants ($K_D$) of the humanized anti-C1q antibodies for C1q may be less than 125 nM, less than 120 nM, less than 115 nM, less than 110 nM, less than 100 nM, less than 90 nM, less than 80 nM, less than 70 nM, less than 60 nM, less than 50 nM, less than 40 nM, less than 30 nM, less than 20 nM, less than 10 nM, less than 9 nM, less than 8 nM, less than 7 nM, less than 6 nM, less than 5 nM, less than 4 nM, less than 3 nM, less than 2 nM, less than 1 nM, less than 0.5 nM, less than 0.1 nM, less than 0.05 nM, less than 0.01 nM, or less than 0.005 nM. In some embodiments, dissociation constants range from less than about 125 nM to less than about 5 pM.

In some embodiments, dissociation constants of humanized anti-C1q antibodies of the present disclosure are less than about 10 pM to less than about 5 pM for human C1q. In some embodiments, dissociation constants are less than about 10 pM, less than about 9.9 pm, less than about 9.8 pM, less than about 9.7 pM, less than about 9.6 pM, less than about 9.5 pM, less than about 9.4 pM, less than about 9.3 pM, less than about 9.2 pM, less than about 9.1 pM, less than about 9 pM, less than about 8.9 pm, less than about 8.8 pM, less than about 8.7 pM, less than about 8.6 pM, less than about 8.5 pM, less than about 8.4 pM, less than about 8.3 pM, less than about 8.2 pM, less than about 8.1 pM, less than about 8 pM, less than about 7.9 pm, less than about 7.8 pM, less than about 7.7 pM, less than about 7.6 pM, less than about 7.5 pM, less than about 7.4 pM, less than about 7.3 pM, less than about 7.2 pM, less than about 7.1 pM, less than about 7 pM, less than about 6.9 pm, less than about 6.8 pM, less than about 6.7 pM, less than about 6.6 pM, less than about 6.5 pM, less than about 6.4 pM, less than about 6.3 pM, less than about 6.2 pM, less than about 6.1 pM, less than about 6 pM, less than about 5.9 pm, less than about 5.8 pM, less than about 5.7 pM, less than about 5.6 pM, less than about 5.5 pM, less than about 5.4 pM, less than about 5.3 pM, less than about 5.2 pM, less than about 5.1 pM, or less than about 5 pM, for human C1q.

In some embodiments, dissociation constants of humanized anti-C1q antibodies of the present disclosure are less than 125 nM, less than 120 nM, less than 115 nM, less than 110 nM, less than 100 nM, less than 90 nM, less than 80 nM, less than 70 nM, less than 60 nM, less than 50 nM, less than 40 nM, less than 30 nM, less than 20 nM, less than 10 nM, less than 9 nM, less than 8 nM, less than 7 nM, less than 6 nM, less than 5 nM, less than 4 nM, less than 3 nM, less than 2 nM, less than 1 nM, less than 0.5 nM, less than 0.1 nM, or less than 0.05 nM for mouse C1q.

Antibody dissociation constants for antigens other than C1q may be least 5-fold, at least 10-fold, at least 100-fold, at least 1,000-fold, at least 10,000-fold, or at least 100,000-fold higher that the dissociation constants for C1q. For example, the dissociation constant of a humanized anti-C1q antibody of the present disclosure may be at least 1,000-fold higher for C1s than for C1q. Dissociation constants may be determined through any analytical technique, including any biochemical or biophysical technique such as ELISA, surface plasmon resonance (SPR), bio-layer interferometry (see, e.g., Octet System by ForteBio), isothermal titration calorimetry (ITC), differential scanning calorimetry (DSC), circular dichroism (CD), stopped-flow analysis, and colorimetric or fluorescent protein melting analyses. Dissociation constants ($K_D$) of the anti-C1q antibodies for C1q may be determined, e.g., using full-length antibodies or antibody fragments, such as Fab fragments.

One exemplary way of determining binding affinity of humanized antibodies to C1q is by measuring binding affinity of monofunctional Fab fragments of the antibody. To obtain monofunctional Fab fragments, an antibody (for example, IgG) can be cleaved with papain or expressed recombinantly. The affinity of an Fab fragment of an antibody can be determined by surface plasmon resonance (Biacore3000™ surface plasmon resonance (SPR) system, Biacore™, INC, Piscataway N.J.) equipped with pre-immobilized streptavidin sensor chips (SA) using HBS-EP running buffer (0.01M HEPES, pH 7.4, 0.15 NaCl, 3 mM EDTA, 0.005% v/v Surfactant P20). Biotinylated human C1q (or any other C1q) can be diluted into HBS-EP buffer to a concentration of less than 0.5 µg/mL and injected across the individual chip channels using variable contact times, to achieve two ranges of antigen density, either 50-200 response units (RU) for detailed kinetic studies or 800-1,000 RU for screening assays. Regeneration studies have shown that 25 mM NaOH in 25% v/v ethanol effectively removes the bound Fab while keeping the activity of C1q on the chip for over 200 injections. Typically, serial dilutions (spanning concentrations of 0.1-10.times. estimated $K_D$) of purified Fab samples are injected for 1 min at 100 µL/minute and dissociation times of up to 2 hours are allowed. The concentrations of the Fab proteins are determined by ELISA and/or SDS-PAGE electrophoresis using a Fab of known concentration (as determined by amino acid analysis) as a standard. Kinetic association rates ($k_{on}$) and dissociation rates ($k_{off}$) are obtained simultaneously by fitting the data globally to a 1:1 Langmuir binding model (Karlsson, R. Roos, H. Fagerstam, L. Petersson, B. (1994). *Methods Enzymology* 6. 99-110) using the BIAevaluation program. Equilibrium dissociation constant ($K_D$) values are calculated as $k_{off}/k_{on}$. This protocol is suitable for use in determining binding affinity of an antibody to any C1q, including human C1q, C1q of another mammal (such as mouse C1q, rat C1q, primate C1q), as well as different forms of C1q. Binding affinity of an antibody is generally measured at 25° C., but can also be measured at 37° C.

The humanized antibodies of the present disclosure may bind to C1q antigens derived from any organism having a complement system, including any mammalian organism such as human, mouse, rat, rabbit, monkey, dog, cat, cow, horse, camel, sheep, goat, or pig. In some embodiments, the anti-C1q antibodies bind specifically to epitopes on human C1q. In some embodiments, the anti-C1q antibodies specifically bind to epitopes on both human and mouse C1q. In some embodiments, the anti-C1q antibodies specifically bind to epitopes on human, mouse, and rat C1q.

In some embodiments, provided herein is a humanized anti-C1q antibody that binds to an epitope of C1q that is the same as or overlaps with the C1q epitope bound by another antibody of this disclosure. In certain embodiments, provided herein is a humanized anti-C1q antibody that binds to an epitope of C1q that is the same as or overlaps with the C1q epitope bound by anti-C1q antibody M1 produced by the hybridoma cell line with ATCC Accession Number PTA-120399. In some embodiments, the humanized anti-C1q antibody competes with another antibody of this disclosure for binding to C1q. In certain embodiments, the anti-C1q antibody competes with anti-C1q antibody M1 produced by the hybridoma cell line with ATCC Accession Number PTA-120399 or anti-C1q binding fragments thereof.

Methods that may be used to determine which C1q epitope of a humanized anti-C1q antibody binds to, or whether two antibodies bind to the same or an overlapping epitope, may include, without limitation, X-ray crystallography, NMR spectroscopy, Alanine-Scanning Mutagenesis, the screening of peptide libraries that include C1q-derived peptides with overlapping C1q sequences, and competition assays. Competition assays are especially useful to determine whether two antibodies bind the same epitope by recognizing identical or sterically overlapping epitopes or whether one antibody competitively inhibits binding of another antibody to the antigen. These assays are known in the art. Typically, an antigen or antigen expressing cells are immobilized on a multi-well plate and the ability of unlabeled antibodies to block the binding of labeled antibodies is measured. Common labels for such competition assays are radioactive labels or enzyme labels.

Competitive antibodies encompassed herein are humanized antibodies that inhibit (i.e., prevent or interfere with in comparison to a control) or reduce the binding of any anti-C1q antibody of this disclosure (such as M1 or an antigen-binding fragment of M1) to C1q by at least 50%, 60%, 70%, 80%, 90% and 95% at 1 µM or less. For example, the concentration competing antibody in the competition assay may be at or below the $K_D$ of antibody M1 or an antigen-binding fragment of M1. Competition between binding members may be readily assayed in vitro for example using ELISA and/or by monitoring the interaction of the antibodies with C1q in solution. The exact means for conducting the analysis is not critical. C1q may be immobilized to a 96-well plate or may be placed in a homogenous solution. In specific embodiments, the ability of unlabeled candidate antibody(ies) to block the binding of the labeled anti-C1q antibody, e.g. M1, can be measured using radioactive, enzyme or other labels. In the reverse assay, the ability of unlabeled antibodies to interfere with the interaction of a labeled anti-C1q antibody with C1q wherein said labeled anti-C1q antibody, e.g., M1, and C1q are already bound is determined. The readout is through measurement of bound label. C1q and the candidate antibody(ies) may be added in any order or at the same time.

In some embodiments, the humanized anti-C1q antibody inhibits the interaction between C1q and an autoantibody.

In some embodiments, a humanized anti-C1q antibody of the present disclosure binds essentially the same C1q epitope as antibody M1 produced by the hybridoma cell line with ATCC Accession Number PTA-120399 or anti-C1q binding fragments thereof.

In some embodiments, the humanized anti-C1q antibody is an antibody, or an antigen-binding fragment thereof, comprising a heavy chain variable domain comprising an amino acid sequence selected from SEQ ID NOs: 1-4, or an amino acid sequence with at least about 70%, at least about 75%, at least about 80% at least about 85% at least about 90%, or at least about 95% homology to the amino acid sequence selected from SEQ ID NOs: 1-4. In some embodiments, the humanized anti-C1q antibody is an antibody, or an antigen-binding fragment thereof, comprising a light chain variable domain comprising an amino acid sequence selected from SEQ ID NOs: 5-8, or an amino acid sequence with at least about 70%, at least about 75%, at least about 80% at least about 85% at least about 90%, or at least about 95% homology to the amino acid sequence selected from SEQ ID NOs: 5-8. In some embodiments, the humanized anti-C1q antibody is an antibody, or an antigen-binding fragment thereof, comprising a heavy chain variable domain comprising an amino acid sequence selected from SEQ ID NOs: 1-4, or an amino acid sequence with at least about 70%, at least about 75%, at least about 80% at least about 85% at least about 90%, or at least about 95% homology to the amino acid sequence selected from SEQ ID NOs: 1-4; and/or a light chain variable domain comprising an amino acid sequence selected from SEQ ID NOs: 5-8, or an amino acid sequence with at least about 70%, at least about 75%, at least about 80% at least about 85% at least about 90%, or at least about 95% homology to the amino acid sequence selected from SEQ ID NOs: 5-8.

In some embodiments, the humanized anti-C1q antibody, or an antigen-binding fragment thereof, comprises a heavy chain variable domain comprising the amino acid sequence of SEQ ID NO: 1, or an amino acid sequence with at least about 70%, at least about 75%, at least about 80% at least about 85% at least about 90%, or at least about 95% homology to the amino acid sequence of SEQ ID NO: 1; and a light chain variable domain comprising the amino acid sequence of SEQ ID NO: 5, or an amino acid sequence with at least about 70%, at least about 75%, at least about 80% at least about 85% at least about 90%, or at least about 95% homology to the amino acid sequence of SEQ ID NO: 5. In some embodiments, the humanized anti-C1q antibody, or an antigen-binding fragment thereof, comprises a heavy chain variable domain comprising the amino acid sequence of SEQ ID NO: 1, or an amino acid sequence with at least about 70%, at least about 75%, at least about 80% at least about 85% at least about 90%, or at least about 95% homology to the amino acid sequence of SEQ ID NO: 1; and a light chain variable domain comprising the amino acid sequence of SEQ ID NO: 6, or an amino acid sequence with at least about 70%, at least about 75%, at least about 80% at least about 85% at least about 90%, or at least about 95% homology to the amino acid sequence of SEQ ID NO: 6. In some embodiments, the humanized anti-C1q antibody, or an antigen-binding fragment thereof, comprises a heavy chain variable domain comprising the amino acid sequence of SEQ ID NO: 1, or an amino acid sequence with at least about 70%, at least about 75%, at least about 80% at least about 85% at least about 90%, or at least about 95% homology to the amino acid sequence of SEQ ID NO: 1; and a light chain variable domain comprising the amino acid sequence of SEQ ID NO: 7, or an amino acid sequence with at least about 70%, at least about 75%, at least about 80% at least about 85% at least about 90%, or at least about 95% homology to the amino acid sequence of SEQ ID NO: 7. In some embodiments, the humanized anti-C1q antibody, or an antigen-binding fragment thereof, comprises a heavy chain variable domain comprising the amino acid sequence of SEQ ID NO: 1, or an amino acid sequence with at least about 70%, at least about 75%, at least about 80% at least about 85% at least about 90%, or at least about 95% homology to the amino acid sequence of SEQ ID NO: 1; and a light chain variable domain comprising the amino acid sequence of SEQ ID NO: 8, or an amino acid sequence with at least about 70%, at least about 75%, at least about 80% at least about 85% at least about 90%, or at least about 95% homology to the amino acid sequence of SEQ ID NO: 8.

In some embodiments, the humanized anti-C1q antibody, or an antigen-binding fragment thereof, comprises a heavy chain variable domain comprising the amino acid sequence of SEQ ID NO: 2, or an amino acid sequence with at least about 70%, at least about 75%, at least about 80% at least about 85% at least about 90%, or at least about 95% homology to the amino acid sequence of SEQ ID NO: 2; and a light chain variable domain comprising the amino acid sequence of SEQ ID NO: 5, or an amino acid sequence with at least about 70%, at least about 75%, at least about 80% at least about 85% at least about 90%, or at least about 95% homology to the amino acid sequence of SEQ ID NO: 5. In some embodiments, the humanized anti-C1q antibody, or an antigen-binding fragment thereof, comprises a heavy chain variable domain comprising the amino acid sequence of SEQ ID NO: 2, or an amino acid sequence with at least about 70%, at least about 75%, at least about 80% at least about 85% at least about 90%, or at least about 95% homology to the amino acid sequence of SEQ ID NO: 2; and a light chain variable domain comprising the amino acid sequence of SEQ ID NO: 6, or an amino acid sequence with at least about 70%, at least about 75%, at least about 80% at least about 85% at least about 90%, or at least about 95% homology to the amino acid sequence of SEQ ID NO: 6. In some embodiments, the humanized anti-C1q antibody, or an antigen-binding fragment thereof, comprises a heavy chain variable domain comprising the amino acid sequence of SEQ ID NO: 2, or an amino acid sequence with at least about 70%, at least about 75%, at least about 80% at least about 85% at least about 90%, or at least about 95% homology to the amino acid sequence of SEQ ID NO: 2; and a light chain variable domain comprising the amino acid sequence of SEQ ID NO: 7, or an amino acid sequence with at least about 70%, at least about 75%, at least about 80% at least about 85% at least about 90%, or at least about 95% homology to the amino acid sequence of SEQ ID NO: 7. In some embodiments, the humanized anti-C1q antibody, or an antigen-binding fragment thereof, comprises a heavy chain variable domain comprising the amino acid sequence of SEQ ID NO: 2, or an amino acid sequence with at least about 70%, at least about 75%, at least about 80% at least about 85% at least about 90%, or at least about 95% homology to the amino acid sequence of SEQ ID NO: 2; and a light chain variable domain comprising the amino acid sequence of SEQ ID NO: 8, or an amino acid sequence with at least about 70%, at least about 75%, at least about 80% at least about 85% at least about 90%, or at least about 95% homology to the amino acid sequence of SEQ ID NO: 8.

In some embodiments, the humanized anti-C1q antibody, or an antigen-binding fragment thereof, comprises a heavy chain variable domain comprising the amino acid sequence of SEQ ID NO: 3, or an amino acid sequence with at least about 70%, at least about 75%, at least about 80% at least about 85% at least about 90%, or at least about 95% homology to the amino acid sequence of SEQ ID NO: 3; and a light chain variable domain comprising the amino acid sequence of SEQ ID NO: 5, or an amino acid sequence with at least about 70%, at least about 75%, at least about 80% at least about 85% at least about 90%, or at least about 95% homology to the amino acid sequence of SEQ ID NO: 5. In some embodiments, the humanized anti-C1q antibody, or an antigen-binding fragment thereof, comprises a heavy chain variable domain comprising the amino acid sequence of SEQ ID NO: 3, or an amino acid sequence with at least about 70%, at least about 75%, at least about 80% at least about 85% at least about 90%, or at least about 95% homology to the amino acid sequence of SEQ ID NO: 3; and a light chain variable domain comprising the amino acid sequence of SEQ ID NO: 6, or an amino acid sequence with at least about 70%, at least about 75%, at least about 80% at least about 85% at least about 90%, or at least about 95% homology to the amino acid sequence of SEQ ID NO: 6. In some embodiments, the humanized anti-C1q antibody, or an antigen-binding fragment thereof, comprises a heavy chain variable domain comprising the amino acid sequence of SEQ ID NO: 3, or an amino acid sequence with at least about 70%, at least about 75%, at least about 80% at least about 85% at least about 90%, or at least about 95% homology to the amino acid sequence of SEQ ID NO: 3; and a light chain variable domain comprising the amino acid sequence of SEQ ID NO: 7, or an amino acid sequence with at least about 70%, at least about 75%, at least about 80% at least about 85% at least about 90%, or at least about 95% homology to the amino acid sequence of SEQ ID NO: 7. In some embodiments, the humanized anti-C1q antibody, or an antigen-binding fragment thereof, comprises a heavy chain variable domain comprising the amino acid sequence of SEQ ID NO: 3, or an amino acid sequence with at least about 70%, at least about 75%, at least about 80% at least about 85% at least about 90%, or at least about 95% homology to the amino acid sequence of SEQ ID NO: 3; and a light chain variable domain comprising the amino acid sequence of SEQ ID NO: 8, or an amino acid sequence with at least about 70%, at least about 75%, at least about 80% at least about 85% at least about 90%, or at least about 95% homology to the amino acid sequence of SEQ ID NO: 8.

In some embodiments, the humanized anti-C1q antibody, or an antigen-binding fragment thereof, comprises a heavy chain variable domain comprising the amino acid sequence of SEQ ID NO: 4, or an amino acid sequence with at least about 70%, at least about 75%, at least about 80% at least about 85% at least about 90%, or at least about 95% homology to the amino acid sequence of SEQ ID NO: 4; and a light chain variable domain comprising the amino acid sequence of SEQ ID NO: 5, or an amino acid sequence with at least about 70%, at least about 75%, at least about 80% at least about 85% at least about 90%, or at least about 95% homology to the amino acid sequence of SEQ ID NO: 5. In some embodiments, the humanized anti-C1q antibody, or an antigen-binding fragment thereof, comprises a heavy chain variable domain comprising the amino acid sequence of SEQ ID NO: 4, or an amino acid sequence with at least about 70%, at least about 75%, at least about 80% at least about 85% at least about 90%, or at least about 95% homology to the amino acid sequence of SEQ ID NO: 4; and a light chain variable domain comprising the amino acid sequence of SEQ ID NO: 6, or an amino acid sequence with at least about 70%, at least about 75%, at least about 80% at least about 85% at least about 90%, or at least about 95% homology to the amino acid sequence of SEQ ID NO: 6. In some embodiments, the humanized anti-C1q antibody, or an antigen-binding fragment thereof, comprises a heavy chain variable domain comprising the amino acid sequence of SEQ ID NO: 4, or an amino acid sequence with at least about 70%, at least about 75%, at least about 80% at least about 85% at least about 90%, or at least about 95% homology to the amino acid sequence of SEQ ID NO: 4; and a light chain variable domain comprising the amino acid sequence of SEQ ID NO: 7, or an amino acid sequence with at least about 70%, at least about 75%, at least about 80% at least about 85% at least about 90%, or at least about 95% homology to the amino acid sequence of SEQ ID NO: 7. In some embodiments, the humanized anti-C1q antibody, or an antigen-binding fragment thereof, comprises a heavy chain variable domain comprising the amino acid sequence of SEQ ID NO: 4, or an amino acid sequence with at least about 70%, at least about 75%, at least about 80% at least about 85% at least about 90%, or at least about 95% homology to the amino acid sequence of SEQ ID NO: 4; and a light chain variable domain comprising the amino acid sequence of SEQ ID NO: 8, or an amino acid sequence with at least about 70%, at least about 75%, at least about 80% at least about 85% at least about 90%, or at least about 95% homology to the amino acid sequence of SEQ ID NO: 8.

In some embodiments, humanized anti-C1q antibodies of the present disclosure may comprise at least one HVR selected from HVR-L1, HVR-L2, and HVR-L3 of the light chain variable domains of monoclonal antibody M1 produced by the hybridoma cell line having ATCC Accession Number PTA-120399, or progeny thereof. In some embodiments, humanized anti-C1q antibodies of the present disclosure may comprise at least one HVR selected from HVR-H1, HVR-H2, and HVR-H3 of the heavy chain variable domains of monoclonal antibody M1 produced by the hybridoma cell line having ATCC Accession Number PTA-120399, or progeny thereof. In some embodiments, humanized anti-C1q antibodies of the present disclosure may comprise at least one HVR selected from HVR-L1, HVR-L2, and HVR-L3 of the light chain variable domains and at least one HVR selected from HVR-H1, HVR-H2, and HVR-H3 of the heavy chain variable domains of monoclonal antibody M1 produced by the hybridoma cell line having ATCC Accession Number PTA-120399, or progeny thereof.

In some embodiments, humanized anti-C1q antibodies of the present disclosure may bind to a C1q protein and binds to one or more amino acids of the C1q protein within amino acid residues selected from (a) amino acid residues 196-226 of SEQ ID NO: 9 (SEQ ID NO:12), or amino acid residues of a C1q protein chain A (C1qA) corresponding to amino acid residues 196-226 (GLFQVVSGGMV-LQLQQGDQVWVEKDPKKGHI) of SEQ ID NO: 9 (SEQ ID NO:12); (b) amino acid residues 196-221 of SEQ ID NO: 9 (SEQ ID NO:13), or amino acid residues of a C1qA corresponding to amino acid residues 196-221 (GLFQV-VSGGMVLQLQQGDQVWVEKDP) of SEQ ID. NO: 9 (SEQ ID NO:13); (c) amino acid residues 202-221 of SEQ ID NO: 9 (SEQ ID NO:14), or amino acid residues of a C1qA corresponding to amino acid residues 202-221 (SGGMVLQLQQGDQVWVEKDP) of SEQ ID NO: 9 (SEQ ID NO:14); (d) amino acid residues 202-219 of SEQ ID NO: 9 (SEQ ID NO:15), or amino acid residues of a C1qA corresponding to amino acid residues 202-219

(SGGMVLQLQQGDQVWVEK) of SEQ ID NO: 9 (SEQ ID NO:15); and (e) amino acid residues Lys 219 and/or Ser 202 of SEQ ID NO: 9, or amino acid residues of a C1qA corresponding Lys 219 and/or Ser 202 of SEQ ID NO: 9.

In some embodiments, the humanized anti-C1q antibodies may further binds to one or more amino acids of the C1q protein within amino acid residues selected from: (a) amino acid residues 218-240 of SEQ ID NO: 11 (SEQ ID NO:16) or amino acid residues of a C1q protein chain C (C1qC) corresponding to amino acid residues 218-240 (WLAVN-DYYDMVGI QGSDSVFSGF) of SEQ ID NO: 11 (SEQ ID NO:16); (b) amino acid residues 225-240 of SEQ ID NO: 11 (SEQ ID NO:17) or amino acid residues of a C1qC corresponding to amino acid residues 225-240 (YDMVGI QGSDSVFSGF) of SEQ ID NO: 11 (SEQ ID NO:17); (c) amino acid residues 225-232 of SEQ ID NO: 11 (SEQ ID NO:18) or amino acid residues of a C1qC corresponding to amino acid residues 225-232 (YDMVGIQG) of SEQ ID NO: 11 (SEQ ID NO:18); (d) amino acid residue Tyr 225 of SEQ ID NO: 11 or an amino acid residue of a C1qC corresponding to amino acid residue Tyr 225 of SEQ ID NO: 11; (e) amino acid residues 174-196 of SEQ ID NO: 11 (SEQ ID NO:19) or amino acid residues of a C1qC corresponding to amino acid residues 174-196 (HTANLCVLLYRSGVK-VVTFCGHT) of SEQ ID NO: 11 (SEQ ID NO:19); (f) amino acid residues 184-192 of SEQ ID NO: 11 (SEQ ID NO:20) or amino acid residues of a C1qC corresponding to amino acid residues 184-192 (RSGVKVVTF) of SEQ ID NO: 11 (SEQ ID NO:20); (g) amino acid residues 185-187 of SEQ ID NO: 11 or amino acid residues of a C1qC corresponding to amino acid residues 185-187 (SGV) of SEQ ID NO: 11; (h) amino acid residue Ser 185 of SEQ ID NO: 11 or an amino acid residue of a C1qC corresponding to amino acid residue Ser 185 of SEQ ID NO: 11.

In certain embodiments, humanized anti-C1q antibodies of the present disclosure may bind to amino acid residue Lys 219 and Ser 202 of the human C1qA as shown in SEQ ID NO: 9 or amino acids of a human C1qA corresponding to Lys 219 and Ser 202 as shown in SEQ ID NO: 9, and amino acid residue Tyr 225 of the human C1qC as shown in SEQ ID NO: 11 or an amino acid residue of a human C1qC corresponding to Tyr 225 as shown in SEQ ID NO: 11. In certain embodiments, the anti-C1q antibody binds to amino acid residue Lys 219 of the human C1qA as shown in SEQ ID NO: 9 or an amino acid residue of a human C1qA corresponding to Lys 219 as shown in SEQ ID NO: 9, and amino acid residue Ser 185 of the human C1qC as shown in SEQ ID NO: 11 or an amino acid residue of a human C1qC corresponding to Ser 185 as shown in SEQ ID NO: 11.

In some embodiments, humanized anti-C1q antibodies of the present disclosure may bind to a C1q protein and binds to one or more amino acids of the C1q protein within amino acid residues selected from: (a) amino acid residues 218-240 of SEQ ID NO: 11 (SEQ ID NO:16) or amino acid residues of a C1qC corresponding to amino acid residues 218-240 (WLAVNDYYDMVGI QGSDSVFSGF) of SEQ ID NO: 11 (SEQ ID NO:16); (b) amino acid residues 225-240 of SEQ ID NO: 11 (SEQ ID NO:17) or amino acid residues of a C1qC corresponding to amino acid residues 225-240 (YDM-VGI QGSDSVFSGF) of SEQ ID NO: 11 (SEQ ID NO:17); (c) amino acid residues 225-232 of SEQ ID NO: 11 (SEQ ID NO:18) or amino acid residues of a C1qC corresponding to amino acid residues 225-232 (YDMVGIQG) of SEQ ID NO: 11 (SEQ ID NO:18); (d) amino acid residue Tyr 225 of SEQ ID NO: 11 or an amino acid residue of a C1qC corresponding to amino acid residue Tyr 225 of SEQ ID NO: 11; (e) amino acid residues 174-196 of SEQ ID NO: 11 (SEQ ID NO:19) or amino acid residues of a C1qC corresponding to amino acid residues 174-196 (HTANLCVLLYRSGVK-VVTFCGHT) of SEQ ID NO: 11 (SEQ ID NO:19); (f) amino acid residues 184-192 of SEQ ID NO: 11 (SEQ ID NO:20) or amino acid residues of a C1qC corresponding to amino acid residues 184-192 (RSGVKVVTF) of SEQ ID NO: 11 (SEQ ID NO:20); (g) amino acid residues 185-187 of SEQ ID NO: 11 or amino acid residues of a C1qC corresponding to amino acid residues 185-187 (SGV) of SEQ ID NO: 11; (h) amino acid residue Ser 185 of SEQ ID NO: 11 or an amino acid residue of a C1qC corresponding to amino acid residue Ser 185 of SEQ ID NO: 11.

In some embodiments, a humanized anti-C1q antibody of the present disclosure inhibits the interaction between C1q and C1s. In some embodiments, the humanized anti-C1q antibody inhibits the interaction between C1q and C1r. In some embodiments the humanized anti-C1q antibody inhibits the interaction between C1q and C1s and between C1q and C1r. In some embodiments, the humanized anti-C1q antibody inhibits the interaction between C1q and another antibody, such as an autoantibody. In some embodiments, the humanized anti-C1q antibody inhibits the respective interactions, at a stoichiometry of less than 2.5:1; 2.0:1; 1.5:1; or 1.0:1. In some embodiments, the humanized C1q antibody inhibits an interaction, such as the C1q-C1s interaction, at approximately equimolar concentrations of C1q and the anti-C1q antibody. In other embodiments, the anti-C1q antibody binds to C1q with a stoichiometry of less than 20:1; less than 19.5:1; less than 19:1; less than 18.5:1; less than 18:1; less than 17.5:1; less than 17:1; less than 16.5:1; less than 16:1; less than 15.5:1; less than 15:1; less than 14.5:1; less than 14:1; less than 13.5:1; less than 13:1; less than 12.5:1; less than 12:1; less than 11.5:1; less than 11:1; less than 10.5:1; less than 10:1; less than 9.5:1; less than 9:1; less than 8.5:1; less than 8:1; less than 7.5:1; less than 7:1; less than 6.5:1; less than 6:1; less than 5.5:1; less than 5:1; less than 4.5:1; less than 4:1; less than 3.5:1; less than 3:1; less than 2.5:1; less than 2.0:1; less than 1.5:1; or less than 1.0:1. In certain embodiments, the humanized anti-C1q antibody binds C1q with a binding stoichiometry that ranges from 20:1 to 1.0:1 or less than 1.0:1. In certain embodiments, the humanized anti-C1q antibody binds C1q with a binding stoichiometry that ranges from 6:1 to 1.0:1 or less than 1.0:1. In certain embodiments, the humanized anti-C1q antibody binds C1q with a binding stoichiometry that ranges from 2.5:1 to 1.0:1 or less than 1.0:1. In some embodiments, an anti-C1q antibody of the present disclosure having a binding stoichiometry for C1q of 1.0:1 yields approximately 50% inhibition of C1F hemolysis, as determined for example by CH50 assays of the present disclosure. In some embodiments, the humanized anti-C1q antibody inhibits the interaction between C1q and C1r, or between C1q and C1s, or between C1q and both C1r and C1s. In some embodiments, the humanized anti-C1q antibody inhibits the interaction between C1q and C1r, between C1q and C1s, and/or between C1q and both C1r and C1s. In some embodiments, the humanized anti-C1q antibody binds to the C1q A-chain. In other embodiments, the humanized anti-C1q antibody binds to the C1q B-chain. In other embodiments, the humanized anti-C1q antibody binds to the C1q C-chain. In some embodiments, the humanized anti-C1q antibody binds to the C1q A-chain, the C1q B-chain and/or the C1q C-chain. In some embodiments, the humanized anti-C1q antibody binds to the globular domain of the C1q A-chain, B-chain, and/or C-chain. In other embodiments, the humanized anti-C1q antibody binds to the collagen-like domain of the C1q A-chain, the C1q B-chain, and/or the C1q C-chain.

Where humanized antibodies of this disclosure inhibit the interaction between two or more complement factors, such as the interaction of C1q and C1s, or the interaction between C1q and C1r, the interaction occurring in the presence of the antibody may be reduced by at least 10%, at least 20%, at least 30%, at least 40%, at least 50%, at least 60%, at least 70%, at least 80%, at least 90%, at least 95%, or at least 99% relative to a control wherein the antibodies of this disclosure are absent. In certain embodiments, the interaction occurring in the presence of the humanized antibody is reduced by an amount that ranges from at least 30% to at least 99% relative to a control wherein the humanized antibodies of this disclosure are absent.

In some embodiments, humanized anti-C1q antibodies of the present disclosure inhibit C4-cleavage by at least 20%, at least 30%, at least 40%, at least 50%, at least 60%, at least 70%, at least 80%, at least 90%, at least 95%, or at least 99%, or by an amount that ranges from at least 30% to at least 99%, relative to a control wherein the antibodies of this disclosure are absent. Methods for measuring C4-cleavage are well known in the art. The $EC_{50}$ values for antibodies of this disclosure with respect C4-cleavage may be less than 3 µg/ml; 2.5 µg/ml; 2.0 µg/ml; 1.5 µg/ml; 1.0 µg/ml; 0.5 µg/ml; 0.25 µg/ml; 0.1 µg/ml; 0.05 µg/ml. In some embodiments, the antibodies of this disclosure inhibit C4-cleavage at approximately equimolar concentrations of C1q and the respective anti-C1q antibody.

In some embodiments, humanized anti-C1q antibodies of the present disclosure inhibit autoantibody-dependent and complement-dependent cytotoxicity (CDC) by at least 20%, at least 30%, at least 40%, at least 50%, at least 60%, at least 70%, at least 80%, at least 90%, at least 95%, or at least 99%, or by an amount that ranges from at least 30% to at least 99%, relative to a control wherein the antibodies of this disclosure are absent. The $EC_{50}$ values for antibodies of this disclosure with respect to inhibition of autoantibody-dependent and complement-dependent cytotoxicity may be less than 3 µg/ml; 2.5 µg/ml; 2.0 µg/ml; 1.5 µg/ml; 1.0 µg/ml; 0.5 µg/ml; 0.25 µg/ml; 0.1 µg/ml; 0.05 µg/ml.

In some embodiments, humanized anti-C1q antibodies of the present disclosure inhibit complement-dependent cell-mediated cytotoxicity (CDCC) by at least 20%, at least 30%, at least 40%, at least 50%, at least 60%, at least 70%, at least 80%, at least 90%, at least 95%, or at least 99%, or by an amount that ranges from at least 30% to at least 99%, relative to a control wherein the antibodies of this disclosure are absent. Methods for measuring CDCC are well known in the art. The $EC_{50}$ values for antibodies of this disclosure with respect CDCC inhibition may be 1 less than 3 µg/ml; 2.5 µg/ml; 2.0 µg/ml; 1.5 µg/ml; 1.0 µg/ml; 0.5 µg/ml; 0.25 µg/ml; 0.1 µg/ml; 0.05 µg/ml. In some embodiments, the antibodies of this disclosure inhibit CDCC but not antibody-dependent cellular cytotoxicity (ADCC).

In some embodiments, humanized anti-C1q antibodies of the present disclosure inhibit C1F hemolysis (also referred to as CH50 hemolysis) by at least 20%, at least 30%, at least 40%, at least 50%, at least 60%, at least 70%, at least 80%, at least 90%, at least 95%, or at least 99%, or by an amount that ranges from at least 30% to at least 99%, relative to a control wherein the antibodies of this disclosure are absent or wherein control antibodies are used that do not bind to a complement factor or another antibody such as an autoantibody (see, e.g., Examples section below). Methods for measuring C1F hemolysis are well known in the art (see, e.g., Examples section below). The $EC_{50}$ values for humanized antibodies of this disclosure with respect to C1F hemolysis may be less than 3 µg/ml; 2.5 µg/ml; 2.0 µg/ml; 1.5 µg/ml; 1.0 µg/ml; 0.5 µg/ml; 0.25 µg/ml; 0.1 µg/ml; 0.05 µg/ml. In some embodiments, humanized anti-C1q antibodies of this disclosure neutralize at least 50% of C1F hemolysis at a dose of less than 200 ng/ml, less than 100 ng/ml, less than 50 ng/ml, or less than 20 ng/ml. In some embodiments, humanized antibodies of this disclosure neutralize C1F hemolysis at approximately equimolar concentrations of C1q and the anti-C1q antibody. In some embodiments, humanized anti-C1q antibodies of this disclosure neutralize hemolysis in a human C1F hemolysis assay. In some embodiments, humanized anti-C1q antibodies of this disclosure neutralize hemolysis in a human and rat C1F hemolysis assay (see, e.g., see, e.g., Examples section below).

In some embodiments, the alternative pathway may amplify CDC initiated by C1q binding and subsequent C1s activation; in at least some of these embodiments, the antibodies of this disclosure inhibit the alternative pathway by at least 30%, at least 40%, at least 50%, at least 60%, at least 70%, at least 80%, at least 90%, at least 95%, or at least 99%, or by an amount that ranges from at least 30% to at least 99%, relative to a control wherein the antibodies of this disclosure were absent.

In some embodiments, humanized anti-C1q antibodies of the present disclosure prevent synaptic loss in a cellular in vitro model or an in vivo model of synaptic loss, such as an in vivo mouse model. In vivo mouse models may include Tg2576, a mouse amyloid precursor protein (APP) transgenic model of Alzheimer's disease, R6/2 NT-CAG150, a transgenic model for Huntington's disease, or SMA□7, a mouse model for Spinal Muscular Atrophy, or DBA/2J, a genetic mouse model of glaucoma. In general, any neurodegenerative disease model may be used that displays synapse loss.

Methods for measuring synaptic loss in vitro or in vivo are well known in the art. In vitro lesion formation may be reduced by at least 30%, at least 40%, at least 50%, at least 60%, at least 70%, at least 80%, at least 90%, or at least 95%, or by an amount that ranges from at least 30% to at least 95%, relative to a control experiment in which antibodies of this disclosure are absent. The $EC_{50}$ values for antibodies of this disclosure with respect to the prevention of in vitro lesion formation may be less than 3 µg/ml; 2.5 µg/ml; 2.0 µg/ml; 1.5 µg/ml; 1.0 µg/ml; 0.5 µg/ml; 0.25 µg/ml; 0.1 µg/ml; 0.05 µg/ml. In vivo synaptic loss may be reduced by at least 5%, at least 10%, at least 15%, at least 20%, at least 35%, at least 40%, or at least 50%, or by an amount that ranges from at least 5% to at least 50%, relative to a control experiment in which antibodies of this disclosure are absent.

In some embodiments, humanized anti-C1q antibodies of the present disclosure prevent lesion formation in an ex vivo spinal cord slice model of NMO or in an in vivo mouse model of NMO. Methods for measuring lesion formation ex vivo or in vivo are well known in the art. Ex vivo lesion formation may be reduced at least by a relative score of 0.5, 1.0, 1.5, 2.0, 2.5, 3.0, 3.5, or 4.0. The $EC_{50}$ values for antibodies of this disclosure with respect to the prevention of ex vivo lesion formation may be less than 3 m/ml; less than 2.5 µg/ml; less than 2.0 µg/ml; less than 1.5 µg/ml; less than 1.0 µg/ml; less than 0.5 µg/ml; less than 0.25 µg/ml; less than 0.1 µg/ml; or less than 0.05 µg/ml. In vivo lesion formation may be reduced by at least 5%, at least 10%, at least 15%, at least 20%, at least 35%, at least 40%, or at least 50%, or by an amount that ranges from at least 5% to at least 50%, in terms of loss of staining (% of area). Staining may be assessed, without limitation, by APQ4 staining, GFAP staining, or MBP staining.

The present disclosure provides humanized anti-C1q antibodies. The humanized antibodies of the present disclosure may have one or more of the following characteristics. The antibodies of this disclosure may be polyclonal antibodies, monoclonal antibodies, chimeric antibodies, human antibodies, antibody fragments, bispecific and polyspecific antibodies, multivalent antibodies, or heteroconjugate antibodies. Antibody fragments of this disclosure may be functional fragments that bind the same epitope as any of the humanized anti-C1q antibodies of this disclosure. In some embodiments, the antibody fragments of this disclosure specifically bind to and neutralize a biological activity of C1q. In some embodiments, the antibody fragments are miniaturized versions of the humanized anti-C1q antibodies or antibody fragments of this disclosure that have the same epitope of the corresponding full-length antibody, but have much smaller molecule weight. Such miniaturized anti-C1q antibody fragments may have better brain penetration ability and a shorter half-life, which is advantageous for imaging and diagnostic utilities (see e.g., Lütje S et al., *Bioconjug Chem.* 2014 Feb. 19; 25(2):335-41; Tavaré R et al., *Proc Natl Acad Sci USA.* 2014 Jan. 21; 111(3):1108-13; and Wiehr S et al., *Prostate.* 2014 May; 74(7):743-55). Accordingly, in some embodiments, humanized anti-C1q antibody fragments of this disclosure have better brain penetration as compared to their corresponding full-length antibodies and/or have a shorter half-life as compared to their corresponding full-length antibodies. In some embodiments, humanized anti-C1q antibodies of the present disclosure are bispecific antibodies recognizing a first antigen and a second antigen. In some embodiments, the first antigen is a C1q antigen. In some embodiments, the second antigen is an antigen facilitating transport across the blood-brain-barrier, including without limitation, transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopep peptide, and ANG1005.

Humanized anti-C1q antibodies of the present disclosure may further contain engineered effector functions, amino acid sequence modifications or other antibody modifications known in the art; e.g., the constant region of the anti-C1q antibodies described herein may be modified to impair complement activation. For example, and without wishing to be bound by theory, unlike the Fc region of human IgG1, IgG2, and IgG3, the Fc region of human IgG4 does not bind to C1q. Accordingly, in some embodiments, humanized anti-C1q antibodies of this disclosure may further comprise the Fc region of human IgG4. In some embodiments, humanized anti-C1q antibodies of this disclosure comprise one or more amino acid substitutions within the Fc region that, for example, prevent arm switching and/or reduces or otherwise inhibits the ability of Fc region from interacting with Fc receptors expressed on cells (see e.g., Angal S et al., *Mol. Immunol.* 1993 January; 30(1):105-8; and Morgan A et al., *Immunology* 1995 86 319-324). In some embodiments humanized anti-C1q antibodies of this disclosure comprise an Fc region that comprises an amino acid substitution at position 241 or 248 according to Kabat numbering convention. In some embodiments, the Fc region comprises a serine to proline amino acid substitution at position 241 that prevent arm switching. In some embodiments, the Fc region comprises a serine to proline amino acid substitution at position 241 according to Kabat numbering convention. In some embodiments, the Fc region comprises a serine to proline amino acid substitution at position 248 that reduces or otherwise inhibits the ability of Fc region from interacting with an Fc receptor. In some embodiments, the Fc region comprises a leucine to glutamate amino acid substitution at position 248 according to Kabat numbering convention. In some embodiments humanized anti-C1q antibodies of this disclosure comprise an Fc region comprising the amino acid sequence of SEQ ID NO: 37.

Additional humanized anti-C1q antibodies, e.g., humanized antibodies that specifically bind to a C1q protein of the present disclosure, may be identified, screened, and/or characterized for their physical/chemical properties and/or biological activities by various assays known in the art.

Antibody Preparation

Anti-C1q antibodies of the present disclosure may be produced using any methods described herein or known in the art. Monoclonal antibodies (e.g., humanized antibodies) of the of the present disclosure can be produced using a variety of known techniques, such as the standard somatic cell hybridization technique described by Kohler and Milstein, Nature 256: 495 (1975). Although somatic cell hybridization procedures are preferred, in principle, other techniques for producing monoclonal antibodies also can be employed, e.g., viral or oncogenic transformation of B lymphocytes and phage display technique using libraries of human antibody genes.

One method for generating hybridomas which produce monoclonal antibodies of the present disclosure is the murine system. Hybridoma production in the mouse is well-known in the art, including immunization protocols and techniques for isolating and fusing immunized splenocytes.

Polyclonal antibodies can be prepared by immunizing a suitable subject with a polypeptide immunogen. The polypeptide antibody titer in the immunized subject can be monitored over time by standard techniques, such as with an enzyme linked immunosorbent assay (ELISA) using immobilized polypeptide. If desired, the antibody directed against the antigen can be isolated from the mammal (e.g., from the blood) and further purified by well-known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also Brown et al. (1981) *J. Immunol.* 127:539-46; Brown et al. (1980) *J. Biol. Chem.* 255:4980-83; Yeh et al. (1976) *Proc. Natl. Acad. Sci.* 76:2927-31; and Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985) *Monoclonal Antibodies and Cancer Therapy*, Alan R. Liss, Inc., pp. 77-96) or trioma techniques. The technology for producing monoclonal antibody hybridomas is well-known (see generally Kenneth, R. H. in *Monoclonal Antibodies: A New Dimension In Biological Analyses*, Plenum Publishing Corp., New York, N.Y. (1980); Lerner, E. A. (1981) *Yale J. Biol. Med.* 54:387-402; Gefter, M. L. et al. (1977) *Somatic Cell Genet.* 3:231-36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, preferably specifically.

Any of the many well-known protocols used for fusing lymphocytes and immortalized cell lines can be applied for the purpose of generating an anti-PD-1, PD-L1, or PD-L2 monoclonal antibody (see, e.g., Galfre, G. et al. (1977) Nature 266:55052; Gefter et al. (1977) supra; Lerner (1981) supra; Kenneth (1980) supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present disclosure with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the present disclosure are detected by screening the hybridoma culture supernatants for antibodies that bind a given polypeptide, e.g., using a standard ELISA assay.

As an alternative to preparing monoclonal antibody-secreting hybridomas, a monoclonal specific for a desired polypeptide (e.g., C1q) can be identified and isolated by screening a recombinant combinatorial immunoglobulin library (e.g., an antibody phage display library) with the appropriate polypeptide to thereby isolate immunoglobulin library members that bind the polypeptide. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening an antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) Biotechnology (NY) 9:1369-1372; Hay et al. (1992) Hum. Antibod. Hybridomas 3:81-85; Huse et al. (1989) Science 246:1275-1281; Griffiths et al. (1993) EMBO J. 12:725-734; Hawkins et al. (1992) J. Mol. Biol. 226:889-896; Clarkson et al. (1991) Nature 352:624-628; Gram et al. (1992) Proc. Natl. Acad. Sci. USA 89:3576-3580; Garrard et al. (1991) Biotechnology (NY) 9:1373-1377; Hoogenboom et al. (1991) Nucleic Acids Res. 19:4133-4137; Barbas et al. (1991) Proc. Natl. Acad. Sci. USA 88:7978-7982; and McCafferty et al. (1990) Nature 348:552-554.

Additionally, recombinant anti-C1q antibodies, such as humanized and chimeric monoclonal antibodies, which can be made using standard recombinant DNA techniques, can be generated. Such humanized and chimeric monoclonal antibodies can be produced by recombinant DNA techniques known in the art, for example using methods described in Robinson et al. International Patent Publication PCT/US86/02269; Akira et al. European Patent Application 184,187; Taniguchi, M. European Patent Application 171,496; Morrison et al. European Patent Application 173,494; Neuberger et al. PCT Application WO 86/01533; Cabilly et al. U.S. Pat. No. 4,816,567; Cabilly et al. European Patent Application 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. 84:214-218; Nishimura et al. (1987) Cancer Res. 47:999-1005; Wood et al. (1985) Nature 314:446-449; and Shaw et al. (1988) J. Natl. Cancer Inst. 80:1553-1559); Morrison, S. L. (1985) Science 229:1202-1207; Oi et al. (1986) Biotechniques 4:214; Winter U.S. Pat. No. 5,225,539; Jones et al. (1986) Nature 321:552-525; Verhoeyan et al. (1988) Science 239:1534; and Beidler et al. (1988) J. Immunol. 141:4053-4060.

In addition, humanized antibodies can be made according to standard protocols such as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable generic display package and vectors containing nucleic acid molecules encoding a second polypeptide chain of a single binding pair member using techniques known in the art, e.g., as described in U.S. Pat. Nos. 5,565,332, 5,871,907, or U.S. Pat. No. 5,733,743. The use of intracellular antibodies to inhibit protein function in a cell is also known in the art (see e.g., Carlson, J. R. (1988) Mol. Cell. Biol. 8:2638-2646; Biocca, S. et al. (1990) EMBO J. 9:101-108; Werge, T. M. et al. (1990) FEBS Lett. 274:193-198; Carlson, J. R. (1993) Proc. Natl. Acad. Sci. USA 90:7427-7428; Marasco, W. A. et al. (1993) Proc. Natl. Acad. Sci. USA 90:7889-7893; Biocca, S. et al. (1994) Biotechnology (NY) 12:396-399; Chen, S-Y. et al. (1994) Hum. Gene Ther. 5:595-601; Duan, L et al. (1994) Proc. Natl. Acad. Sci. USA 91:5075-5079; Chen, S-Y. et al. (1994) Proc. Natl. Acad. Sci. USA 91:5932-5936; Beerli, R. R. et al. (1994) J. Biol. Chem. 269:23931-23936; Beerli, R. R. et al. (1994) Biochem. Biophys. Res. Commun. 204:666-672; Mhashilkar, A. M. et al. (1995) EMBO J. 14:1542-1551; Richardson, J. H. et al. (1995) Proc. Natl. Acad. Sci. USA 92:3137-3141; PCT Publication No. WO 94/02610 by Marasco et al.; and PCT Publication No. WO 95/03832 by Duan et al.).

In another embodiment, human monoclonal anti-C1q antibodies can be generated using transgenic or transchromosomal mice carrying parts of the human immune system rather than the mouse system. In one embodiment, transgenic mice, referred to herein as "HuMAb mice" which contain a human immunoglobulin gene miniloci that encodes unrearranged human heavy ($\mu$ and $\gamma$) and $\kappa$ light chain immunoglobulin sequences, together with targeted mutations that inactivate the endogenous $\mu$ and $\kappa$ chain loci (Lonberg, N. et al. (1994) Nature 368(6474): 856 859). Accordingly, the mice exhibit reduced expression of mouse IgM or $\kappa$, and in response to immunization, the introduced human heavy and light chain transgenes undergo class switching and somatic mutation to generate high affinity human IgG$\kappa$ monoclonal antibodies (Lonberg, N. et al.

(1994), supra; reviewed in Lonberg, N. (1994) Handbook of Experimental Pharmacology 113:49 101; Lonberg, N. and Huszar, D. (1995) Intern. Rev. Immunol. Vol. 13: 65 93, and Harding, F. and Lonberg, N. (1995) Ann. N. Y Acad. Sci 764:536 546). The preparation of HuMAb mice is described in Taylor, L. et al. (1992) Nucleic Acids Research 20:6287 6295; Chen, J. et al. (1993) International Immunology 5: 647 656; Tuaillon et al. (1993) Proc. Natl. Acad. Sci USA 90:3720 3724; Choi et al. (1993) Nature Genetics 4:117 123; Chen, J. et al. (1993) EMBO J. 12: 821 830; Tuaillon et al. (1994) J. Immunol. 152:2912 2920; Lonberg et al., (1994) Nature 368(6474): 856 859; Lonberg, N. (1994) Handbook of Experimental Pharmacology 113:49 101; Taylor, L. et al. (1994) International Immunology 6: 579 591; Lonberg, N. and Huszar, D. (1995) Intern. Rev. Immunol. Vol. 13: 65 93; Harding, F. and Lonberg, N. (1995) Ann. N.Y. Acad. Sci 764:536 546; Fishwild, D. et al. (1996) Nature Biotechnology 14: 845 851. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay, and GenPharm International; U.S. Pat. No. 5,545,807 to Surani et al.; International Publication Nos. WO 98/24884, published on Jun. 11, 1998; WO 94/25585, published Nov. 10, 1994; WO 93/1227, published Jun. 24, 1993; WO 92/22645, published Dec. 23, 1992; WO 92/03918, published Mar. 19, 1992.

Yet another aspect of the present disclosure relates to anti-C1q antibodies that are obtainable by a process comprising, immunizing an animal with an immunogenic C1q polypeptide, respectively, or an immunogenic portion thereof; and then isolating from the animal antibodies that specifically bind to the polypeptide.

In still another aspect of the present disclosure, partial or known antibody sequences can be used to generate and/or express new antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998, Nature 332:323 327; Jones, P. et al., 1986, Nature 321:522 525; and Queen, C. et al., 1989, Proc. Natl. Acad. See. U.S.A. 86:10029 10033). Such framework sequences can be obtained from public DNA databases that include germline or non-germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody at individual evenly across the variable region. For example, somatic mutations are relatively infrequent in the amino-terminal portion of framework region. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody (see PCT/US99/05535 filed on Mar. 12, 1999). Partial heavy and light chain sequence spanning the CDR regions is typically sufficient for this purpose. The partial sequence is used to determine which germline and/or non-germline variable and joining gene segments contributed to the recombined antibody variable genes. The germline and/or non-germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons. The process can also be used to screen libraries of particular immunoglobulin encoding sequences in one species (e.g., human) to design cognate immunoglobulin encoding sequences from known antibody sequence in another species (e.g., mouse) (see, for example, the Examples section below).

The nucleotide sequences of heavy and light chain transcripts from a hybridoma may be used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, J. Biol. Chem. 266L19867019870); and, HindIII sites are engineered upstream of the translation initiation sites.

For both the heavy and light chain variable regions, the optimized coding, and corresponding non-coding, strand sequences are broken down into 30-50 nucleotide approximately the midpoint of the corresponding non-coding oligonucleotide. Thus, for each chain, the oligonucleotides can be assembled into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of the heavy or light chain constant region in the PCR amplification to generate fragments that can easily be cloned into the expression vector constructs.

The reconstructed heavy and light chain variable regions are then combined with cloned promoter, leader sequence, translation initiation, leader sequence, constant region, 3' untranslated, polyadenylation, and transcription termination, sequences to form expression vector constructs. The heavy and light chain expression constructs can be combined into a single vector, co-transfected, serially transfected, or separately transfected into host cells which are then fused to form a host cell expressing both chains.

Plasmids for this use are known in the art and include the plasmids provided in the Examples section below. Fully human and chimeric antibodies of the present disclosure also include IgG1, IgG2, IgG3, IgG4, IgE, IgA, IgM, and IgD antibodies, and variants and mutants thereof. Similar plasmids can be constructed for expression of other heavy chain isotypes, or for expression of antibodies comprising lambda light chains.

Thus, in one aspect of the present disclosure, the structural features of known, non-human or human antibodies (e.g., a mouse anti-human anti-C1q antibody, such as the monoclonal antibody M1 produced by the hybridoma cell line having ATCC Accession Number PTA-120399) are used to create structurally related human anti-human C1q antibodies that retain at least one functional property of the antibodies of the present disclosure, such as binding to a C1q protein. Another functional property includes inhibiting binding of the monoclonal antibody M1 to C1q in a competition ELISA assay. In some embodiments, the structurally related anti-human C1q antibodies have a comparable binding affinity to the antigen as compared to the monoclonal antibody M1 as measured by the $IC_{50}$ value as described in the Examples section below. In some embodiments, the structurally related anti-human C1q antibodies have a higher affinity to the antigen as compared to the monoclonal antibody M1 as measured by the IC50 value as described in the Examples section below. In addition, one or more CDR or variable regions of an anti-C1q antibody (e.g., monoclonal antibody M1 produced by the hybridoma cell line having ATCC Accession Number PTA-120399) can be combined recombinantly with known human framework regions and CDRs to create additional, recombinantly-engineered, human anti-C1q antibodies of the present disclosure.

Since it is well-known in the art that antibody heavy and light chain CDR3 domains play a particularly important role in the binding specificity/affinity of an antibody for an antigen, the recombinant antibodies of the present disclosure prepared as set forth above may, in some embodiments, comprise the heavy and light chain CDR3s of variable regions of the monoclonal antibody M1 produced by the hybridoma cell line having ATCC Accession Number PTA-120399. In some embodiments, the antibodies further can comprise the CDR2s of variable regions of the monoclonal antibody M1. In some embodiments, the antibodies further can comprise the CDR1s of variable regions of the monoclonal antibody M1. In some embodiments, the antibodies can further comprise any combinations of the CDRs.

In some embodiments, the CDR1, 2, and/or 3 regions of the engineered antibodies described above may comprise the exact amino acid sequence(s) as those of variable regions of the monoclonal antibody M1 produced by the hybridoma cell line having ATCC Accession Number PTA-120399. However, the ordinarily skilled artisan will appreciate that some deviation from the exact CDR sequences may be possible while still retaining the ability of the antibody to bind C1q effectively (e.g., conservative sequence modifications). Accordingly, in another embodiment, the engineered antibody may be composed of one or more CDRs that are, for example, 50%, 60%, 70%, 80%, 85%, 90%, 91%, 92%, 93%, 94%, 95%, 96%, 97%, 98%, 99%, or 99.5% identical to one or more CDRs of the monoclonal antibody M1.

Antibody Fragments

In certain embodiments there are advantages to using anti-C1q antibody fragments, rather than whole anti-C1q antibodies. Smaller fragment sizes allow for rapid clearance.

Various techniques have been developed for the production of antibody fragments. Traditionally, these fragments were derived via proteolytic digestion of intact antibodies (see, e.g., Morimoto et al., *J. Biochem. Biophys. Method.* 24:107-117 (1992); and Brennan et al., *Science* 229:81 (1985)). However, these fragments can now be produced directly by recombinant host-cells, for example, using nucleic acids encoding anti-C1q antibodies of the present disclosure. Fab, Fv and scFv antibody fragments can all be expressed in and secreted from *E. coli*, thus allowing the straightforward production of large amounts of these fragments. A anti-C1q antibody fragments can also be isolated from the antibody phage libraries as discussed above. Alternatively, Fab'-SH fragments can be directly recovered from *E. coli* and chemically coupled to form $F(ab')_2$ fragments (Carter et al., *Bio/Technology* 10:163-167 (1992)). According to another approach, $F(ab')_2$ fragments can be isolated directly from recombinant host-cell culture. Production of Fab and $F(ab')_2$ antibody fragments with increased in vivo half-lives are described in U.S. Pat. No. 5,869,046. In other embodiments, the antibody of choice is a single chain Fv fragment (scFv). See WO 93/16185; U.S. Pat. Nos. 5,571, 894 and 5,587,458. The anti-C1q, anti-C1r, or anti-C1q antibody fragment may also be a "linear antibody," e.g., as described in U.S. Pat. No. 5,641,870. Such linear antibody fragments may be monospecific or bispecific.

Bispecific and Polyspecific Antibodies

In some embodiments, antibodies of the present disclosure encompass bispecific antibodies and polyspecific antibodies.

Bispecific antibodies (BsAbs) are antibodies that have binding specificities for at least two different epitopes, including those on the same or another protein (e.g., one or more C1q proteins of the present disclosure). Alternatively, one part of a BsAb can be armed to bind to the target C1q antigen, and another can be combined with an arm that binds to a second protein. Such antibodies can be derived from full length antibodies or antibody fragments (e.g., $F(ab')_2$ bispecific antibodies).

Methods for making bispecific antibodies are known in the art. Traditional production of full length bispecific antibodies is based on the coexpression of two immunoglobulin heavy-chain/light chain pairs, where the two chains have different specificities. Millstein et al., *Nature*, 305:537-539 (1983). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829 and in Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion may be with an immunoglobulin heavy chain constant domain, comprising at least part of the hinge, $C_H2$, and $C_H3$ regions. In some embodiments, the first heavy-chain constant region ($C_H1$) containing the site necessary for light chain binding is present in at least one of the fusions. DNAs encoding the immunoglobulin heavy chain fusions and, if desired, the immunoglobulin light chain, are inserted into separate expression vectors, and are co-transfected into a suitable host organism. This provides great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In some embodiments of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only half of the bispecific molecules provides an easy way of separation. This approach is disclosed in WO 94/04690. For further details of generating bispecific antibodies, see, for example, Suresh et al., *Methods in Enzymology* 121: 210 (1986).

According to another approach described in WO 96/27011 or U.S. Pat. No. 5,731,168, the interface between a pair of antibody molecules can be engineered to maximize the percentage of heterodimers which are recovered from recombinant-cell culture. The interface may comprise at least a part of the $C_H3$ region of an antibody constant domain. In this method, one or more small amino acid side chains from the interface of the first antibody molecule are replaced with larger side chains (e.g., tyrosine or tryptophan). Compensatory "cavities" of identical or similar size to the large side chains(s) are created on the interface of the second antibody molecule by replacing large amino acid side chains with smaller ones (e.g., alanine or threonine). This provides a mechanism for increasing the yield of the heterodimer over other unwanted end-products such as homodimers.

Techniques for generating bispecific antibodies from antibody fragments have been described in the literature. For example, bispecific antibodies can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175: 217-225 (1992) describes the production of fully humanized bispecific antibody F(ab')$_2$ molecules. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T-cells, as well as trigger the lytic activity of human cytotoxic lymphocytes against human breast tumor targets.

Various techniques for making and isolating bivalent antibody fragments directly from recombinant-cell culture have also been described. For example, bivalent heterodimers have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., *Proc. Nat'l Acad. Sci. USA*, 90: 6444-6448 (1993) has provided an alternative mechanism for making bispecific/bivalent antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific/bivalent antibody fragments by the use of single-chain Fv (sFv) dimers has also been reported. See Gruber et al., *J. Immunol.*, 152:5368 (1994).

Antibodies with more than two valencies are also contemplated. For example, trispecific antibodies can be prepared. Tutt et al., *J. Immunol.* 147:60 (1991).

Exemplary bispecific antibodies may bind to two different antigens. In some embodiments a bispecific antibody binds to a first antigen, C1q, and a second antigen facilitating transport across the blood-brain barrier. Numerous antigens are known in the art that facilitate transport across the blood-brain barrier (see, e.g., Gabathuler R., Approaches to transport therapeutic drugs across the blood-brain barrier to treat brain diseases, Neurobiol. Dis. 37 (2010) 48-57). Such second antigens include, without limitation, transferrin receptor (TR), insulin receptor (HIR), Insulin-like growth factor receptor (IGFR), low-density lipoprotein receptor related proteins 1 and 2 (LPR-1 and 2), diphtheria toxin receptor, including CRM197 (a non-toxic mutant of diphtheria toxin), llama single domain antibodies such as TMEM 30(A) (Flippase), protein transduction domains such as TAT, Syn-B, or penetratin, poly-arginine or generally positively charged peptides, and Angiopep peptides such as ANG1005 (see, e.g., Gabathuler, 2010).

Multivalent Antibodies

In some embodiments, antibodies of the present disclosure encompass multivalent antibodies. A multivalent antibody may be internalized (and/or catabolized) faster than a bivalent antibody by a cell expressing an antigen to which the antibodies bind. The anti-C1q antibodies of the present disclosure or antibody fragments thereof can be multivalent antibodies (which are other than of the IgM class) with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. In some embodiments, the dimerization domain comprises an Fc region or a hinge region. In this scenario, the antibody will comprise an Fc region and three or more antigen binding sites amino-terminal to the Fc region. In some embodiments, the multivalent antibody herein contains three to about eight, and in some embodiments four, antigen binding sites. The multivalent antibody contains at least one polypeptide chain (and in some embodiments two polypeptide chains), wherein the polypeptide chain or chains comprise two or more variable domains. For instance, the polypeptide chain or chains may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. Similarly, the polypeptide chain or chains may comprise $V_H$-$C_H$1-flexible linker-$V_H$-$C_H$1-Fc region chain; or $V_H$-$C_H$1-$V_H$-$C_H$1-Fc region chain. The multivalent antibody herein may further comprise at least two (and in some embodiments four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Heteroconjugate Antibodies

Heteroconjugate antibodies are also within the scope of the present disclosure. Heteroconjugate antibodies are composed of two covalently joined antibodies (e.g., anti-C1q antibodies of the present disclosure or antibody fragments thereof). For example, one of the antibodies in the heteroconjugate can be coupled to avidin, the other to biotin. Such antibodies have, for example, been proposed to target immune system cells to unwanted cells, U.S. Pat. No. 4,676,980, and have been used to treat HIV infection. International Publication Nos. WO 91/00360, WO 92/200373 and EP 0308936. It is contemplated that the antibodies may be prepared in vitro using known methods in synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980. Heteroconjugate antibodies may be made using any convenient cross-linking methods. Suitable cross-linking agents are well known in the art, and are disclosed in U.S. Pat. No. 4,676,980, along with a number of cross-linking techniques.

Effector Function Engineering

In some embodiments, it may be desirable to modify a humanized anti-C1q antibody of the present disclosure to modify effector function and/or to increase serum half-life of the antibody. For example, the Fc receptor binding site on the constant region may be modified or mutated to remove or reduce binding affinity to certain Fc receptors, such as FcγRI, FcγRII, and/or FcγRIII. In some embodiments, the effector function is impaired by removing N-glycosylation of the Fc region (e.g., in the CH 2 domain of IgG) of the antibody. In some embodiments, the effector function is impaired by modifying regions such as 233-236, 297, and/or 327-331 of human IgG as described in PCT WO 99/58572 and Armour et al., *Molecular Immunology* 40: 585-593 (2003); Reddy et al., *J. Immunology* 164:1925-1933 (2000).

The constant region of the anti-complement antibodies described herein may also be modified to impair complement activation. For example, complement activation of IgG antibodies following binding of the C1 component of complement may be reduced by mutating amino acid residues in the constant region in a C1 binding motif (e.g., C1q binding motif). It has been reported that Ala mutation for each of D270, K322, P329, P331 of human IgG1 significantly reduced the ability of the antibody to bind to C1q and activating complement. For murine IgG2b, C1q binding motif constitutes residues E318, K320, and K322. Idusogie et al. (2000) *J. Immunology* 164:4178-4184; Duncan et al. (1988) *Nature* 322: 738-740. As the C1s binding motif E318, K320, and K322 identified for murine IgG2b is believed to be common for other antibody isotypes (Duncan et al. (1988) *Nature* 322:738-740), C1q binding activity for IgG2b can be abolished by replacing any one of the three specified residues with a residue having an inappropriate functionality on its side chain. It is not necessary to replace the ionic residues only with Ala to abolish C1q binding. It is also possible to use other alkyl-substituted non-ionic residues, such as Gly, Ile, Leu, or Val, or such aromatic non-polar residues as Phe, Tyr, Trp, and Pro in place of any one of the three residues in order to abolish C1q binding. In addition, it is also possible to use such polar non-ionic residues as Ser, Thr, Cys, and Met in place of residues 320 and 322, but not 318, in order to abolish C1s binding activity. In addition, removal of carbohydrate modifications of the Fc region necessary for complement binding can prevent complement activation Glycosylation of a conserved asparagine (Asn-297) on the CH2 domain of IgG heavy chains is essential for antibody effector functions (Jefferis et al. (1998) *Immunol Rev* 163:59-76). Modification of the Fc glycan alters IgG conformation and reduces the Fc affinity for binding of complement protein C1q and effector cell receptor FcR (Alhorn et al. (2008) *PLos ONE* 2008; 3:e1413). Complete removal of the Fc glycan abolishes CDC and ADCC. Deglycosylation can be performed using glycosidase enzymes for example Endoglycosidase S (EndoS), a 108 kDa enzyme encoded by the gene endoS of *Streptococcus pyogenes* that selectively digests asparagine-linked glycans on the heavy chain of all IgG subclasses, without action on other immunoglobulin classes or other glycoproteins (Collin et al. (2001) *EMBO J* 2001; 20:3046-3055).

To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG$_1$, IgG$_2$, IgG$_3$, or IgG$_4$) that is responsible for increasing the in vivo serum half-life of the IgG molecule.

Other Amino Acid Sequence Modifications

Amino acid sequence modifications of humanized anti-C1q antibodies of the present disclosure, or antibody fragments thereof, are also contemplated. For example, it may be desirable to improve the binding affinity and/or other biological properties of the antibodies or antibody fragments. Amino acid sequence variants of the antibodies or antibody fragments are prepared by introducing appropriate nucleotide changes into the nucleic acid encoding the antibodies or antibody fragments, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics (i.e., the ability to bind or physically interact with a C1q protein of the present disclosure). The amino acid changes also may alter post-translational processes of the antibody, such as changing the number or position of glycosylation sites.

A useful method for identification of certain residues or regions of the anti-C1q antibody that are preferred locations for mutagenesis is called "alanine scanning mutagenesis" as described by Cunningham and Wells in *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the target antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed antibody variants are screened for the desired activity.

Amino acid sequence insertions include amino- ("N") and/or carboxy- ("C") terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in the Table A below under the heading of "preferred substitutions". If such substitutions result in a change in biological activity, then more substantial changes, denominated "exemplary substitutions" in Table A, or as further described below in reference to amino acid classes, may be introduced and the products screened.

TABLE A

Amino Acid Substitutions

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment, such as an Fv fragment).

In some embodiments, the substitutional variant involves substituting one or more hypervariable region residues of a parent antibody (e.g. a humanized or human anti-C1q antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and the antigen (e.g., a C1q protein of the present disclosure). Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-IgE antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibodies (e.g., anti-C1q antibody of the present disclosure) or antibody fragments.

Other Antibody Modifications

In some embodiments, humanized anti-C1q antibodies of the present disclosure, or antibody fragments thereof, may be further modified to contain additional non-proteinaceous moieties that are known in the art and readily available. In some embodiments, the moieties suitable for derivatization of the antibody are water-soluble polymers. Non-limiting examples of water-soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc. Such techniques and other suitable formulations are disclosed in *Remington: The Science and Practice of Pharmacy,* 20th Ed., Alfonso Gennaro, Ed., Philadelphia College of Pharmacy and Science (2000).

Nucleic Acids, Vectors, and Host Cells

Humanized anti-C1q antibodies of the present disclosure may be produced using recombinant methods and compositions, e.g., as described in U.S. Pat. No. 4,816,567. In some embodiments, isolated nucleic acids having a nucleotide sequence encoding any of the anti-C1q antibodies of the present disclosure are provided. Such nucleic acids may encode an amino acid sequence containing the VL and/or an amino acid sequence containing the VH of the anti-C1q antibody (e.g., the light and/or heavy chains of the antibody). In some embodiments, one or more vectors (e.g., expression vectors) containing such nucleic acids are provided. In some embodiments, a host cell containing such nucleic acid is also provided. In some embodiments, the host cell contains (e.g., has been transduced with): (1) a vector containing a nucleic acid that encodes an amino acid sequence containing the VL of the antibody and an amino acid sequence containing the VH of the antibody, or (2) a first vector containing a nucleic acid that encodes an amino acid sequence containing the VL of the antibody and a second vector containing a nucleic acid that encodes an amino acid sequence containing the VH of the antibody. In some embodiments, the host cell is eukaryotic, e.g., a Chinese Hamster Ovary (CHO) cell or lymphoid cell (e.g., Y0, NS0, Sp20 cell).

Methods of making an anti-C1q antibody of the present disclosure are provided. In some embodiments, the method includes culturing a host cell of the present disclosure containing a nucleic acid encoding the anti-C1q antibody, under conditions suitable for expression of the antibody. In some embodiments, the antibody is subsequently recovered from the host cell (or host cell culture medium).

For recombinant production of a humanized anti-C1q antibody of the present disclosure, a nucleic acid encoding the anti-C1q antibody is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable vectors containing a nucleic acid sequence encoding any of the anti-C1q antibodies of the present disclosure, or fragments thereof polypeptides (including antibodies) described herein include, without limitation, cloning vectors and expression vectors. Suitable cloning vectors can be constructed according to standard techniques, or may be selected from a large number of cloning vectors available in the art. While the cloning vector selected may vary according to the host cell intended to be used, useful cloning vectors generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a nucleic acid of the present disclosure. The expression vector may replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the nucleic acids of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell. In some embodiments, the vector contains a nucleic acid containing one or more amino acid sequences encoding an anti-C1q antibody of the present disclosure.

Suitable host cells for cloning or expression of antibody-encoding vectors include prokaryotic or eukaryotic cells. For example, anti-C1q antibodies of the present disclosure may be produced in bacteria, in particular when glycosylation and Fc effector function are not needed. For expression of antibody fragments and polypeptides in bacteria (e.g., U.S. Pat. Nos. 5,648,237, 5,789,199, and 5,840,523; and Charlton, *Methods in Molecular Biology,* Vol. 248 (B. K.

C. Lo, ed., Humana Press, Totowa, N.J., 2003), pp. 245-254, describing expression of antibody fragments in *E. coli.*). After expression, the antibody may be isolated from the bacterial cell paste in a soluble fraction and can be further purified.

In addition to prokaryotes, eukaryotic microorganisms, such as filamentous fungi or yeast, are also suitable cloning or expression hosts for antibody-encoding vectors, including fungi and yeast strains whose glycosylation pathways have been "humanized," resulting in the production of an antibody with a partially or fully human glycosylation pattern (e.g., Gerngross, *Nat. Biotech.* 22:1409-1414 (2004); and Li et al., *Nat. Biotech.* 24:210-215 (2006)).

Suitable host cells for the expression of glycosylated antibody can also be derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts (e.g., U.S. Pat. Nos. 5,959,177, 6,040,498, 6,420,548, 7,125,978, and 6,417,429, describing PLANTIBODIES™ technology for producing antibodies in transgenic plants.).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR-CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

Pharmaceutical Compositions

Humanized anti-C1q antibodies of the present disclosure can be incorporated into a variety of formulations for therapeutic use (e.g., by administration) or in the manufacture of a medicament (e.g., for treating or preventing a neurodegenerative disease or autoimmune disease) by combining the antibodies with appropriate pharmaceutically acceptable carriers or diluents, and may be formulated into preparations in solid, semi-solid, liquid or gaseous forms. Examples of such formulations include, without limitation, tablets, capsules, powders, granules, ointments, solutions, suppositories, injections, inhalants, gels, microspheres, and aerosols. Pharmaceutical compositions can include, depending on the formulation desired, pharmaceutically-acceptable, non-toxic carriers of diluents, which are vehicles commonly used to formulate pharmaceutical compositions for animal or human administration. The diluent is selected so as not to affect the biological activity of the combination. Examples of such diluents include, without limitation, distilled water, buffered water, physiological saline, PBS, Ringer's solution, dextrose solution, and Hank's solution. A pharmaceutical composition or formulation of the present disclosure can further include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

A pharmaceutical composition of the present disclosure can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, and enhance solubility or uptake). Examples of such modifications or complexing agents include, without limitation, sulfate, gluconate, citrate and phosphate. The polypeptides of a composition can also be complexed with molecules that enhance their in vivo attributes. Such molecules include, without limitation, carbohydrates, polyamines, amino acids, other peptides, ions (e.g., sodium, potassium, calcium, magnesium, manganese), and lipids.

Further examples of formulations that are suitable for various types of administration can be found in *Remington's Pharmaceutical Sciences*, Mace Publishing Company, Philadelphia, Pa., 17th ed. (1985). For a brief review of methods for drug delivery, see, Langer, *Science* 249:1527-1533 (1990).

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Formulations may be optimized for retention and stabilization in the brain or central nervous system. When the agent is administered into the cranial compartment, it is desirable for the agent to be retained in the compartment, and not to diffuse or otherwise cross the blood brain barrier. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the antibody, such as a humanized anti-C1q antibody of the present disclosure, in a biodegradable or bioerodible implant. The rate of release of the therapeutically active agent is controlled by the rate of transport through the polymeric matrix, and the biodegradation of the implant. The transport of drug through the polymer barrier will also be affected by compound solubility, polymer hydrophilicity, extent of polymer cross-linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

The implants may be monolithic, i.e. having the active agent homogenously distributed through the polymeric matrix, or encapsulated, where a reservoir of active agent is encapsulated by the polymeric matrix. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, ease of encapsulation, a half-life in the physiological environment.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the present disclosure. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137-149.

Pharmaceutical Dosages

Pharmaceutical compositions of the present disclosure containing a humanized anti-C1q antibody of the present disclosure may be used (e.g., administered to an individual in need of treatment with an anti-C1q antibody, such as a human individual) in accordance with known methods, such as intravenous administration as a bolus or by continuous infusion over a period of time, by intramuscular, intraperitoneal, intracerobrospinal, intracranial, intraspinal, subcutaneous, intra-articular, intrasynovial, intrathecal, oral, topical, or inhalation routes.

Dosages and desired drug concentration of pharmaceutical compositions of the present disclosure may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles described in Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46.

For in vivo administration of any of the humanized anti-C1q antibodies of the present disclosure, normal dosage amounts may vary from about 10 ng/kg up to about 100 mg/kg of an individual's body weight or more per day, depending upon the route of administration. In some embodiments, the dose amount is about 1 mg/kg/day to 10 mg/kg/day. For repeated administrations over several days or longer, depending on the severity of the disease, disorder, or condition to be treated, the treatment is sustained until a desired suppression of symptoms is achieved.

An exemplary dosing regimen may include administering an initial dose of a humanized anti-C1q antibody, of about 2 mg/kg, followed by a weekly maintenance dose of about 1 mg/kg every other week. Other dosage regimens may be useful, depending on the pattern of pharmacokinetic decay that the physician wishes to achieve. For example, dosing an individual from one to twenty-one times a week is contemplated herein. In certain embodiments, dosing ranging from about 3 µg/kg to about 2 mg/kg (such as about 3 µg/kg, about 10 µg/kg, about 30 µg/kg, about 100 µg/kg, about 300 µg/kg, about 1 mg/kg, or about 2 mg/kg) may be used. In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. Progress of the therapy is easily monitored by conventional techniques and assays. The dosing regimen, including the humanized anti-C1q antibody administered, can vary over time independently of the dose used.

Dosages for a particular humanized anti-C1q antibody may be determined empirically in individuals who have been given one or more administrations of the humanized anti-C1q antibody. Individuals are given incremental doses of a humanized anti-C1q antibody. To assess efficacy of a humanized anti-C1q antibody, any clinical symptom of a neurodegenerative disorder, inflammatory disorder, or autoimmune disorder can be monitored.

Administration of a humanized anti-C1q antibody of the present disclosure can be continuous or intermittent, depending, for example, on the recipient's physiological condition, whether the purpose of the administration is therapeutic or prophylactic, and other factors known to skilled practitioners. The administration of a humanized anti-C1q antibody may be essentially continuous over a preselected period of time or may be in a series of spaced doses.

Guidance regarding particular dosages and methods of delivery is provided in the literature; see, for example, U.S. Pat. Nos. 4,657,760; 5,206,344; or U.S. Pat. No. 5,225,212. It is within the scope of the present disclosure that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

Therapeutic Uses

The present disclosure provides humanized anti-C1q antibodies, and antigen-binding fragments thereof, which can bind to and neutralize a biologic activity of C1q. These humanized anti-C1q antibodies are useful for preventing, reducing risk, or treating a range of diseases associated with complement activation, including, without limitation, neurodegenerative disorders, inflammatory disorders, and autoimmune disorders. Accordingly, as disclosed herein, humanized anti-C1q antibodies of the present disclosure may be used for treating, preventing, or reducing risk of a disease associated with complement activation, including, without limitation, neurodegenerative disorders, inflammatory disorders, and autoimmune disorders, in an individual. In some embodiments, the individual has a disease. In some embodiments, the individual is a human.

Neurodegenerative disorders that may be treated with humanized anti-C1q antibodies of this disclosure include disorders associated with loss of nerve connections or synapses, including CF 1-dependent synapse loss. Such disorders may include, without limitation, Alzheimer's disease, amyotrophic lateral sclerosis, multiple sclerosis, glaucoma, myotonic dystrophy, Guillain-Barre' syndrome (GBS), Myasthenia Gravis, Bullous Pemphigoid, spinal muscular atrophy, Down syndrome, Parkinson's disease, and Huntington's disease. In some neurodegenerative disorders, synapse loss is dependent on the complement receptor 3 (CR3)/C3 or complement receptor CR1. In some neurodegenerative disorders, synapse loss is associated with pathological activity-dependent synaptic pruning. In some disorders, synapses are phagocytosed by microglia. Accordingly, the humanized anti-C1q antibodies of the present disclosure may be used to treat, prevent, or improve one or more symptoms of a neurodegenerative disorder of the present disclosure. In some embodiments, the present disclosure provides methods of treating, preventing, or improving one or more symptoms in individuals having a neurodegenerative disorder of the present disclosure by administering a humanized anti-C1q antibody of the present disclosure to, for example, inhibit the interaction between C1q and an autoantibody, the interaction of C1q and C1r, and/or the interaction of C1q and C1s.

Inflammatory or autoimmune diseases that may be treated with humanized anti-C1q antibodies of this disclosure include, without limitation, rheumatoid arthritis (RA), acute respiratory distress syndrome (ARDS), remote tissue injury after ischemia and reperfusion, complement activation during cardiopulmonary bypass surgery, dermatomyositis, pemphigus, lupus nephritis and resultant glomerulonephritis and vasculitis, cardiopulmonary bypass, cardioplegia-induced coronary endothelial dysfunction, type II membranoproliferative glomerulonephritis, IgA nephropathy, acute renal failure, cryoglobulemia, antiphospholipid syndrome, Chronic open-angle glaucoma, acute closed angle glaucoma, macular degenerative diseases, age-related macular degeneration (AMD), (AMD-wet), Geographic atrophy choroidal neovascularization (CNV), uveitis, diabetic retinopathy, ischemia-related retinopathy, endophthalmitis, intraocular neovascular disease, diabetic macular edema, pathological myopia, von Hippel-Lindau disease, histoplasmosis of the eye, Neuromyelitis Optica (NMO), Central Retinal Vein Occlusion (CRVO), corneal neovascularization, retinal neovascularization, Leber's hereditary optic neuropathy, optic neuritis, Behcet's retinopathy, ischemic optic neuropathy, retinal vasculitis, ANCA vasculitis, Purtscher retinopathy, Sjogren's dry eye disease, dry AMD, sarcoidosis, temporal arteritis, polyarteritis nodosa, multiple sclerosis, as well as allo-transplantation, hyperacute rejection, hemodialysis, chronic occlusive pulmonary distress syndrome (COPD), asthma, and aspiration pneumonia. In some embodiments, autoimmune disease may further include, without limitation, Guillain-Barré syndrome, myasthenia gravis, Diabetes mellitus type 1, Hashimoto's thyroiditis, Addison's disease, Coeliac disease, Crohn's disease, pernicious anaemia, Pemphigus vulgaris, vitiligo, autoimmune hemolytic anemias, paraneoplastic syndromes, a vasculitis disease, hypocomplementemic urticarial vasculitis (HUV), polymyalgia rheumatica, temporal arteritis, and Wegener's granulomatosis.

In autoimmune diseases, such as Neuromyelitis Optica (NMO), autoantibodies activate the complement system. In NMO patients, the classical complement pathway is triggered by the binding of an autoantibody, such as an AQP4-targeted autoantibody, to its autoantigen, AQP4. AQP4 thereby activates the classical pathway of complement activation. In the first step of this activation process complement factor C1q binds to the autoantibody-autoantigen-immune complex. Autoantibodies may include naturally occurring antibodies, such as serum antibodies from NMO patients (commonly referred to as NMO-IgG) or monoclonal antibodies, such as rAb-53.

Accordingly, the humanized anti-C1q antibodies of the present disclosure may be used to treat, prevent, or improve one or more symptoms of an inflammatory or autoimmune disease of the present disclosure. In some embodiments, the present disclosure provides methods of treating, preventing, or improving one or more symptoms in individuals having an inflammatory or autoimmune disease of the present disclosure by administering a humanized anti-C1q antibody of the present disclosure to, for example, inhibit the interaction between C1q and an autoantibody, the interaction of C1 q and C1r, and/or the interaction of C1 q and C1 s.

Metabolic diseases that may be treated with humanized anti-C1q antibodies include, without limitation, diabetes, such as type II diabetes, and obesity. In vitro and in vivo models of metabolic disorders that can be used for the testing of humanized anti-C1q antibodies are well known in the art. Accordingly, the humanized anti-C1q antibodies of the present disclosure may be used to treat, prevent, or improve one or more symptoms of a metabolic disease of the present disclosure. In some embodiments, the present disclosure provides methods of treating, preventing, or improving one or more symptoms in individuals having metabolic disease of the present disclosure by administering a humanized anti-C1q antibody of the present disclosure to, for example, inhibit the interaction between C1q and an autoantibody, such as an anti-ganglioside autoantibody, the interaction of C1 q and C1r, and/or the interaction of C1 q and C1 s.

Combination Treatments

The antibodies of the present disclosure may be used, without limitation, in combination with any additional treatment for neurodegenerative disorders, inflammatory disorders, and/or autoimmune disorders.

In some embodiments, a humanized anti-C1q antibody of this disclosure is administered in therapeutically effective amounts in combination with a second anti-complement factor antibody (e.g., a neutralizing anti-complement factor antibody), such as an anti-C1s or anti-C1r antibody, or a second anti-C1q antibody. In some embodiments, a humanized anti-C1q antibody of this disclosure is administered in therapeutically effective amounts with a second and a third neutralizing anti-complement factor antibody, such as a second anti-C1q antibody, an anti-C1s antibody, and/or an anti-C1r antibody.

In some embodiments, the humanized anti-C1q antibodies of this disclosure are administered in combination with an inhibitor of antibody-dependent cellular cytotoxicity (ADCC). ADCC inhibitors may include, without limitation, soluble NK cell inhibitory receptors such as the killer cell Ig-like receptors (KIRs), which recognize HLA-A, HLA-B, or HLA-C and C-type lectin CD94/NKG2A heterodimers, which recognize HLA-E (see, e.g., López-Botet M., T. Bellón, M. Llano, F. Navarro, P. Garcia & M. de Miguel. (2000), Paired inhibitory and triggering NK cell receptors for HLA class I molecules. Hum. Immunol. 61: 7-17; Lanier L. L. (1998) Follow the leader: NK cell receptors for classical and nonclassical MHC class I. *Cell* 92: 705-707.), and cadmium (see, e.g., *Immunopharmacology* 1990; Volume 20, Pages 73-8).

In some embodiments, the humanized anti-C1q antibodies of this disclosure are administered in combination with an inhibitor of the alternative pathway of complement activation. Such inhibitors may include, without limitation, factor B blocking antibodies, factor D blocking antibodies, soluble, membrane-bound, tagged or fusion-protein forms of CD59, DAF, CR1, CR2, Crry or Comstatin-like peptides that block the cleavage of C3, non-peptide C3aR antagonists such as SB 290157, Cobra venom factor or non-specific complement inhibitors such as nafamostat mesilate (FUTHAN; FUT-175), aprotinin, K-76 monocarboxylic acid (MX-1) and heparin (see, e.g., T. E. Mollnes & M. Kirschfink, *Molecular Immunology* 43 (2006) 107-121). In some embodiments, the humanized anti-C1q antibodies of this disclosure are administered in combination with an inhibitor of the interaction between the autoantibody and its autoantigen. Such inhibitors may include purified soluble forms of the autoantigen, or antigen mimetics such as peptide or RNA-derived mimotopes, including mimotopes of the AQP4 antigen. Alternatively, such inhibitors may include blocking agents that recognize the autoantigen and prevent binding of the autoantibody without triggering the classical complement pathway. Such blocking agents may include, e.g., autoantigen-binding RNA aptamers or antibodies lacking functional C1q binding sites in their Fc domains (e.g., Fab fragments or antibody otherwise engineered not to bind C1q).

Diagnostic Uses

The humanized anti-C1q antibodies of the present disclosure, or functional fragments thereof, also have diagnostic utility. This disclosure therefore provides methods of using the antibodies of this disclosure, or functional fragments thereof, for diagnostic purposes, such as the detection of C1q in an individual or in tissue samples derived from an individual. In some embodiments, the individual is a human. In some embodiments, the individual is a human patient suffering from a neurodegenerative disorder or an inflammatory, or autoimmune disease. In some embodiments, the humanized anti-C1q antibodies of this disclosure are used to detect synapses and synapse loss. For example, synapse loss may be measured in an individual suffering from a neurodegenerative disorder such as Alzheimer's disease or glaucoma.

In some embodiments, the diagnostic methods involve the steps of administering a humanized anti-C1q antibody of this disclosure, or functional fragment thereof, to an individual and detecting the antibody bound to a synapse of the individual. Antibody-binding to synapses may be quantified, for example, by non-invasive techniques such as positron emission tomography (PET), X-ray computed tomography, single-photon emission computed tomography (SPECT), computed tomography (CT), and computed axial tomography (CAT).

In some embodiments, the diagnostic methods involve detecting synapses in a biological sample, such as a biopsy specimen, a tissue, or a cell. A humanized anti-C1q antibody, or functional fragment thereof, is contacted with the biological sample and synapse-bound antibody is detected. The detection method may involve quantification of the synapse-bound antibody. Antibody detection in biological samples may occur with any method known in the art, including immunofluorescence microscopy, immunocytochemistry, immunohistochemistry, ELISA, FACS analysis, immunoprecipitation, or micro-positron emission tomography. In certain embodiments, the antibody is radiolabeled, for example with $^{18}$F and subsequently detected utilizing micro-positron emission tomography analysis.

The quantification of synapse-bound antibodies provides a relative measure for the number of synapses present in the individual. Typically, synapses are quantified repeatedly over a period of time. The exact periodicity of synapse quantification depends on many factors, including the nature of the neurodegenerative disease, the stage of disease progression, treatment modalities and many other factors. Repeat measurements commonly reveal progressive synapse loss in individuals having a neurodegenerative disorder. Alternatively, relative synapse counts may be compared in populations of diseased individuals and healthy control individuals at a single time point. In diseased individuals undergoing treatment, the treatment's efficacy can be assessed by comparing the rates of synapse loss in the treated individuals with the rates of synapse loss in a control group. Control group members have received either no treatment or a control treatment, such as a placebo control.

Kits

The present disclosure also provides kits containing a humanized anti-C1q antibody of the present disclosure, or a functional fragment thereof. Kits of the present disclosure include one or more containers comprising a purified humanized anti-C1q antibody of this disclosure. In some embodiments, the kits further include instructions for use in accordance with the methods of this disclosure. In some embodiments, these instructions comprise a description of administration of the humanized anti-C1q antibody to treat or diagnose a disease associated with complement activation including, without limitation a neurodegenerative disorder (e.g., Alzheimer's disease), inflammatory disease, autoimmune disease, and/or metabolic disorder, according to any methods of this disclosure. In some embodiments, the instructions comprise a description of how to detect C1q, for example in an individual, in a tissue sample, or in a cell. The kit may further comprise a description of selecting an individual suitable for treatment based on identifying whether that individual has the disease and the stage of the disease.

The instructions generally include information as to dosage, dosing schedule, and route of administration for the intended treatment. The containers may be unit doses, bulk packages (e.g., multi-dose packages) or sub-unit doses. Instructions supplied in the kits of the present disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, e.g., a neurodegenerative disease. Instructions may be provided for practicing any of the methods described herein.

The kits of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (e.g., the container may be an intravenous solution bag or a vial having a stopper pierceable by a hypodermic injection needle). At least one active agent in the composition is an inhibitor of classical complement pathway. The container may further comprise a second pharmaceutically active agent.

Kits may optionally provide additional components such as buffers and interpretive information. Normally, the kit comprises a container and a label or package insert(s) on or associated with the container.

The present disclosure will be more fully understood by reference to the following Examples. They should not, however, be construed as limiting any aspect or scope of the present disclosure in any way. All citations throughout the disclosure are hereby expressly incorporated by reference.

EXAMPLES

Example 1: Production of Humanized Anti-C1q Antibodies

Introduction

This example describes the generation of fully humanized antibodies from the murine hybridoma M1 (expressing the mouse anti-human C1q antibody M1). Composite human antibody variable region genes were generated using synthetic oligonucleotides encoding combinations of selected human sequence segments. These were then cloned into vectors encoding human IgG4 (S241P L248E) heavy chain and human kappa light chain. Humanized antibodies were stably expressed in NS0 (mouse myeloma cell-line) cells, Protein A purified and tested for binding to human C1q using a competition ELISA assay against biotinylated murine M1 antibody. Selected antibodies were also tested for binding to mouse C1q using competition ELISA assay against biotinylated chimeric antibody.

Results

Sequencing of Anti-Human C1q V Regions

RNA was extracted from the hybridoma cell pellet expressing M1 antibody using an RNAqueousR-4PCR kit (Ambion cat. no. AM1914). Initially, RT-PCR was performed using degenerate primer pools for murine signal sequences together with constant region primers for both of IgG and Igκ. Heavy chain V region RNA was amplified using a set of six degenerate primer pools (HA to HF) and light chain V region mRNA was amplified using a set of seven degenerate primer pools for the κ cluster (KA to KG).

For the VH region, amplification products of the expected size were found in IgG primer pools HB and HE. For the Vκ region, amplification products of the expected size were found in kappa primer pools KC, KE, and KG. The PCR products obtained from each of the successful amplifications were purified and cloned into a 'TA' cloning vector (pGEM-T Easy, Promega cat. no. A1360) and sequenced. A total of 14 VH and 24 Vκ clones were sequenced.

A single functional VH gene was identified in 14 clones from IgG pools HB and HE. A single functional Vκ gene sequence was identified from 9 clones from primer pool KC. The 3' coding sequence downstream of the variable region obtained from IgG primer pools was consistent with the antibody isotype being IgG.

The functional VH and Vκ gene sequences were identical to the hybridoma sequences with the exception of five amino acids at the beginning of the VH sequence and two amino acids at the beginning of the Vκ sequence. These differences were most likely due to the method of sequencing, and were a result of using primers that are degenerate to the signal sequence rather than primers that are degenerate to 5' end of V regions.

The amino acid sequence of the functional VH is:

(SEQ ID NO: 21)
QVQLQQPGAELVKPGASVKLSCKSSGYHFTSYWMHWVQRPGQGLEWIGV

IHPNSGSINYNEKFESKATLTVDKSSSTAYMQLSSLTSEDSAVYYCAGER

DSTEVLPMDYWGQGTSVTVSS.

The hyper variable regions (HVRs) of the VH are depicted in bolded and underlined text.

The amino acid sequence of the functional Vκ is:

(SEQ ID NO: 22)
DVQITQSPSYLAASPGETITINCRASKSINKYLAWYQEKPGKTNKLLIYS

GSTLQSGIPSRFSGSGSGTDFTLTISSLEPEDFAMYYCQQHNEYPLTFGA

GTKLELK.

The hyper variable regions (HVRs) of the Vκ are depicted in bolded and underlined text.

Construction of Chimeric Antibody

Figure 1A:
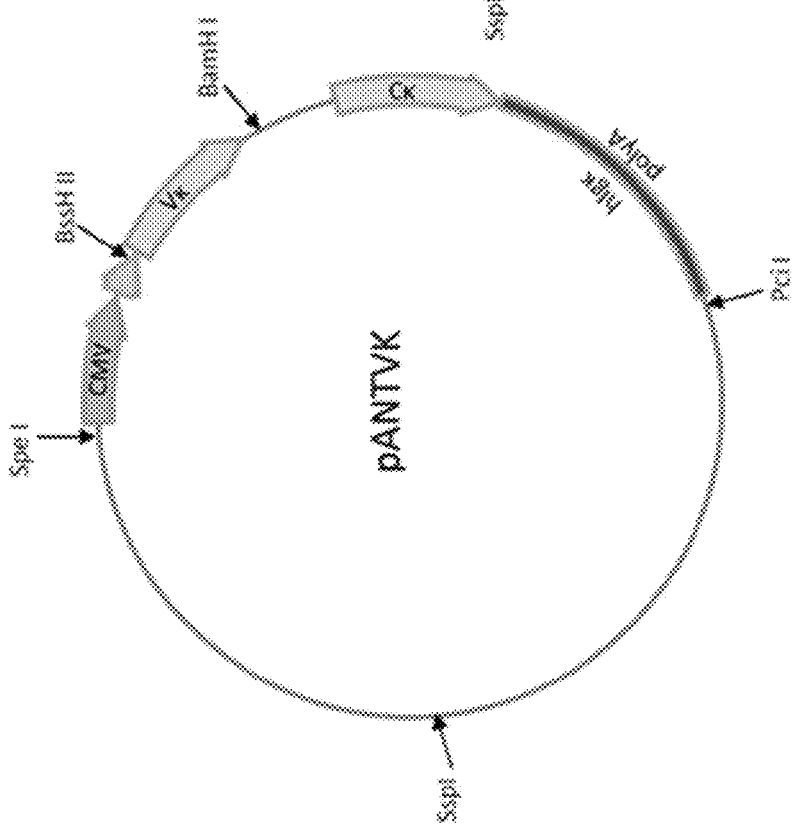

The VH and Vκ sequences of the murine M1 antibody were PCR amplified using primers that introduced flanking restriction enzyme sites for cloning into the IgG4 (S241P L248E) heavy and kappa chain expression vectors (FIG. 1A and FIG. 1B). The BamHI, HindIII and SspI restriction sites were removed from the Vκ sequence in order to clone the gene. The VH region was cloned using MluI and HindIII sites, and the Vκ region was cloned using BssHII and BamHI restriction sites. Both constructs were confirmed by sequencing.

Design of Composite Human Variable Region Sequences

Structural models of the murine M1 antibody V regions were produced using Swiss PDB and analyzed in order to identify important "constraining" amino acids in the V regions that were likely to be essential for the binding properties of the antibody. Most residues contained within the HVRs (using both Kabat and Chothia definitions) together with a number of framework residues were considered to be important. The VH and Vκ sequences of M1 contain typical framework residues and the HVR 1, 2 and 3 motifs are comparable to many murine antibodies.

From the above analysis, it was considered that composite human sequences of M1 could be created with a wide latitude for alternative residues outside of the HVRs but with only a narrow menu of possible residues within the HVR sequences. Preliminary analysis indicated that corresponding sequence segments from several human antibodies could be combined to create HVRs similar or identical to those in the murine sequences. For regions outside of and flanking the HVRs, a wide selection of human sequence segments were identified as possible components of the novel humanized V regions.

CD4+ T Cell Epitope Avoidance

Based upon the structural analysis, a large preliminary set of sequence segments that could be used to create M1 humanized variants were selected and analyzed using iTope™ technology for in silico analysis of peptide binding to human MHC class II alleles (Perry, L C A et al. *Drugs RD.* 2008; 9(6):385-96), and using the TCED™ T-cell epitope database of known antibody sequence-related T cell epitopes (Bryson, C J et al. *BioDrugs.* 2010 Feb. 1; 24(1):1-8). Sequence segments that were identified as significant non-human germline binders to human MHC class II or that scored significant hits against the TCED™ were discarded. This resulted in a reduced set of segments, and combinations of these were again analyzed, as above, to ensure that the junctions between segments did not contain potential T cell epitopes. Selected sequence segments were assembled into complete V region sequences that were devoid of significant T cell epitopes. Four heavy chain sequences (VH1-VH4) and four light chain sequences (Vκ1-Vκ4) were then chosen for gene synthesis, expression in mammalian cells, and testing for activity.

Sequences of Humanized Heavy Chain and Light Variable Domains

Using standard techniques, the amino acid and nucleic acid sequences encoding the heavy chain variable domain (VH) and kappa light chain variable domain (Vκ) variants were determined.

The amino acid sequence of heavy chain variable domain variant 1 (VH1) is:

(SEQ ID NO: 1)
QVQLVQSGAELKKPGASVKVSCKSS<u>GYHFTSYWMH</u>WVKQAPGQGLEWIG<u>V</u>
<u>IHPNSGSINYNEKFES</u>KATITVDKSTSTAYMQLSSLTSEDSAVYYCAG<u>ER</u>
<u>DSTEVLPMDY</u>WGQGTSVTVSS.

The hyper variable regions (HVRs) of VH1 are depicted in bolded and underlined text.

The amino acid sequence of heavy chain variable domain variant 2 (VH2) is:

(SEQ ID NO: 2)
QVQLVQSGAELKKPGASVKVSCKSS<u>GYHFTSYWMH</u>WVKQAPGQGLEWIG<u>V</u>
<u>IHPNSGSINYNEKFES</u>RATITVDKSTSTAYMELSSLRSEDTAVYYCAG<u>ER</u>
<u>DSTEVLPMDY</u>WGQGTTVTVSS.

The hyper variable regions (HVRs) of VH2 are depicted in bolded and underlined text.

The amino acid sequence of heavy chain variable domain variant 3 (VH3) is:

(SEQ ID NO: 3)
QVQLVQSGAELKKPGASVKVSCKSS<u>GYHFTSYWMH</u>WVKQAPGQGLEWIG<u>V</u>
<u>IHPNSGSINYNEKFES</u>RVTITVDKSTSTAYMELSSLRSEDTAVYYCAG<u>ER</u>
<u>DSTEVLPMDY</u>WGQGTTVTVSS.

The hyper variable regions (HVRs) of VH3 are depicted in bolded and underlined text.

The amino acid sequence of heavy chain variable domain variant 4 (VH4) is:

(SEQ ID NO: 4)
QVQLVQSGAELKKPGASVKVSCKSS<u>GYHFTSYWMH</u>WVRQAPGQGLEWIG<u>V</u>
<u>IHPNSGSINYNEKFES</u>RVTITVDKSTSTAYMELSSLRSEDTAVYYCAG<u>ER</u>
<u>DSTEVLPMDY</u>WGQGTTVTVSS.

The hyper variable regions (HVRs) of VH4 are depicted in bolded and underlined text.

In some embodiments, the HVR-H1 of any one of VH1, VH2, VH3, or VH4 has the sequence GYHFTSYWMH (SEQ ID NO: 23), the HVR-H2 of V any one of VH1, VH2, VH3, or VH4 has the sequence VIHPNSGSINYNEKFES (SEQ ID NO: 24), and the HVR-H3 of any one of VH1, VH2, VH3, or VH4 has the sequence ERDSTEVLPMDY (SEQ ID NO: 25).

The nucleic acid sequence encoding heavy chain variable domain variant 1 (VH1) is:

(SEQ ID NO: 26)
CAGGTGCAGCTGGTGCAGTCAGGGGCTGAGCTGAAGAAGCCTGGGGCTTC
AGTGAAGGTTTCCTGCAAGTCTTCTGGCTACCATTTCACCAGCTACTGGA
TGCACTGGGTGAAGCAGGCCCCTGGACAAGGCCTTGAGTGGATTGGAGTG
ATTCATCCTAATAGTGGTAGTATTAACTACAATGAGAAGTTCGAGAGCAA
GGCCACAATTACTGTAGACAAATCCACCAGCACAGCCTACATGCAACTCA
GCAGCCTGACATCTGAGGACTCGGCGGTCTATTATTGTGCAGGAGAGAGA
GATTCTACGGAGGTTCTCCCTATGGACTACTGGGGTCAAGGAACCTCAGT
CACCGTCTCCTCA.

The nucleic acid sequence encoding heavy chain variable domain variant 2 (VH2) is:

(SEQ ID NO: 27)
CAGGTGCAGCTGGTGCAGTCAGGGGCTGAGCTGAAGAAGCCTGGGGCTTC
AGTGAAGGTTTCCTGCAAGTCTTCTGGCTACCATTTCACCAGCTACTGGA

-continued

```
TGCACTGGGTGAAGCAGGCCCCTGGACAAGGCCTTGAGTGGATTGGAGTG

ATTCATCCTAATAGTGGTAGTATTAACTACAATGAGAAGTTCGAGAGCAG

AGCCACAATTACTGTAGACAAATCCACCAGCACAGCCTACATGGAGCTCA

GCAGCCTGAGATCTGAGGACACGGCGGTCTATTATTGTGCAGGAGAGAGA

GATTCTACGGAGGTTCTCCCTATGGACTACTGGGGTCAAGGAACCACGGT

CACCGTCTCCTCA.
```

The nucleic acid sequence encoding heavy chain variable domain variant 3 (VH3) is:

```
                                        (SEQ ID NO: 28)
CAGGTGCAGCTGGTGCAGTCAGGGGCTGAGCTGAAGAAGCCTGGGGCTTC

AGTGAAGGTTTCCTGCAAGTCTTCTGGCTACCATTTCACCAGCTACTGGA

TGCACTGGGTGAAGCAGGCCCCTGGACAAGGCCTTGAGTGGATTGGAGTG

ATTCATCCTAATAGTGGTAGTATTAACTACAATGAGAAGTTCGAGAGCAG

AGTCACAATTACTGTAGACAAATCCACCAGCACAGCCTACATGGAGCTCA

GCAGCCTGAGATCTGAGGACACGGCGGTCTATTATTGTGCAGGAGAGAGA

GATTCTACGGAGGTTCTCCCTATGGACTACTGGGGTCAAGGAACCACGGT

CACCGTCTCCTCAG.
```

The nucleic acid sequence encoding heavy chain variable domain variant 4 (VH4) is:

```
                                        (SEQ ID NO: 29)
CAGGTGCAGCTGGTGCAGTCAGGGGCTGAGCTGAAGAAGCCTGGGGCTTC

AGTGAAGGTTTCCTGCAAGTCTTCTGGCTACCATTTCACCAGCTACTGGA

TGCACTGGGTGCGACAGGCCCCTGGACAAGGCCTTGAGTGGATTGGAGTG

ATTCATCCTAATAGTGGTAGTATTAACTACAATGAGAAGTTCGAGAGCAG

AGTCACAATTACTGTAGACAAATCCACCAGCACAGCCTACATGGAGCTCA

GCAGCCTGAGATCTGAGGACACGGCGGTCTATTATTGTGCAGGAGAGAGA

GATTCTACGGAGGTTCTCCCTATGGACTACTGGGGTCAAGGAACCACGGT

CACCGTCTCCTCA.
```

The amino acid sequence of kappa light chain variable domain variant 1 (Vκ1) is:

```
                                        (SEQ ID NO: 5)
DVQITQSPSYLAASLGERATINCRASKSINKYLAWYQQKPGKTNKLLIYS

GSTLQSGIPARFSGSGSGTDFTLTISSLEPEDFAMYYCQQHNEYPLTFGQ

GTKLEIK.
```

The hyper variable regions (HVRs) of W1 are depicted in bolded and underlined text.

The amino acid sequence of kappa light chain variable domain variant 2 (Vκ2) is:

```
                                        (SEQ ID NO: 6)
DVQITQSPSSLSASLGERATINCRASKSINKYLAWYQQKPGKANKLLIYS

GSTLQSGIPARFSGSGSGTDFTLTISSLEPEDFAMYYCQQHNEYPLTFGQ

GTKLEIK.
```

The hyper variable regions (HVRs) of Vκ2 are depicted in bolded and underlined text.

The amino acid sequence of kappa light chain variable domain variant 3 (Vκ3) is:

```
                                        (SEQ ID NO: 7)
DVQITQSPSSLSASLGERATINCRASKSINKYLAWYQQKPGKAPKLLIYS

GSTLQSGIPARFSGSGSGTDFTLTISSLEPEDFAMYYCQQHNEYPLTFGQ

GTKLEIK.
```

The hyper variable regions (HVRs) of Vκ3 are depicted in bolded and underlined text.

The amino acid sequence of kappa light chain variable domain variant 4 (Vκ4) is:

```
                                        (SEQ ID NO: 8)
DIQLTQSPSSLSASLGERATINCRASKSINKYLAWYQQKPGKAPKLLIYS

GSTLQSGIPARFSGSGSGTDFTLTISSLEPEDFAMYYCQQHNEYPLTFGQ

GTKLEIK.
```

The hyper variable regions (HVRs) of Vκ4 are depicted in bolded and underlined text.

In some embodiments, the HVR-L1 of any one of Vκ1, Vκ2, Vκ3, or Vκ4 has the sequence has the sequence RASKSINKYLA (SEQ ID NO: 30), the HVR-L2 of any one of W1, Vκ2, Vκ3, or Vκ4 has the sequence SGSTLQS (SEQ ID NO: 31), and the HVR-L3 of any one of W1, Vκ2, Vκ3, or Vκ4 has the sequence QQHNEYPLT (SEQ ID NO: 32).

The nucleic acid sequence encoding kappa light chain variable domain variant 1 (Vκ1) is:

```
                                        (SEQ ID NO: 33)
GATGTCCAGATCACACAGTCTCCATCTTATCTTGCTGCATCTCTCGGAGA

AAGAGCTACTATTAATTGCAGGGCAAGTAAGAGCATTAACAAATACTTAG

CCTGGTATCAACAGAAACCTGGGAAAACTAATAAGCTCCTTATCTACTCT

GGCTCCACTTTGCAATCTGGAATTCCAGCAAGGTTCAGTGGCAGTGGATC

TGGTACAGATTTCACTCTCACCATCAGTAGCCTGGAGCCTGAAGATTTTG

CAATGTATTACTGTCAACAACATAATGAATACCCGCTCACGTTCGGTCAG

GGGACCAAGCTGGAGATCAAA.
```

The nucleic acid sequence encoding kappa light chain variable domain variant 2 (Vκ2) is:

```
                                        (SEQ ID NO: 34)
GATGTCCAGATCACACAGTCTCCATCTTCCCTTTCTGCATCTCTCGGAGA

AAGAGCTACTATTAATTGCAGGGCAAGTAAGAGCATTAACAAATACTTAG

CCTGGTATCAACAGAAACCTGGGAAAGCTAATAAGCTCCTTATCTACTCT

GGCTCCACTTTGCAATCTGGAATTCCAGCAAGGTTCAGTGGCAGTGGATC

TGGTACAGATTTCACTCTCACCATCAGTAGCCTGGAGCCTGAAGATTTTG

CAATGTATTACTGTCAACAACATAATGAATACCCGCTCACGTTCGGTCAG

GGGACCAAGCTGGAGATCAAA.
```

The nucleic acid sequence encoding kappa light chain variable domain variant 3 (Vκ3) is:

(SEQ ID NO: 35)
GATGTCCAGATCACACAGTCTCCATCTTCCCTTTCTGCATCTCTCGGAGA

AAGAGCTACTATTAATTGCAGGGCAAGTAAGAGCATTAACAAATACTTAG

CCTGGTATCAACAGAAACCTGGGAAAGCTCCTAAGCTCCTTATCTACTCT

GGCTCCACTTTGCAATCTGGAATTCCAGCAAGGTTCAGTGGCAGTGGATC

TGGTACAGATTTCACTCTCACCATCAGTAGCCTGGAGCCTGAAGATTTTG

CAATGTATTACTGTCAACAACATAATGAATACCCGCTCACGTTCGGTCAG

GGGACCAAGCTGGAGATCAAA.

The nucleic acid sequence encoding kappa light chain variable domain variant 4 (Vκ4) is:

(SEQ ID NO: 36)
GATATTCAGCTCACACAGTCTCCATCTTCCCTTTCTGCATCTCTCGGAGA

AAGAGCTACTATTAATTGCAGGGCAAGTAAGAGCATTAACAAATACTTAG

CCTGGTATCAACAGAAACCTGGGAAAGCTCCTAAGCTCCTTATCTACTCT

GGCTCCACTTTGCAATCTGGAATTCCAGCAAGGTTCAGTGGCAGTGGATC

TGGTACAGATTTCACTCTCACCATCAGTAGCCTGGAGCCTGAAGATTTTG

CAATGTATTACTGTCAACAACATAATGAATACCCGCTCACGTTCGGTCAG

GGGACCAAGCTGGAGATCAAA.

Sequences of Human IgG4 (5241P L248E) Heavy Chain Constant Domain

Using standard techniques, the amino acid and nucleic acid sequences encoding the human IgG4 (S241P L248E) heavy chain constant domain (i.e., CH1, CH2, CH3, and hinge region) were determined.

The amino acid sequence of human IgG4 (S241P L248E) heavy chain constant domain is:

(SEQ ID NO: 37)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFEGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK.

The S241P mutation and the L248E mutation are depicted in bolded and underlined text.

The amino acid sequence of the human IgG4 (S241P L248E) CH1 is:

(SEQ ID NO: 38)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRV.

The amino acid sequence of the human IgG4 (S241P L248E) hinge region is: ESKYGPPCPPCP (SEQ ID NO: 39). The S241P mutation is depicted in bolded and underlined text.

The amino acid sequence of the human IgG4 (S241P L248E) CH2 is:

(SEQ ID NO: 40)
APEFEGGPSVFLFPPKPKDTLMISRTPEVTCVVVDVSQEDPEVQFNWYVD

GVEVHNAKTKPREEQFNSTYRVVSVLTVLHQDWLNGKEYKCKVSNKGLPS

SIEKTISKAK.

The L248E mutation is depicted in bolded and underlined text.

The amino acid sequence of the human IgG4 (S241P L248E) CH3 is:

(SEQ ID NO: 41)
GQPREPQVYTLPPSQEEMTKNQVSLTCLVKGFYPSDIAVEWESNGQPENN

YKTTPPVLDSDGSFFLYSRLTVDKSRWQEGNVFSCSVMHEALHNHYTQKS

LSLSLGK.

The nucleic acid sequence encoding human IgG4 (S241P L248E) heavy chain constant domain is:

(SEQ ID NO: 42)
GTAAGCTTTCTGGGGCAGGCCGGGCCTGACTTTGGCTGGGGGCAGGGAGG

GGGCTAAGGTGACGCAGGTGGCGCCAGCCAGGTGCACACCCAATGCCCAT

GAGCCCAGACACTGGACCCTGCATGGACCATCGCGGATAGACAAGAACCG

AGGGGCCTCTGCGCCCTGGGCCCAGCTCTGTCCCACACCGCGGTCACATG

GCACCACCTCTCTTGCAGCTTCCACCAAGGGCCCATCCGTCTTCCCCCTG

GCGCCCTGCTCCAGGAGCACCTCCGAGAGCACAGCCGCCCTGGGCTGCCT

GGTCAAGGACTACTTCCCCGAACCGGTGACGGTGTCGTGGAACTCAGGCG

CCCTGACCAGCGGCGTGCACACCTTCCCGGCTGTCCTACAGTCCTCAGGA

CTCTACTCCCTCAGCAGCGTGGTGACCGTGCCCTCCAGCAGCTTGGGCAC

GAAGACCTACACCTGCAATGTAGATCACAAGCCCAGCAACACCAAGGTGG

ACAAGAGAGTTGGTGAGAGGCCAGCACAGGGAGGGAGGGTGTCTGCTGGA

AGCCAGGCTCAGCCCTCCTGCCTGGACGCACCCCGGCTGTGCAGCCCCAG

CCCAGGGCAGCAAGGCAGGCCCCATCTGTCTCCTCACCTGGAGGCCTCTG

ACCACCCCACTCATGCTCAGGGAGAGGGTCTTCTGGATTTTTCCACCAGG

CTCCGGGCAGCCACAGGCTGGATGCCCCTACCCCAGGCCCTGCGCATACA

GGGGCAGGTGCTGCGCTCAGACCTGCCAAGAGCCATATCCGGGAGGACCC

TGCCCCTGACCTAAGCCCACCCCAAAGGCCAAACTCTCCACTCCCTCAGC

TCAGACACCTTCTCTCCTCCCAGATCTGAGTAACTCCCAATCTTCTCTCT

GCAGAGTCCAAATATGGTCCCCCATGCCCACCATGCCCAGGTAAGCCAAC

CCAGGCCTCGCCCTCCAGCTCAAGGCGGGACAGGTGCCCTAGAGTAGCCT

GCATCCAGGGACAGGCCCCAGCCGGGTGCTGACGCATCCACCTCCATCTC

TTCCTCAGCACCTGAGTTCGAGGGGGACCATCAGTCTTCCTGTTCCCCC

CAAAACCCAAGGACACTCTCATGATCTCCCGGACCCCTGAGGTCACGTGC

GTGGTGGTGGACGTGAGCCAGGAAGACCCCGAGGTCCAGTTCAACTGGTA

CGTGGATGGCGTGGAGGTGCATAATGCCAAGACAAAGCCGCGGGAGGAGC

AGTTCAACAGCACGTACCGTGTGGTCAGCGTCCTCACCGTCCTGCACCAG

GACTGGCTGAACGGCAAGGAGTACAAGTGCAAGGTCTCCAACAAAGGCCT

-continued
CCCGTCCTCCATCGAGAAAACCATCTCCAAAGCCAAAGGTGGGACCCACG

GGGTGCGAGGGCCACATGGACAGAGGTCAGCTCGGCCCACCCTCTGCCCT

GGGAGTGACCGCTGTGCCAACCTCTGTCCCTACAGGGCAGCCCCGAGAGC

CACAGGTGTACACCCTGCCCCCATCCCAGGAGGAGATGACCAAGAACCAG

GTCAGCCTGACCTGCCTGGTCAAAGGCTTCTACCCCAGCGACATCGCCGT

GGAGTGGGAGAGCAATGGGCAGCCGGAGAACAACTACAAGACCACGCCTC

CCGTGCTGGACTCCGACGGCTCCTTCTTCCTCTACAGCAGGCTAACCGTG

GACAAGAGCAGGTGGCAGGAGGGGAATGTCTTCTCATGCTCCGTGATGCA

TGAGGCTCTGCACAACCACTACACACAGAAGAGCCTCTCCCTGTCTCTGG

GTAAA.

The nucleic acid sequence encoding the human IgG4 (S241P L248E) heavy chain CH1 is:

(SEQ ID NO: 43)
CTTCCACCAAGGGCCCATCCGTCTTCCCCCTGGCGCCCTGCTCCAGGAGC

ACCTCCGAGAGCACAGCCGCCCTGGGCTGCCTGGTCAAGGACTACTTCCC

CGAACCGGTGACGGTGTCGTGGAACTCAGGCGCCCTGACCAGCGGCGTGC

ACACCTTCCCGGCTGTCCTACAGTCCTCAGGACTCTACTCCCTCAGCAGC

GTGGTGACCGTGCCCTCCAGCAGCTTGGGCACGAAGACCTACACCTGCAA

TGTAGATCACAAGCCCAGCAACACCAAGGTGGACAAGAGAGTTG.

The nucleic acid sequence encoding the human IgG4 (S241P L248E) heavy chain hinge is:

(SEQ ID NO: 44)
AGTCCAAATATGGTCCCCCATGCCCACCATGCCCAG.

The nucleic acid sequence encoding the human IgG4 (S241P L248E) heavy chain CH2 is:

(SEQ ID NO: 45)
CACCTGAGTTCGAGGGGGGACCATCAGTCTTCCTGTTCCCCCCAAAACCC

AAGGACACTCTCATGATCTCCCGGACCCCTGAGGTCACGTGCGTGGTGGT

GGACGTGAGCCAGGAAGACCCCGAGGTCCAGTTCAACTGGTACGTGGATG

GCGTGGAGGTGCATAATGCCAAGACAAAGCCGCGGGAGGAGCAGTTCAAC

AGCACGTACCGTGTGGTCAGCGTCCTCACCGTCCTGCACCAGGACTGGCT

GAACGGCAAGGAGTACAAGTGCAAGGTCTCCAACAAAGGCCTCCCGTCCT

CCATCGAGAAAACCATCTCCAAAGCCAAAG.

The nucleic acid sequence encoding the human IgG4 (S241P L248E) heavy chain CH3 is:

(SEQ ID NO: 46)
GGCAGCCCCGAGAGCCACAGGTGTACACCCTGCCCCCATCCCAGGAGGAG

ATGACCAAGAACCAGGTCAGCCTGACCTGCCTGGTCAAAGGCTTCTACCC

CAGCGACATCGCCGTGGAGTGGGAGAGCAATGGGCAGCCGGAGAACAACT

ACAAGACCACGCCTCCCGTGCTGGACTCCGACGGCTCCTTCTTCCTCTAC

AGCAGGCTAACCGTGGACAAGAGCAGGTGGCAGGAGGGGAATGTCTTCTC

ATGCTCCGTGATGCATGAGGCTCTGCACAACCACTACACACAGAAGAGCC

TCTCCCTGTCTCTGGGTAAA.

FIG. 2 shows an alignment of the amino acid sequences of the heavy chain variable region (VH) of M1 and the amino acid sequences of the humanized VH variants VH1-VH4, and of the amino acid sequences of the kappa light chain variable region (Vκ) of M1 and the amino acid sequences of the humanized Vκ variants Vκ$_1$-Vκ4.

Construction of Composite Human Antibody Variants

All variant VH and Vκ region genes for M1 were synthesized using a series of overlapping oligonucleotides that were annealed, ligated and PCR amplified to give full length synthetic V regions with any restriction sites removed. The assembled variants were then cloned directly into the pANT expression vector system for IgG4 (S241 L248E) heavy chain and kappa light chain (FIG. 1A and FIG. 1B). The VH region was cloned using MluI and HindIII sites, and the Vκ region was cloned using BssHII and BamHI restriction sites. All constructs were confirmed by sequencing.

Expression and Purification of Antibodies

A total of 16 fully humanized antibodies were stably transfected into NS0 cells via electroporation. In addition, the chimeric antibody M1 along with two controls—chimeric VH (ChVH) with variant Vκ1 and variant VH1 with chimeric Vκ (ChVκ)—were included. Stable transfectants were selected using 200 nM methotrexate (Sigma Cat. No. M8407). Methotrexate-resistant colonies for each construct were tested for IgG expression levels using an IgG4 ELISA, and the best expressing lines were selected, expanded and frozen under liquid nitrogen. Successful transfection and stable clone selection was achieved for all of the 16 humanized M1 variants as well as chimeric M1, ChVH/Vκ1 and VH1/ChVκ antibodies. The identity of each cell line was confirmed by DNA sequencing of the variable domains from genomic DNA.

Figure 3:
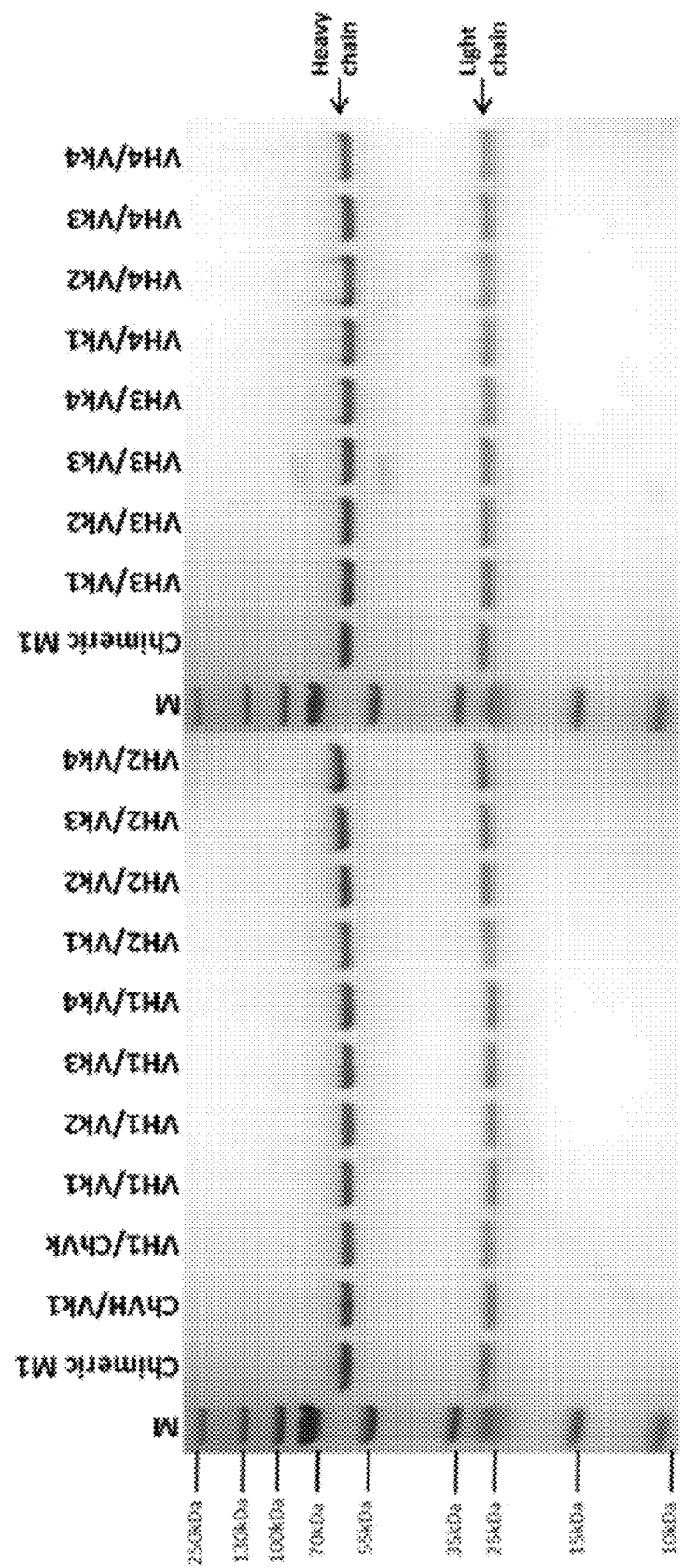
FIG. 3 depicts a Coomassie Blue-stained SDS-PAGE gel of protein A-purified antibodies. 2 μg of each sample was loaded on a NuPage 4-12% Bis-Tris gel and run at 200V for 35 min. Size marker is pre-stained protein standard Fermentas PageRuler Plus.
Figure 4A:
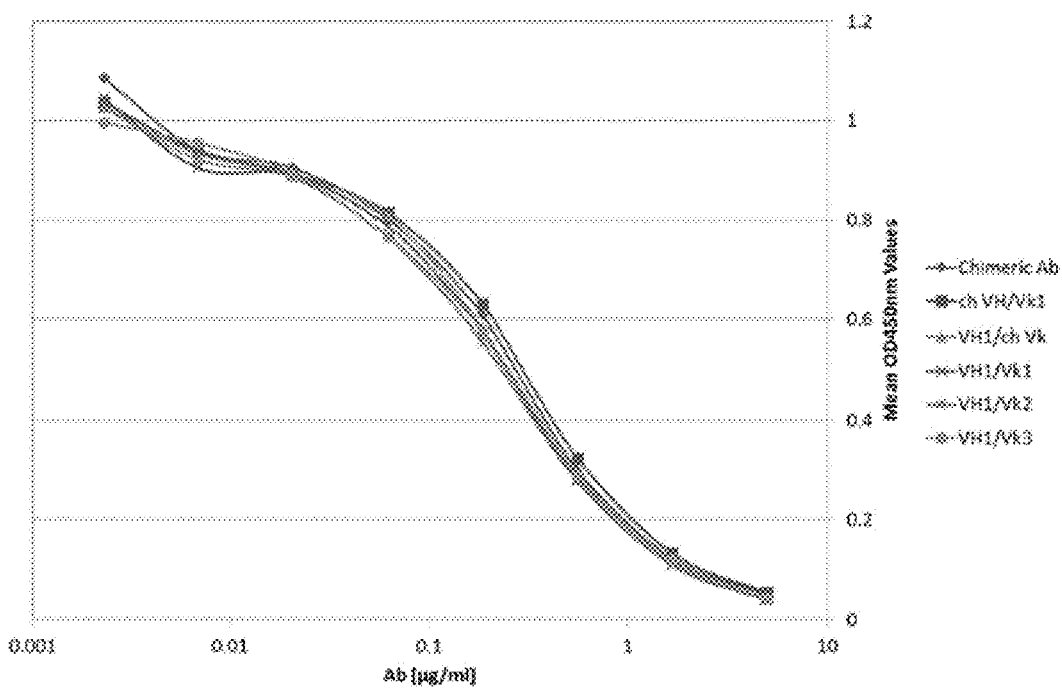
FIG. 4A, FIG. 4B, FIG. 4C, and FIG. 4D depict competition ELISA assays for human C1q. A dilution series of purified humanized anti-C1q antibodies were competed against a fixed concentration of biotinylated monoclonal antibody M1 for binding to human C1q. Bound biotinylated M1 antibody was detected using streptavidin-peroxidase conjugate and TMB substrate.
Figure 4B:
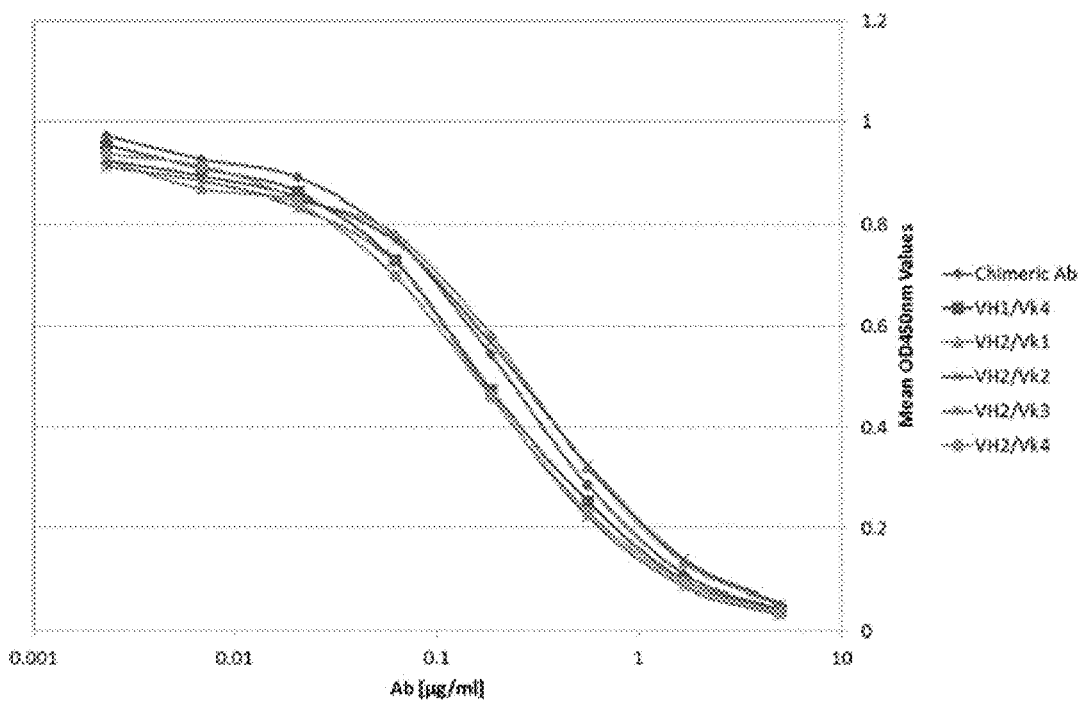
Figure 4C:
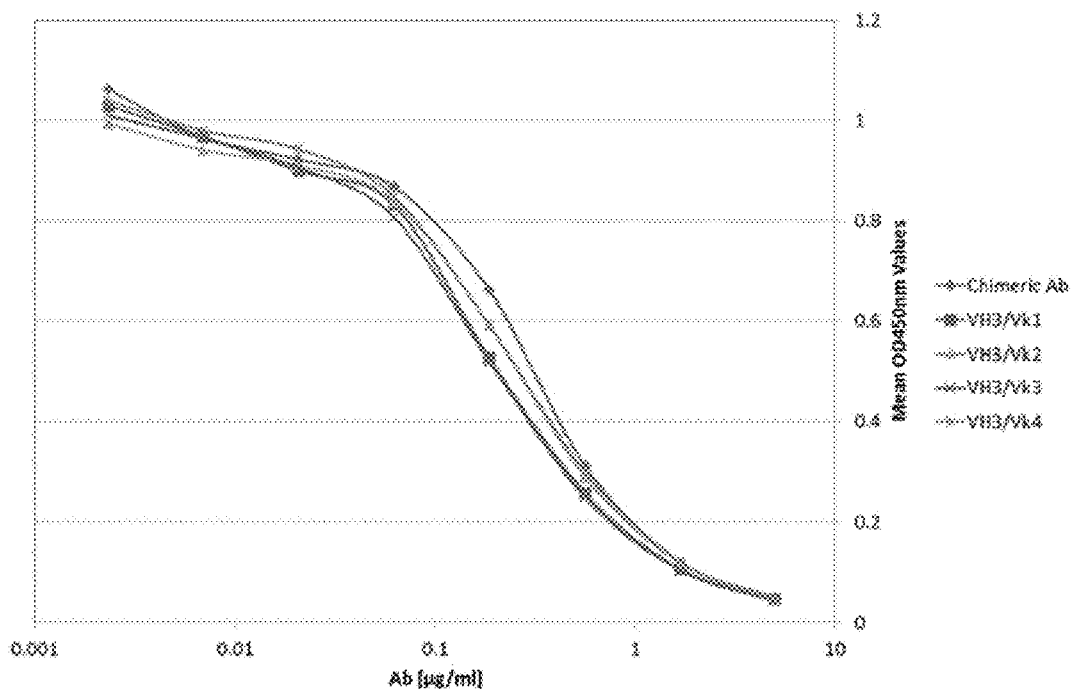
Figure 4D:
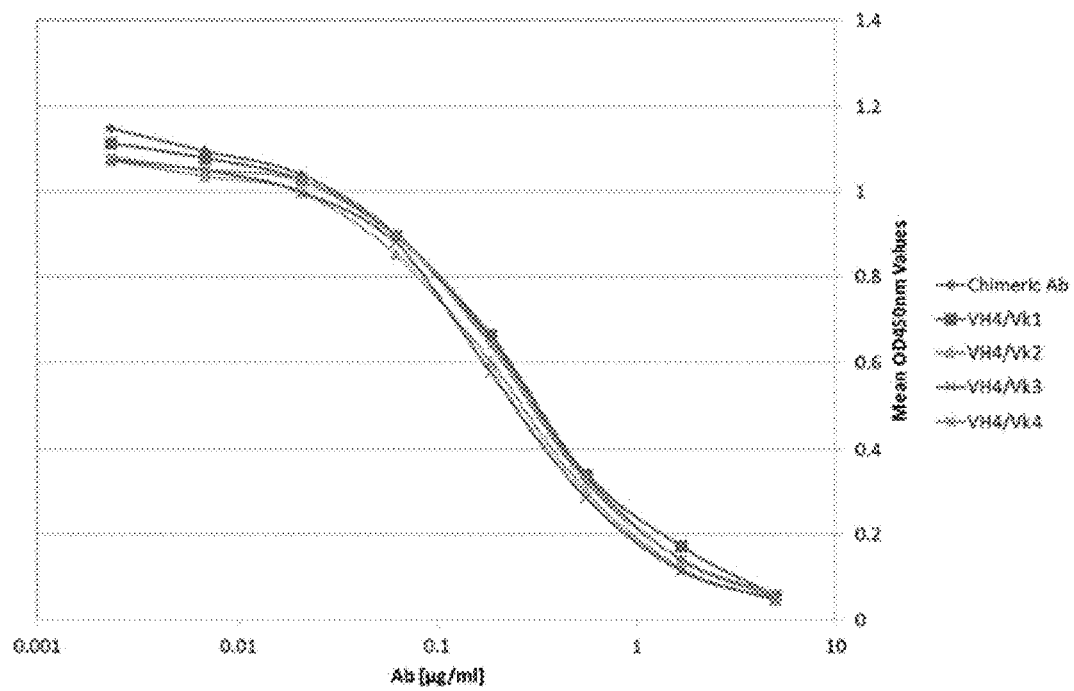

Antibodies were purified from cell culture supernatants on a Protein A sepharose column (GE Healthcare cat. co. 110034-93), buffer exchanged into PBS, pH 7.4 and quantified by $OD_{280nm}$ using an extinction coefficient based on the predicted amino acid sequences. Chimeric and humanized variant IgGs were analyzed by reducing SDS-PAGE. Bands corresponding to the predicted sizes of the VH and Vκ chains were observed with no evidence of any aggregation, degradation or other unusual features (FIG. 3).

Competition ELISA Against Human C1q Antigen

The binding of humanized M1 variants to human C1q was analyzed by competition ELISA. A three-fold dilution series of test antibody (5 µg/ml to 0.002 µg/ml) was premixed with a constant concentration of biotinylated mouse M1 antibody (0.02 µg/ml, final concentration) before incubating for 1 hour at 37° C. with shaking on plates pre-coated with human C1q at 1.0 m/ml. The binding of mouse M1 antibody was detected with streptavidin-peroxidase conjugate (Sigma-Aldrich cat. no. 55512) and TMB (3,3',5,5'-tetramethylbenzidine) substrate (Thermo Scientific cat. no. 34029). The reaction was stopped with 1M HCl, absorbance read at 450 nm on a Dynex Technologies MRX TC II plate reader and the binding curves plotted.

FIG. 4A, FIG. 4B, FIG. 4C, and FIG. 4D show that all humanized M1 variants generated have similar binding profiles to the chimeric M1 antibody. The binding curves were used to calculate $IC_{50}$ values (concentration of test antibody that inhibits labelled competitor binding by 50%)

for each antibody normalized to the $IC_{50}$ of chimeric M1 and antibody yields from NS0 transfectants were also compared (Table 1).

TABLE 1

Relative $IC_{50}$ values for binding to human C1q and protein expression levels

| Antibody | Relative $IC_{50}$ | Expression levels (µg/ml) |
| --- | --- | --- |
| Chimeric M1 | 1.00 | 12.6 |
| ChV1/Vκ1 | 1.09 | 7.0 |
| VH1/ChVκ | 0.92 | 11.9 |
| VH1/Vκ1 | 0.90 | 14.0 |
| VH1/Vκ2 | 0.84 | 14.5 |
| VH1/Vκ3 | 0.91 | 28.9 |
| VH1/Vκ4 | 0.80 | 22.6 |
| VH2/Vκ1 | 1.15 | 1.4 |
| VH2/Vκ2 | 1.12 | 3.8 |
| VH2/Vκ3 | 0.75 | 21.3 |
| VH2/Vκ4 | 0.72 | 6.1 |
| VH3/Vκ1 | 0.65 | 16.9 |
| VH3/Vκ2 | 0.82 | 8.7 |
| VH3/Vκ3 | 0.63 | 19.8 |
| VH3/Vκ4 | 0.83 | 32.2 |
| VH4/Vκ1 | 1.03 | 8.5 |
| VH4/Vκ2 | 0.84 | 1.6 |
| VH4/Vκ3 | 0.77 | 18.3 |
| VH4/Vκ4 | 0.92 | 2.4 |

Table 1 shows calculated relative $IC_{50}$ values for humanized M1 variants binding to human C1q and protein expression levels of corresponding NS0 cell line.

The normalized $IC_{50}$ data for all variants tested were in the range of 0.63 to 1.15 indicating that the binding efficiencies of all of the fully humanized M1 antibodies to human C1q were comparable to that of chimeric M1. Furthermore, most humanized variants achieved an increase in expression level compared to the chimeric antibody.

Competition ELISA Against Mouse C1q Antigen

The binding of humanized M1 variants to mouse C1q was analyzed by competition ELISA on four selected antibodies, VH1/Vκ1, VH3/Vκ3, VH3/Vκ4 and VH4/Vκ3. An irrelevant IgG4 (S241P L248E) antibody was also included as a binding control. A three-fold dilution series of test antibody (100 µg/ml to 0.046 µg/ml) was premixed with a constant concentration of biotinylated chimeric M1 antibody (0.03 µg/ml, final concentration) before incubating for 1 hour at 37° C. with shaking on plates pre-coated with mouse C1q at 5.0 m/ml. The binding of chimeric M1 antibody was detected with streptavidin-peroxidase conjugate (Sigma-Aldrich cat. no. 55512) and TMB substrate (Thermo Scientific cat. no. 34029). The reaction was stopped with 1M HCl, absorbance read at 450 nm on a Dynex Technologies MRX TC II plate reader and the binding curves plotted.

Figure 5:
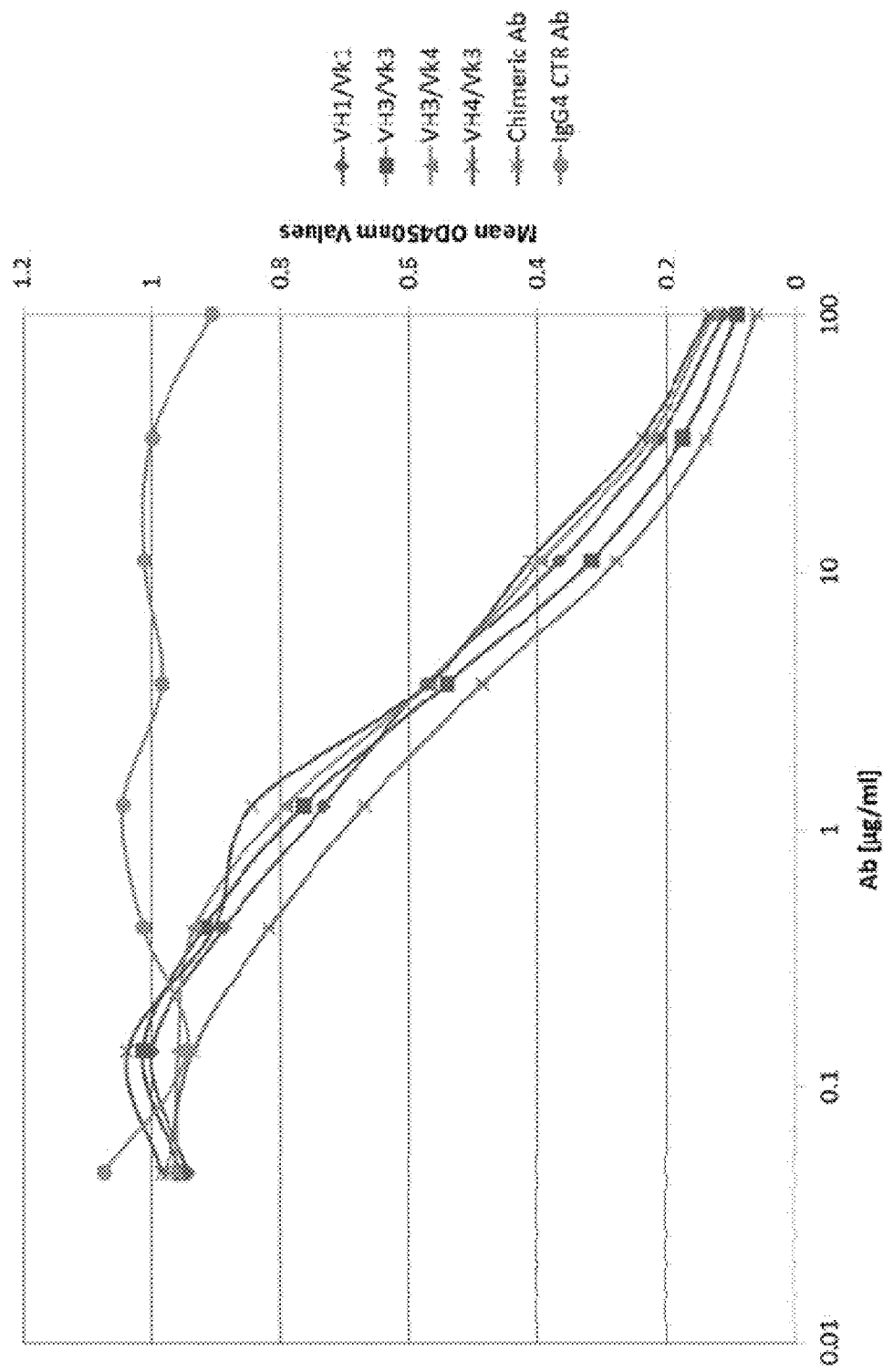
FIG. 5 depicts competition ELISA assays for mouse C1q. A dilution series of purified humanized anti-C1q antibodies were competed against a fixed concentration of the chimeric M1 antibody for binding to mouse C1q. Bound biotinylated chimeric M1 was detected using streptavidin-peroxidase conjugate and TMB substrate.

FIG. 5 shows that humanized M1 variants generated have similar binding profiles to the chimeric M1 antibody. The binding curves were used to calculate $IC_{50}$ values for each antibody normalized to the $IC_{50}$ of chimeric M1 (Table 2).

TABLE 2

Relative $IC_{50}$ values for binding to mouse C1q

| Antibody | Relative $IC_{50}$ |
| --- | --- |
| Chimeric M1 | 1.00 |
| VH1/Vκ1 | 1.62 |
| VH3/Vκ3 | 1.50 |
| VH3/Vκ4 | 1.91 |
| VH4/Vκ3 | 1.84 |

Table 2 shows calculated relative $IC_{50}$ values for humanized M1 variants binding to mouse C1q.

Conclusion

The V region genes from the murine antibody M1 were cloned into vectors to generate a chimeric antibody comprising the murine V regions combined with the human IgG4 (S241P L248E) heavy chain constant region and κ light chain constant regions. Additionally, a series of four humanized VH regions for IgG4 (S241P L248E) and four humanized Vκ regions were designed and constructed.

The chimeric antibody and the combinations of humanized V region genes (16 antibodies in total) were expressed in NS0 cells, purified and tested for binding to human C1q in a competition ELISA assay. The binding data (Table 1) were used to rank the humanized M1 variants in comparison with the chimeric M1 antibody. No significant differences in quality of the heavy and light chain bands were detected by SDS-PAGE.

Example 2: Kinetic Characterization of Humanized Anti-C1q Antibody VH3/Vκ3

Introduction

Immunological biosensors, for example Biacore™ surface plasmon resonance (SPR) instruments, that measure the binding and dissociation of antigen-antibody complexes in real time allow the elucidation of binding kinetics. The rate of dissociation and its subsequent optimization is especially important for biopharmaceutical antibody development.

The Biacore uses SPR to monitor the interaction between a surface bound molecule 'ligand' and its binding partner in solution 'analyte', in real time. SPR is an electron charge-density wave phenomenon, which arises at the surface of a metallic layer when light is reflected at the layer under conditions of total internal reflectance. The surface plasmons that are generated are sensitive to any changes in the refractive index of the medium on the opposite side of the metallic layer from the reflected light. Protein-protein interactions occurring at the surface affect the refractive index of the medium and can therefore be detected. Binding of molecules to the ligand modified sensor surface generates a response, which is proportional to the bound mass allowing small changes in the amount of bound analyte to be detected (down to low picogram levels). The technique can be used to measure affinity constants ($K_D$) over the range $10^{-5}$ M to $10^{-12}$ M, association rate constants ($k_a$) between $10^3$ $M^{-1}s^{-1}$ and $10^7$ $M^{-1}s^{-1}$, and dissociation rate constants ($k_d$) between $10^{-1}$ $s^{-1}$ and $10^{-6}$ $s^{-1}$.

The technique requires only small amounts of material and both of the interacting biomolecules can be used in a label-free form. Experimental design is important, however, as some features of the technology, and the fact that one of the proteins must be surfaced attached, can give rise to misleading results (Huber and Mueller, *Curr Pharm Des.* 2006; 12(31):3999-4021; and Lakey and Raggett, *Curr Opin Struct Biol.*, 1998. 8(1): p. 119-123).

This example describes the kinetic characterization of the interaction between the humanized anti-C1q antibody VH3/Vκ3 (both Fab fragment and full-length IgG) and the C1q protein utilizing the Biacore T200 surface plasmon resonance instrument for the high resolution.

Materials and Methods

Samples

The reagents used in this example are listed in Table 3.

TABLE 3

| Samples | |
|---|---|
| Sample | Volume at concentration (mg/ml) |
| IgG-VH3/Vκ3 | 400 µl at 1.2 mg/ml |
| Fab-VH3/Vκ3 | 450 µl at 0.3 mg/ml |
| Mouse C1q | 4 × 50 µl at 1.0 mg/ml |
| Human C1q | 10 × 50 µl at 1.0 mg/ml |

Mouse and human C1q were stored at −80° C., except once defrosted they were stored at +4° C. Fab and IgG VH3/Vκ3 were stored at +4° C. Once diluted, C1q solutions were kept on ice and used within 24 hours.

Equipment

A Biacore T200 instrument (SN: CN 12231) running Biacore T200 Evaluation Software V1.1 (Uppsala, Sweden) was used.

Materials

The following materials were obtained from Biacore as follows:

Biacore Preventative Maintenance Kit 2: BR-1006-51, Lot No. 164110

Series S CM5 Sensor Chips: BR-1006-68, Lot No. 10102398

Amine Coupling Kit: BR-1000-50, Lot No. 2027942/41

10 mM Acetate pH 5.0: BR-1003-51, Lot No. 21702813

HBS-EP Running buffer: BR-1006-69, Lot No. 2027942/59

BSA was obtained from Sigma (A3294).

Procedures

All experiments were developed with Biacore 'wizard' software. The following Biacore methods were used:

Immobilization

Kinetics/Affinity

Desorb and Sanitize

Results

VH3/Vκ3 Fab Preparation

The Fab fragment of the anti-C1q humanized antibody VH3/Vκ3 was prepared using a Fab Micro Preparation Kit following the manufacturer's protocol. The starting concentration of the full-length IgG VH3/Vκ3 was 1.88 mg/ml. To obtain sufficient amount of the Fab fragments, 6 reactions of 225 µg each of full-length IgG were digested, pooled, and purified. The purified Fab and the full-length IgG were further purified by size exclusion chromatography using a Superdex 200 Increase 10/300 GL column (GE Healthcare Cat. No. 28-9909-44) with 1× PBS as running buffer. Samples were quantified by $OD_{280nm}$ using an extinction coefficient ($EC_{(0.1\%)}$) based on the predicted amino acid sequence ($Ec_{(0.1\%)}$=1.45 for IgG VH3/Vκ3 and 1.4 for Fab VH3/Vκ3). Both samples were analyzed by non-reducing and reducing SDS-PAGE (FIG. 6). FIG. 6 depicts a Coomassie Blue-stained SDS-PAGE gel of gel filtration-purified antibodies. 1 µg of each sample was loaded on a NuPage 4-12% Bis-Tris gel (Invitrogen Cat. No. NP0322BOX) and run at 200V for 35 min. Size marker (M) is prestained protein standard Fermentas PageRuler Plus (Cat. No. SM1811). Lane 1 shows the reduced VH3/Vκ3 Fab; lane 2 shows the non-reduced VH3/Vκ3 Fab; lane 3 shows the reduced VH3/Vκ3 IgG; and lane 4 shows the non-reduced VH3/Vκ3 IgG.

Antigen Preparation

The samples of mouse C1q (mC1q) and human C1q (hC1q) antigens were stored at −80° C., and upon initial defrosting, multiple aliquots were prepared, re-frozen and stored at −80° C. Further dilutions of the analytes into HBS-EP (10 mM HEPES pH 7.4 and 150 mM NaCl, 3 mM EDTA and 0.05% (v/v) P20) were performed for the kinetic runs.

Instrument Preparation

Before running any samples, and during the study, a system check (Biacore Preventative Maintenance Kit 2) was performed. All the systems tested passed (Reagent pump, Refractometer, Injections, Noise, Mixing and Buffer Selector) indicating that the instrument was performing to criteria set by the manufacturer.

System Preparation

Upon insertion of a CM5 chip the system was primed and then normalized with BIA normalizing solution (Biacore Preventative Maintenance Kit 2). All samples were run at 25° C. with a sample rack incubated at 10° C. The chip was added to the system with HBS-EP used as the running buffer; prior to immobilization the chip surface was primed with two injections of 50 mM NaOH.

Immobilization Conditions

Due to concerns about stability, two chips were prepared; one with hC1q and mC1q (Chip A11) as ligands and one with IgG and Fab (Chip A13) as ligands. Immobilization for m/h C1q was carried out at a protein concentration of 5 µg/ml in 10 mM acetate buffer pH 5.5, whereas immobilization for IgG and Fab was carried out at a protein concentration of 0.5-2 µg/ml in 10 mM acetate buffer pH 5.0, both on a CM5 Series S sensor chip (Biacore). The final response levels for Chips A11 and A13 used in the kinetic analysis are shown in Table 4.

TABLE 4

| | Final response level (RU) | | | |
|---|---|---|---|---|
| | $F_c1$ | $F_c2$ | $F_c3$ | $F_c4$ |
| A11 | Blank | hC1q 808.3 | mC1q 801.3 | mC1q 824.1 |
| A13 | Blank | Fab 10.4 | IgG 12.8 | IgG 51.9 |

Table 4 depicts the final immobilization levels achieved from Chips A11 and A13 for each flow cell ($F_c$).

For kinetic experiments the amount of immobilized/captured ligand needs to be limited to avoid mass transfer effects at the surface of the chip and the surface should ideally have an analyte maximum binding response ($R_{max}$) of 100-150 response units (RUs). The amount of ligand to immobilize is therefore calculated using Equation 1:

$$\text{Analyte Binding Capacity}(RU) = \frac{\text{analyte } Mw}{\text{ligand } Mw} \times \text{immobilised ligand}(RU) \times Sm$$

An average MW of 410 kDa (literature and reagent manufacturers) for both mC1q and hC1q, 150 kDa for IgG (estimated value for antibodies), and 50 kDa for the Fab (estimated) were employed. Aiming for 100 RU for $R_{max}$ and the stoichiometry (Sm) as 1, an ideal target amount of C1q to immobilize would be ~820 RUs. Due to concerns associated with avidity for the Fab and IgG immobilized surfaces, the amount of immobilized ligand was kept as low as possible (limit of 10 RUs in Biacore immobilization software).

Non-Specific Binding (NSB) Control

Non-specific binding can be due to either the analyte or analyte contaminants, interacting with the ligand (non-specific and difficult to detect), the capture protein, or the sensor chip surface. When analyzing the response of the blank $F_c1$ surface after a relatively high concentration (500 nM), 300 second injection of both mC1q and hC1q, significant non-specific binding (NSB) was observed. An additional blocking step, a post-ligand immobilization of 50 μg/ml BSA (10 mM acetate pH 4.25) was therefore included (Moore et al., MAbs. 2010 March-April; 2(2):181-9). The BSA blocking step was also repeated on the reference channel (Fc1); for both, immobilization levels were 8000 RU. No NSB was observed using Fab, or IgG at 500 nM on the CM5 surface, and at the concentration used in the kinetic runs, no NSB to the BSA blocked surface was seen.

Regeneration Scouting

Where required, either a single injection or two sequential 30 second injections of 1 M NaCl/50 mM NaOH were used to regenerate all surfaces. A 180 second wait step was introduced after the last regeneration injection to allow the surface to stabilize before starting the next binding cycle.

Surface Performance

The performance of the surface was analyzed by repeated control injections of analyte at the start, interspersed and at the end of a kinetic run. Stable binding was typically observed throughout the kinetic run, highlighting the suitability of the system for kinetic analysis.

Mass Transfer Control

Mass transport limitation occurs when the rate of association contains a significant component associated with the rate of transport of the analyte to and from the chip surface. Where mass transfer is found to be significant, the resulting kinetic analysis could be inaccurate. Lowering the density of immobilized ligand, or increasing the flow rate, can reduce mass transport limitations. From previous experience of using low density surfaces and similar MW antigens a flow rate of 40 μL/min was selected for this study.

Linked Reactions Control

The linked reaction control experiment is used to assess the ligand-analyte interaction to check for deviations from a 1-to-1 binding model. The analyte is injected over the surface for different periods of time (contact times) and the dissociation rate is analyzed to determine if it varies with the contact time. If such a relationship is observed, it indicates that a second interaction event is taking place after the initial binding event that results in a stabilized complex at the surface.

Avidity associated with a single hC1q binding two antibodies could be expected if the antibody was employed as the ligand. A linked reaction control was therefore performed to provide supporting evidence for more complex data analysis models.

Kinetic Analysis

A 1:1 binding model was initially assumed for all ligand/complex interactions (see Equation 2). Due to ligand activity and drift in the baseline (BSA blocked surfaces) the parameter $R_{max}$ was set to local as opposed to global analysis for selected kinetic analyses. If necessary, additional models, such as Heterogeneous Ligand (see Equation 3) and Bivalent Binding (see Equation 4), were also assessed for goodness of fit.

Equation 2

1-to-1 binding:

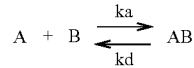

Equation 3

Heterogeneous ligand:

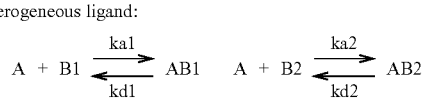

Equation 4

Bivalent (Avidity):

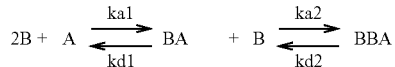

Antibody Characterization

Both C1q complexes were immobilized based on concerns over avidity (i.e., two immobilized antibodies binding C1q), and the very high levels of NSB observed using mC1q and to a lesser extent hC1q to the CM5 surface (charge mediated estimated C1q: pI 8-9). Single cycle kinetics (SCK) were used initially to derive estimated kinetic constants due to uncertainty over the stability of the C1q complex and the regeneration conditions. Full kinetic analysis was performed after SCK. The ligand stability control injections performed during the kinetic run indicated either the regeneration conditions used were inactivating the ligand, or the ligand itself was unstable at 25° C. during the 48 hours required for kinetic analysis. The lower affinity displayed by mC1q for Fab allowed kinetic analysis to be performed without surface regeneration.

Due to stability issues both Fab and IgG were used as ligands for kinetic analysis, with the amount of ligand minimized to avoid potential avidity.

Kinetic data was obtained at a flow rate of 40 μL/min to minimize any potential mass transfer effects. Two repeats of the blank (no antigen) and a single concentration of the analyte were programmed into the kinetic run in order to check the stability of both the surface and analyte over the kinetic cycles. For the initial kinetic runs 3.33-fold dilutions of analyte were run. For kinetic analysis and on subsequent runs a 2-fold dilution range was selected.

The association phase was monitored for 500 seconds to allow some of the higher concentrations of analyte to reach steady state. In order to observe a sufficient signal decrease (≥10%) during the dissociation phase of the kinetic cycle, dissociation was measured for up to 10,800 seconds to allow sufficient dissociation to occur for accurate assessment of the kinetics. The signal from the reference channel $F_c1$ was subtracted from that of $F_c2$, $F_c3$, and $F_c4$.

The kinetic parameters for the interaction of mC1q and the Fab fragment of VH3/Vκ3 in various assay formats are shown in Table 5. The $K_D$ value for mC1q when used as an analyte was 123 nM, and the $K_D$ value for mC1q when used as a ligand was 677 nM. The difference in the KD values reported could be due to the mode of interaction or the effect of chemically coupling a multi-subunit mC1q to a surface, resulting in changes to the secondary or tertiary structure of the protein.

TABLE 5

Kinetic analysis with mouse C1q

| Ligand | Analyte | $k_a$ (1/Ms) | SE ($k_a$) | $k_d$ (1/S) | SE ($k_d$) | $R_{max}$ (RU) | SE ($R_{max}$) | Chi² (RU²) | $K_D$ (nM) |
|---|---|---|---|---|---|---|---|---|---|
| mC1q | Fab | $6.23 \times 10^3$ | $1.4 \times 10^2$ | $4.6 \times 10^{-3}$ | $1.7 \times 10^{-5}$ | 37.0 | 0.6 | 0.8 | 747.9 |
|  | VH3/Vκ3 | $6.9 \times 10^3$ | $2.4 \times 10^2$ | $4.1 \times 10^{-3}$ | $1.0 \times 10^{-4}$ | 33.4 | 0.5 | 0.9 | 606.6 |
|  | Mean | $6.5 \times 10^3$ |  | $4.3 \times 10^{-3}$ |  | 35.2 |  |  | 677.3 |
|  | Std | $5.0 \times 10^2$ |  | $3.1 \times 10^{-4}$ |  | 2.6 |  |  | 99.9 |
| Fab VH3/Vκ3 | mC1q | $4.5 \times 10^5$ | $2.6 \times 10^4$ | $5.6 \times 10^{-2}$ | $3.4 \times 10^{-3}$ | 88.6 | 0.6 | 1.9 | 125.6 |
|  |  | $1.7 \times 10^5$ | $1.8 \times 10^3$ | $9.1 \times 10^{-3}$ | $5.4 \times 10^{-5}$ | 50.0 | 0.3 | 5.6 | 121.2 |
|  | Mean | $3.1 \times 10^5$ |  | $3.2 \times 10^{-2}$ |  | 69.3 |  |  | 123.4 |
|  | Std | $2.0 \times 10^5$ |  | $3.3 \times 10^{-2}$ |  | 27.3 |  |  | 3.1 |

Table 5 depicts the kinetic parameters for the 1-to-1 interactions of mC1q and Fab as determined using the Biacore T200. The Chi2 values show how well the association and dissociation data fits the proposed binding model. The lower the value the better the fit. The associated SE values for the rate constants represent the uncertainty associated with fitting the data to the model described, and do not represent the total uncertainty for the true kinetic values. The mean response data represents the average kinetic values and the associated SD from 2 independent analyses.

The kinetic parameters for both the IgG and Fab interactions with hC1q were in the low picomolar range (Table 6 for 1-to-1 model and Table 7 for the heterogeneous model). In order to avoid avidity, hC1q was initially used as the ligand, however this limited the analysis to single cycle kinetics and the use of more complex models, for example, heterogeneous ligand binding models (Equation 3), that may represent the different forms of hC1q structure that were associated with chemical coupling of a multi-subunit protein to a surface. When hC1q was used as the analyte both IgG and Fab were immobilized at the lowest concentrations possible to avoid avidity. The data was analyzed using a 1-to-1 model and a more complex bivalent analyte model (Equation 4). Complex model fitting did not significantly improve the fitting metrics and a linked reaction control did not show a time-dependent dissociation phase. The results indicate that, at the lower ligand density, the binding was predominately not due to avidity. Using hC1q as the analyte, the KD value for the full-length VH3/Vκ3 IgG was 5.8 pM and the KD value for the VH3/Vκ3 Fab was 8.6. It should be noted that the dissociation rate was too slow to measure accurately with this technique. Longer dissociation times were limited by the stability of the system (BSA blocking layer) and the low levels of binding used to avoid avidity. These results correlate well with results obtained using hC1q as a ligand.

TABLE 6

Kinetic analysis with human C1q

| Ligand | Analyte | $k_a$ (1/Ms) | SE ($k_a$) | $k_d$ (1/S) | SE ($k_d$) | $R_{max}$ (RU) | SE ($R_{max}$) | Chi² (RU²) | $K_D$ (pM) |
|---|---|---|---|---|---|---|---|---|---|
| hC1q | Fab VH3/Vκ3 | $5.2 \times 10^4$ | 82 | $4.6 \times 10^{-8}$ | $1.3 \times 10^{-7}$ | 154.9 | 0.033 | 14.8 | 0.87 |
|  | IgG VH3/Vκ3 | $3.9 \times 10^4$ | 96 | $3.1 \times 10^{-7}$ | $5.3 \times 10^{-8}$ | 387.9 | 0.11 | 206 | 7.9 |
| Fab VH3/Vκ3 | hC1q | $1.1 \times 10^6$ | 190 | $9.1 \times 10^{-6}$ | $1.4 \times 10^{-8}$ | 13.5 | 0.0015 | 0.0773 | 8.6 |
| IgG VH3/Vκ3 | hC1q | $9.6 \times 10^5$ | 360 | $6.4 \times 10^{-6}$ | $2.9 \times 10^{-8}$ | 6.5 | $1.5 \times 10^{-3}$ | 0.076 | 6.7 |
|  |  | $1.1 \times 10^6$ | 190 | $5.1 \times 10^{-6}$ | $1.4 \times 10^{-8}$ | 17.4 | 0.002 | 0.143 | 4.9 |
|  | Mean | $1.0 \times 10^6$ |  | $5.8 \times 10^{-6}$ |  |  |  |  | 5.8 |
|  | Std | $6.2 \times 10^4$ |  | $9.1 \times 10^{-7}$ |  |  |  |  | 1.3 |

Table 6 depicts the kinetic parameters for the 1-to-1 interactions of hC1q with Fab, or IgG as determined using the Biacore T200. Legend as Table 5. Data highlighted in red indicate poor fitting criteria, these data sets have therefore been analyzed using a more complex model (Table 7).

TABLE 7

Kinetic analysis for heterogeneous ligand interaction

| Ligand | Analyte | $k_a1$ (1/Ms) | $k_d1$ (1/S) | $k_a2$ (1/Ms) | $k_d2$ (1/S) | $R_{max}1$ (RU) | $R_{max}2$ (RU) | Chi² (RU²) | $K_D1$ (nM) | $K_D2$ (nM) |
|---|---|---|---|---|---|---|---|---|---|---|
| hC1q | Fab VH3/Vκ3 | $1.3 \times 10^5$ | $2.3 \times 10^{-5}$ | $1.8 \times 10^4$ | $6.3 \times 10^{-8}$ | 80.3 | 78.7 | 0.1 | 175.0 | 3.4 |
|  | IgG VH3/Vκ3 | $2.0 \times 10^5$ | $4.6 \times 10^{-6}$ | $1.6 \times 10^4$ | $1.1 \times 10^{-7}$ | 152.6 | 247.1 | 2.41 | 22.7 | 7.3 |

Table 7 depicts the kinetic parameters for the heterogeneous ligand interactions of hC1q and Fab, or IgG as determined using the Biacore T200. Legend as Table 5. Data fit to a heterogeneous ligand model to represent the expected heterogeneity of immobilizing a multi-subunit protein on a surface.

Conclusion

The interaction of hC1q and mC1q with full-length IgG and the Fab fragment of VH3/Vκ3 5 was analyzed using both species as ligands. Issues with the stability and chemical coupling of C1q complexes to the CM5 dextran surface required the development of an IgG and Fab surface; the results indicate that the binding mode observed with this surface was mainly 1-to-1, i.e., the kinetic profile did not show signs of avidity. Both the full-length IgG and Fab fragment of VH3/Vκ3 displayed tight binding in the low picomolar range for hC1q (5.8 and 8.6 pM, respectively), whereas a lower affinity was observed for mC1q binding to the Fab fragment of VH3/Vκ3 (123 nM).

Example 3: Humanized Anti-C1q Antibodies Inhibit Complement-Mediated Hemolysis

Humanized anti-C1q antibodies were tested in human and rodent hemolytic assays (CH50) for their ability to neutralize C1q and block its activation of the downstream complement cascade.

The humanized anti-C1q antibodies utilized in this example were produced as described in Example 1. The following humanized antibodies from Example 1 were utilized: the antibody VH1/Vκ1 (2B12), the antibody VH3/Vκ3 (5H7), the antibody VH3/Vκ4 (3F1), and the antibody VH4/Vκ3 (1D3). The mouse monoclonal antibody M1 (ANN-005) and the chimeric M1antibody (3E2) were also utilized as controls.

CH50 assays were conducted essentially as described in *Current Protocols in Immunology* (1994) Supplement 9 Unit 13.1. In brief, 5 microliters (µl) of human serum (Cedarlane, Burlington, N.C.) or 0.625 µl of Wistar rat serum was diluted to 50 µl of GVB buffer (Cedarlane, Burlington, N.C.) and added to 50 µl of the humanized antibodies (1 µg) diluted in GVB buffer. The antibody:serum mixture was pre-incubated for 30 minutes on ice and then added to 100 µl of EA cells ($2 \times 10^8$/ml) for both rat and human assays. The EA cells were generated exactly as specified in Current Protocols using Sheeps blood in Alsever's (Cedarlane Cat #CL2581) and hemolysin (Cedalane Cat #CL9000). The EA cells, serum and antibody mixture was incubated for 30 minutes at 37° C. and then placed on ice. Next 1.2 ml of 0.15 M NaCl was added to the mixture and the $OD_{412}$ of the sample was read in a spectrophotometer to determine the amount of cell lysis. The percent inhibition of the test antibodies was determined relative to a control mouse IgG1 antibody (Abcam ab18447).

Figure 7A:
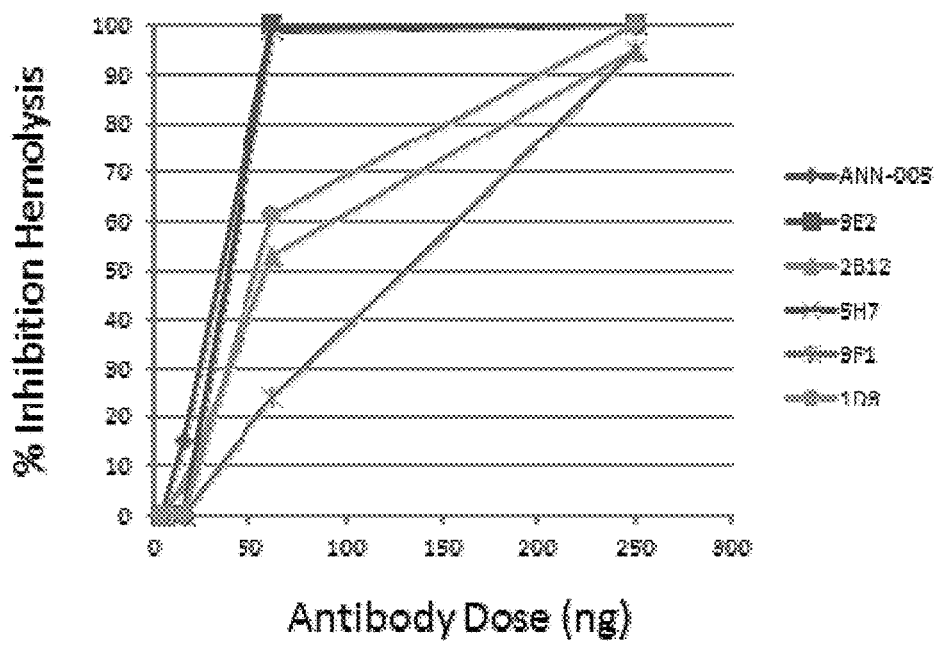
FIG. 7A and FIG. 7B illustrate the C1q-neutralizing activities of anti-C1q antibodies in human, and rat CH50 hemolytic assays in a dose-response format.

Four C1q-binding antibodies (2B12, 5H7, 3F1, and 1D3) were tested for their C1q neutralizing activity in the human CH50 hemolysis assay in a dose-response format (FIG. 7A). Each of the antibodies was tested at doses of 3.9 ng, 15.9 ng, 62.5 ng, and 260 ng, which correspond to an effective dosing range that results in the anti-C1q antibody binding to C1q with a stoichiometry that ranges from approximately 10:1 to approximately 1:1. The murine anti-C1q antibody M1 (ANN-005) and the chimeric M1 antibody (3E2) were used as references. The VH3/Vκ3 antibody (5H7) inhibited CH50 hemolysis in a dose-dependent manner to degree that was comparable to both the murine M1 antibody and the chimeric M1 antibody (FIG. 7A). Moreover, approximately 60 ng of the VH3/Vκ3 antibody (5H7), the VH4/Vκ3 antibody (1D3), and the VH1/Vκ1 antibody (2B12) was required to inhibit 50% of the hemolysis observed (FIG. 7A). Approximately 250 ng of the antibody VH3/Vκ4 (3F1) was required to inhibit approximately 95% of the hemolysis observed (FIG. 7A).

Figure 7B:
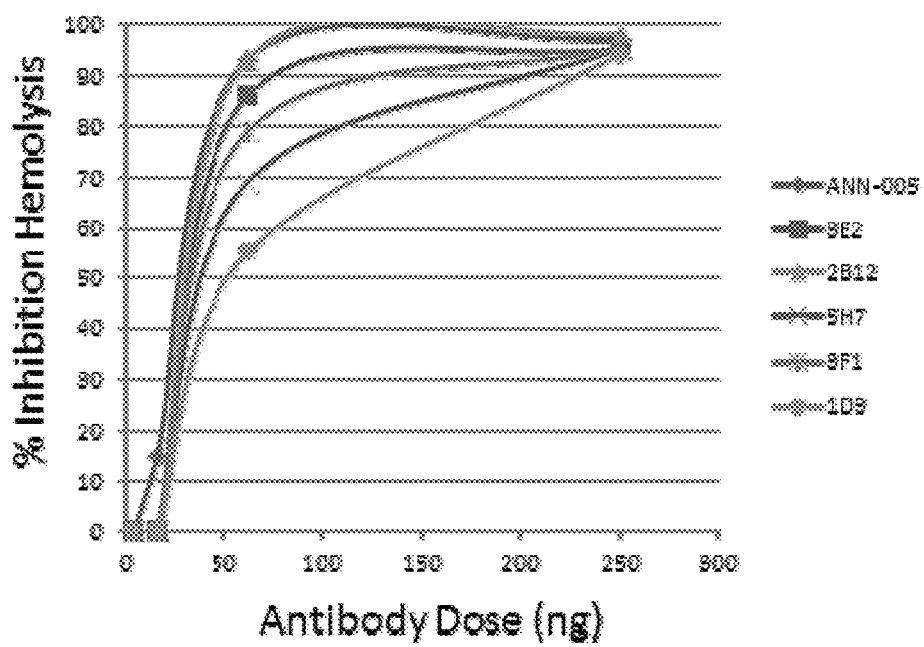

Four C1q-binding antibodies (2B12, 5H7, 3F1, and 1D3) were also tested for their C1q neutralizing activity in the rat CH50 assays (FIG. 7B). Each of the antibodies was tested at doses of 3.9 ng, 15.9 ng, 62.5 ng, and 260 ng, which correspond to an effective dosing range that results in the anti-C1q antibody binding to C1q with a stoichiometry that ranges from approximately 10:1 to approximately 1:1. Testing was conducted in dose-response formats. The murine anti-C1q antibody M1 (ANN-005) and the chimeric M1 antibody (3E2) were used as references. The VH1/Vκ1 antibody (2B12) inhibited CH50 hemolysis in a dose-dependent manner to degree that was comparable to both the murine M1 antibody and the chimeric M1 antibody (FIG. 7B). Moreover, approximately 60 ng of the VH1/Vκ1 antibody (2B12), the antibody VH3/Vκ4 (3F1), the VH3/Vκ3 antibody (5H7), and the VH4/Vκ3 antibody (1D3) was required to inhibit approximately 50% to approximately 80% of the hemolysis observed (FIG. 7B).

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Example 4: Intravenous Dosing Study in Monkey to Evaluate Pharmacokinetics of Humanized Anti-C1q Antibody, Pharmacodynamic Effects on Serum C1q Levels and Ex-Vivo Complement Mediated Hemolysis Cynomolgus monkeys were dosed with humanized anti-C1q antibody VH3/Vκ3 (5H7) via single intravenous bolus injection (I.V.) at 15 and 100 mg/Kg dose (N=2 per dose, 1 male and 1 female monkey per dose).

Blood samples were collected at the following time points—Day 1: pre-study, 0.5, 2, 4, 8, 12, 24, 72, 96 and 120 hours post dose and on Days: 7, 9, 12, 15, 18 and 21. Blood samples were allowed to clot, serum was separated by centrifugation and then stored frozen at −80 C until analysis.

Determination of serum levels of VH3/Vκ3 (5H7) from monkey samples: Serum anti-C1q antibody levels were measured using a direct ELISA with hC1q used as the capture analyte, followed by detection of human 5H7 antibody. Black 96 well ELISA plates (Corning, Cat#3925) were coated with human C1q (Complement Technology A099) at 2 µg/mL. After overnight incubation at 4 C, plates were washed thrice with Dulbecco's phosphate buffered saline (DPBS) (Thermo Scientific 28372) and blocked overnight at 4° C. with DPBS containing 3% BSA. Next day, blocking solution was removed and 5H7 standards or individual serum samples at a range of dilutions (2000 to 2000000-fold) were added to the plates at 50 µL per sample in assay buffer, DPBS containing 0.3% BSA and 0.1% tween (KPL Inc. 51-12-10). Samples were incubated at room temperature, shaking at 300 rpm for 1 hr. Then, 50 µL of goat anti-human FC antibody conjugated with alkaline phosphatase (Jackson Immuno research, 109-055-098) was added at a concentration of 0.5 µg/mL in assay buffer. After incubation for 1 hr at room temperature, plates were washed three times in DPBS containing 0.05% tween. Each wash was for a duration of 10 minutes with shaking at 300 rpm on a plate shaker. Plates were then tapped dry and developed using alkaline phosphatase substrate incubation for 20 minutes (Life Technologies, #T2214). Luminescence counts were read on a Perkin Elmer envision reader. Standard curves were fit using 4PL logistic fit and unknown signal counts were converted μg/mL concentration and plotted using Graphpad Prism.

Determination of serum C1q levels from monkey samples: Serum levels of C1q were determined using two distinct hC1q specific ELISA assays. In both ELISA assays, JL1, an antibody that binds to the collagen tail of C1q was used as the capture antibody (Abcam ab71940). In the first assay, the murine version of VH3/Vκ3 (5H7) or M1, which binds to the same site as 5H7, was used as detection antibody to isolate Free C1q levels. In the second assay, JL1 was used as the detection antibody to measure C1q which is both free and bound to ANX in the serum samples.

Black 96 well ELISA plates (Corning, Cat#3925) were coated with JL1 at 1 μg/mL. After overnight incubation at 4 C, plates were washed thrice with Dulbecco's phosphate buffered saline (DPBS) (Thermo Scientific 28372) and blocked overnight with DPBS containing 3% BSA at 4° C. Next day, blocking solution was removed and C1q standards or individual serum samples were run at dilutions in the range of 1000× to 10000×, in assay buffer DPBS with 0.3% BSA and 0.1% tween, at 50 μL per sample. Following incubation at room temperature for 1 hr, 50 uL of respective alkaline phosphatase conjugated antibodies M1 or JL1 were added, at a final concentration of 200-400 ng/mL in assay buffer. Samples were incubated overnight with shaking at 4 C. Next day, plates were washed three times in DPBS containing 0.05% tween. Each wash was for a duration of 10 minutes with shaking at 300 rpm on a plate shaker. Plates were then tapped dry and developed using alkaline phosphatase substrate incubation for 20 minutes. Luminescence counts were read on a Perkin Elmer envision reader. Standard curves were fit using 4PL logistic fit and unknown signal counts were converted to concentration, dilution correction and then plotted using Graphpad Prism.

Determination of ex-vivo hemolysis activity in monkey serum samples: The hemolysis assays were similar to that in example 3 with the following modification. Monkey serum samples from the study were diluted 1:50 in GVB++ buffer solution (Complement Technology Cat# B100) and mixed with an equal volume of antibody sensitized sheep red blood cells at 17 million cells/mL (Complement Technology Cat# B201). Samples were incubated for 1 hr at 37 C. Control wells were set up to determine baseline (buffer only without any serum) and 100% hemolysis (using deionized water). Samples were then spun down and supernatants were transferred to clear ELISA plates and absorbance read at 415 nm. The absorbance for all samples were baseline subtracted and normalized to 100% hemolysis (deionized water). At the 1:50 dilution, serum samples showed 50-70% of hemolysis observed with water. % Hemolysis was plotted for each individual monkey following baseline normalization.

Figure 8:
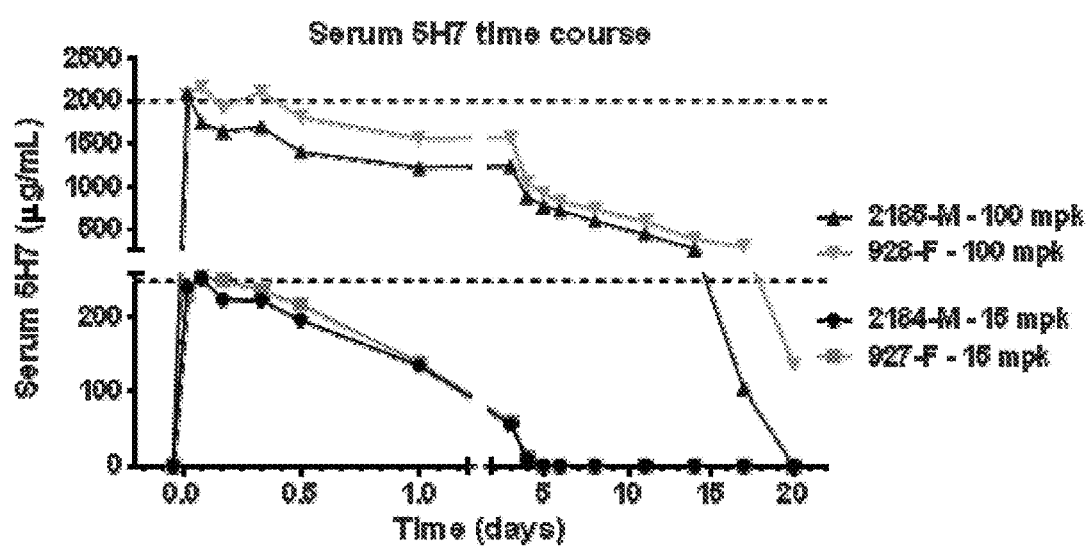
FIG. 8 depicts the time course of serum 5H7 levels in monkeys for single IV dose at 15 and 100 mg/Kg.
Figure 9A:
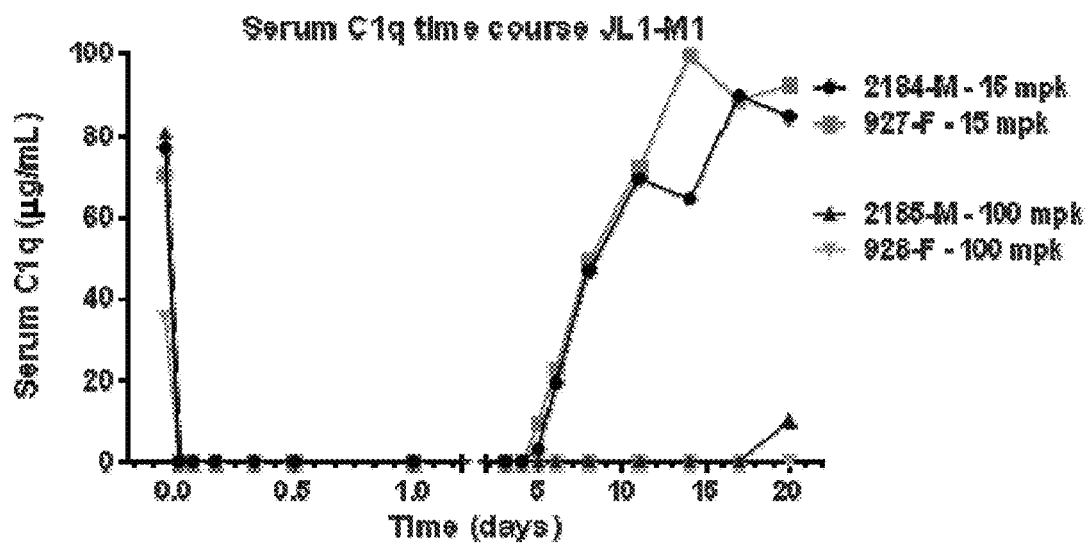
FIG. 9A and FIG. 9B illustrates the time course of serum C1q levels in monkeys for single IV dose at 15 and 100 mg/Kg.
Figure 9B:
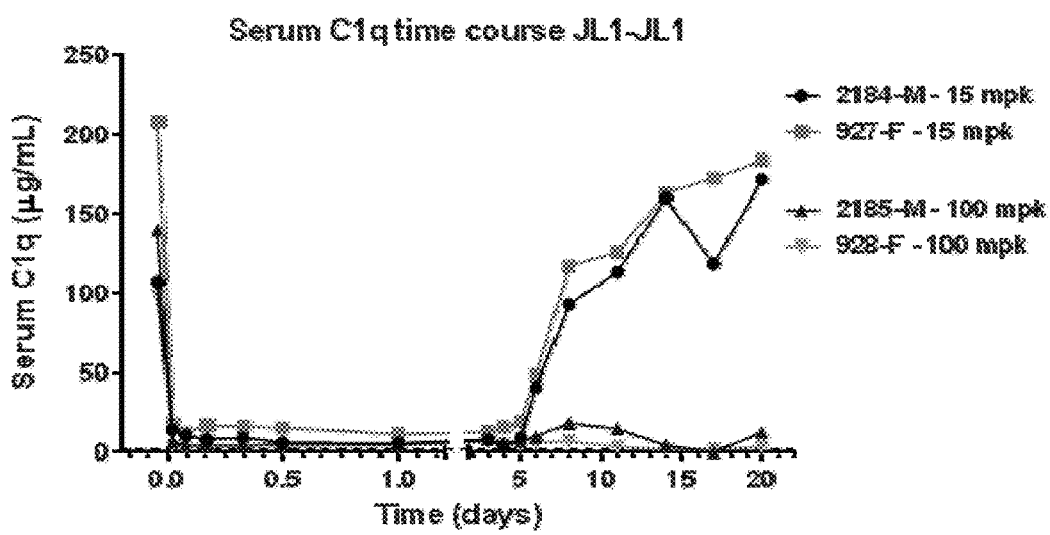
Figure 10:
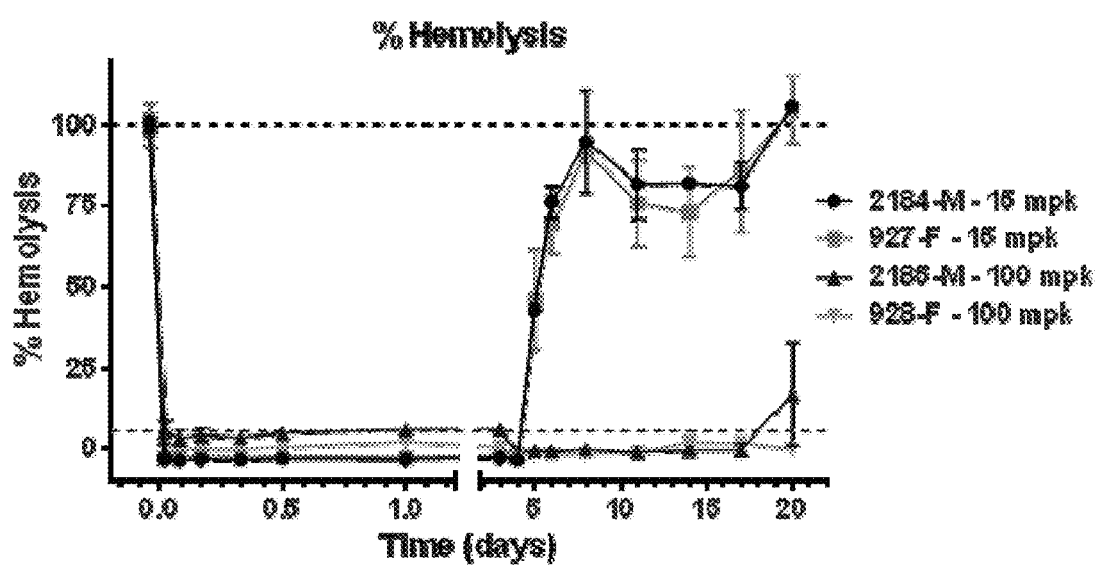
FIG. 10 shows sustained reduction of serum hemolysis in monkeys for single IV dose at 15 and 100 mg/Kg.

A dose dependent increase in serum 5H7 levels was observed following IV dosing with a maximal exposure of ~250 ug/mL at the 15 mg/Kg dose and ~2000 ug/mL at the 100 mg/Kg dose. Sustained serum levels of 5H7 were evident over the 20 days of sampling at the 100 mg/Kg dose, while serum 5H7 levels declined to levels below limit of detection after 4 days at the 15 mg/Kg dose (FIG. 8). Serum C1q levels (JL1-M1 assay) were reduced >90% over 5 days at the 15 mg/Kg dose and recovered back to baseline between 5-11 days after onset of dosing (FIG. 9A). In contrast, the 100 mg/Kg dose led to a sustained reduction of serum C1q levels up to 20 days after onset of dosing (FIG. 9A). A similar pattern of reduction and time course of serum C1q was observed with the JL1-JL1 assay (FIG. 9B). The observation of robust and sustained reduction in serum C1q in 2 independent ELISA assays, one with a detection antibody that binds to the same site on C1q as 5H7 and the other with detection antibody against an independent site on C1q, suggests that serum C1q levels are cleared following treatment with 5H7. Consistent with the reduction in serum C1q levels, a sustained reduction of ex-vivo hemolysis was observed at the 100 mg/Kg dose up to 20 days after onset of dosing (FIG. 10). At the 15 mg/Kg dose of ANX, hemolysis was reduced >90% over 5 days and recovered back to baseline between 5-11 days after onset of dosing (FIG. 10).

These results demonstrate that the anti-C1q antibody VH3/Vκ3 (5H7) shows a robust pharmacokinetic exposure and time course along with sustained reduction of serum C1q levels and hemolysis in cynomolgus monkeys.

Deposit of Material

The following material has been deposited according to the Budapest Treaty in the American Type Culture Collection, ATCC Patent Depository, 10801 University Blvd., Manassas, Va. 20110-2209, USA (ATCC):

| Sample ID | Isotype | Date | Accession No. |
|---|---|---|---|
| Mouse hybridoma C1qM1 7788-1(M) 051613 producing anti-C1q antibody M1 | IgG1, kappa | Jun. 6, 2013 | PTA-120399 |

---

What is claimed is:

1. A humanized anti-C1q antibody, wherein the antibody comprises:
   a) a heavy chain variable domain, and the heavy chain variable domain comprises an amino acid sequence selected from SEQ ID NOs: 1-4, or an amino acid sequence with at least about 95% homology to the amino acid sequence selected from SEQ ID NOs: 1-4 and wherein the heavy chain variable domain comprises an HVR-H1 having the amino acid sequence of SEQ ID NO: 23, an HVR-H2 having the amino acid sequence of SEQ ID NO: 24, and an HVR-H3 having the amino acid sequence of SEQ ID NO: 25; and/or
   b) a light chain variable domain, and the light chain variable domain comprises an amino acid sequence selected from SEQ ID NOs: 5-8, or an amino acid sequence with at least about 95% homology to the amino acid sequence selected from SEQ ID NOs: 5-8 and wherein the light chain variable domain comprises an HVR-L1 having the amino acid sequence of SEQ ID NO: 30, an HVR-L2 having the amino acid sequence of SEQ ID NO: 31, and an HVR-L3 having the amino acid sequence of SEQ ID NO: 32.

2. The antibody of claim 1, wherein the antibody comprises a human heavy chain constant region, wherein the human heavy chain constant region is a human IgG4 heavy chain constant region.

3. The antibody of claim 2, wherein the human IgG4 heavy chain constant region comprises the amino acid sequence of SEQ ID NO: 37.

4. The antibody of claim 2, wherein the human IgG4 heavy chain constant region comprises an Fc region, and wherein the Fc region comprises a leucine to glutamate amino acid substitution at position 248 according to Kabat numbering convention.

5. The antibody of claim 4, wherein the leucine to glutamate amino acid substitution at position 248 inhibits the Fc region from interacting with an Fc receptor.

6. The antibody of claim 2, wherein the human IgG4 heavy chain constant region comprises an Fc region, and wherein the Fc region comprises a serine to proline amino acid substitution at position 241 according to Kabat numbering convention.

7. The antibody of claim 6, wherein the serine to proline amino acid substitution at position 241 prevents arm switching in the antibody.

8. The antibody of claim 1, wherein the heavy chain variable domain comprises an amino acid sequence of SEQ ID NO: 3, and wherein the light chain variable domain comprises an amino acid sequence of SEQ ID NO: 7.

9. The antibody or antigen-binding fragment of claim 1, wherein the antibody binds specifically to rat C1q, to both human C1q and mouse C1q, or to human C1q, mouse C1q, and rat C1q.

10. The antibody or antigen-binding fragment of claim 1, wherein the antigen-binding fragment is a Fab, F(ab')2 or Fab' fragment.

11. The antibody or antigen-binding fragment of claim 1, wherein the antibody has a dissociation constant ($K_D$) for human C1q that ranges from less than about 10 pM to less than about 5 pM; wherein the antibody has dissociation constant ($K_D$) for mouse C1q that ranges from less than about 125 nM to less than about 5 pM.

12. The antibody of claim 1, wherein the antibody specifically binds to and inhibits a biological activity of C1q.

13. The antibody of claim 12, wherein the biological activity is (1) C1q binding to an autoantibody, (2) C1q binding to C1r, (3) C1q binding to C1s, (4) C1q binding to phosphatidylserine, (5) C1q binding to pentraxin-3, (6) C1q binding to C-reactive protein (CRP), (7) C1q binding to globular C1q receptor (gC1qR), (8) C1q binding to complement receptor 1 (CR1), (9) C1q binding to beta-amyloid, or (10) C1q binding to calreticulin.

14. The antibody of claim 12, wherein the biological activity is (1) activation of the classical complement activation pathway, (2) activation of antibody and complement dependent cytotoxicity, (3) CH50 hemolysis, (4) synapse loss, (5) B-cell antibody production, (6) dendritic cell maturation, (7) T-cell proliferation, (8) cytokine production (9) microglia activation, (10) Arthus reaction, (11) phagocytosis of synapses or nerve endings, or (12) activation of complement receptor 3 (CR3/C3) expressing cells.

15. The antibody of claim 14, wherein CH50 hemolysis comprises human, mouse, and/or rat CH50 hemolysis.

16. The antibody of claim 15, wherein the antibody is capable of neutralizing from at least about 50%, to at least about 90% of CH50 hemolysis.

17. A pharmaceutical composition comprising the antibody of claim 1 and a pharmaceutically acceptable carrier.

18. A kit comprising an antibody of claim 1, and a package insert comprising instructions for using the antibody to treat a disease associated with complement activation in an individual in need of such treatment.

19. A humanized anti-C1q antibody, or an antigen-binding fragment thereof, the antibody comprising a heavy chain variable domain and a light chain variable domain, wherein the heavy chain variable domain comprises an amino acid sequence of SEQ ID NO: 3, and wherein the light chain variable domain comprises an amino acid sequence of SEQ ID NO: 7.

20. An anti-C1q antibody comprising a heavy chain variable domain and a light chain variable domain, wherein the heavy chain variable domain comprises an amino acid sequence of SEQ ID NO: 3, and wherein the light chain variable domain comprises an amino acid sequence of SEQ ID NO: 7.

21. The antibody of claim 20, wherein the antibody comprises a heavy chain constant region, wherein the heavy chain constant region is an IgG4 heavy chain constant region.

22. The antibody of claim 21, wherein the IgG4 heavy chain constant region comprises the amino acid sequence of SEQ ID NO: 37.

23. The antibody of claim 21, wherein the IgG4 heavy chain constant region comprises an Fc region, and wherein the Fc region comprises a leucine to glutamate amino acid substitution at position 248 according to Kabat numbering convention.

24. The antibody of claim 23, wherein the leucine to glutamate amino acid substitution at position 248 inhibits the Fc region from interacting with an Fc receptor.

25. The antibody of claim 21, wherein the IgG4 heavy chain constant region comprises an Fc region, and wherein the Fc region comprises a serine to proline amino acid substitution at position 241 according to Kabat numbering convention.

26. The antibody of claim 25, wherein the serine to proline amino acid substitution at position 241 prevents arm switching in the antibody.

27. The antibody of claim 20, wherein the antibody specifically binds to and inhibits a biological activity of C1q.

28. A pharmaceutical composition comprising the antibody of claim 20 and a pharmaceutically acceptable carrier.

29. A pharmaceutical composition comprising the antibody of claim 19 and a pharmaceutically acceptable carrier.

30. A pharmaceutical composition comprising the antibody of claim 22 and a pharmaceutically acceptable carrier.

* * * * *